United States Patent
Witte et al.

(10) Patent No.: US 12,402,967 B2
(45) Date of Patent: Sep. 2, 2025

(54) SURGICAL INSTRUMENTS WITH ACTUATABLE TAILPIECE

(71) Applicant: Cilag GmbH International, Zug (CH)

(72) Inventors: Spencer Witte, San Francisco, CA (US); Benjamin Dickerson, San Francisco, CA (US); Aren Calder Hill, Mountain View, CA (US); Trent Michael Callan, San Francisco, CA (US); Dillon Carey, Mountain View, CA (US); Matthew Stone, Mason, OH (US); Chris Birri, Cincinnati, OH (US); Reed Arenburg, Milford, OH (US)

(73) Assignee: Cilag GmbH International, Zug (CH)

( * ) Notice: Subject to any disclaimer, the term of this patent is extended or adjusted under 35 U.S.C. 154(b) by 435 days.

(21) Appl. No.: 17/729,835

(22) Filed: Apr. 26, 2022

(65) Prior Publication Data
US 2023/0338102 A1    Oct. 26, 2023

(51) Int. Cl.
*A61B 34/00* (2016.01)
*A61B 17/00* (2006.01)
(Continued)

(52) U.S. Cl.
CPC ........ *A61B 34/71* (2016.02); *A61B 17/00234* (2013.01); *A61B 34/37* (2016.02);
(Continued)

(58) Field of Classification Search
None
See application file for complete search history.

(56) References Cited

U.S. PATENT DOCUMENTS

| 5,792,165 A | * | 8/1998 | Klieman | ............ A61B 17/2909 |
| | | | | 606/174 |
| 2015/0119637 A1 | | 4/2015 | Alvarez et al. | |

(Continued)

FOREIGN PATENT DOCUMENTS

| KR | 20200109056 A | * | 9/2020 | ............. A61B 34/74 |
| WO | 2017059412 A1 | | 4/2017 | |

(Continued)

OTHER PUBLICATIONS

PCT International Search Report & Written Opinion pertaining to International Application No. PCT/IB2023/054178; Date of Mailing: Jul. 4, 2023.

*Primary Examiner* — James M Kish
*Assistant Examiner* — Sefra D. Manos
(74) *Attorney, Agent, or Firm* — Vorys, Sater, Seymour and Pease LLP

(57) ABSTRACT

A robotic surgical tool includes a handle providing a plurality of drive inputs, an elongate shaft including a plurality of sliding rack gears movably nested within a corresponding plurality of longitudinal channels defined along the shaft, and an end effector arranged at a distal end of the shaft and an articulable wrist interposing the end effector and the distal end. An actuation system housed in the handle actuates the drive inputs to move the sliding rack gears and thereby causes operation of at least one of the end effector and the wrist. A tailpiece is arranged at a proximal end of the shaft and is operably coupled to the sliding rack gears, the tailpiece includes a housing and a manual actuation device mounted to the housing and manually actuatable to act on the sliding rack gears and thereby operate at least one of the end effector and the wrist.

20 Claims, 37 Drawing Sheets

(51) Int. Cl.
 *A61B 34/30* (2016.01)
 *A61B 34/37* (2016.01)
 *B25J 9/10* (2006.01)
 *A61B 17/29* (2006.01)

(52) U.S. Cl.
 CPC ..... *B25J 9/102* (2013.01); *A61B 2017/00477* (2013.01); *A61B 2017/2927* (2013.01); *A61B 2034/305* (2016.02)

(56) References Cited

U.S. PATENT DOCUMENTS

| | | | |
|---|---|---|---|
| 2015/0182249 A1* | 7/2015 | Conlon | A61B 17/320068 606/169 |
| 2017/0095299 A1 | 4/2017 | Hendrick et al. | |
| 2017/0296257 A1* | 10/2017 | Shelton, IV | A61B 90/10 |
| 2018/0055583 A1* | 3/2018 | Schuh | A61B 34/37 |
| 2018/0168758 A1* | 6/2018 | Lutzow | A61B 34/30 |
| 2019/0175287 A1 | 6/2019 | Hill et al. | |
| 2020/0000538 A1* | 1/2020 | Rockrohr | F16H 25/2015 |
| 2020/0237454 A1 | 7/2020 | Anglese | |
| 2020/0237455 A1 | 7/2020 | Anglese | |
| 2020/0297444 A1* | 9/2020 | Camarillo | G16H 30/40 |
| 2022/0071725 A1 | 3/2022 | Rockrohr | |
| 2023/0338103 A1 | 10/2023 | Witte et al. | |

FOREIGN PATENT DOCUMENTS

| | | |
|---|---|---|
| WO | 2019147964 A1 | 8/2019 |
| WO | 2019191413 A1 | 10/2019 |
| WO | 2021011533 A1 | 1/2021 |
| WO | 2021259846 A2 | 12/2021 |
| WO | 2022018650 A1 | 1/2022 |

* cited by examiner

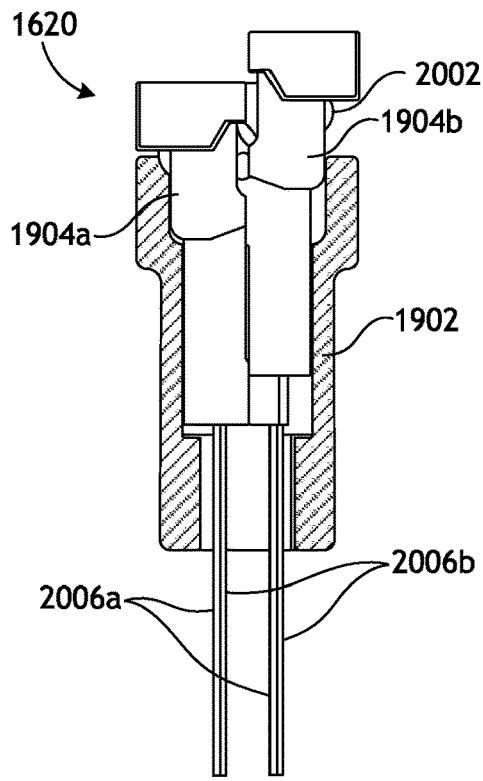
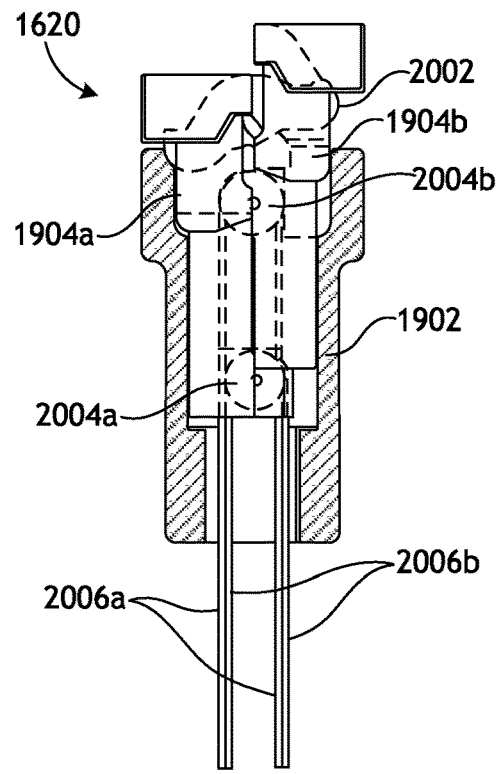
FIG. 20A
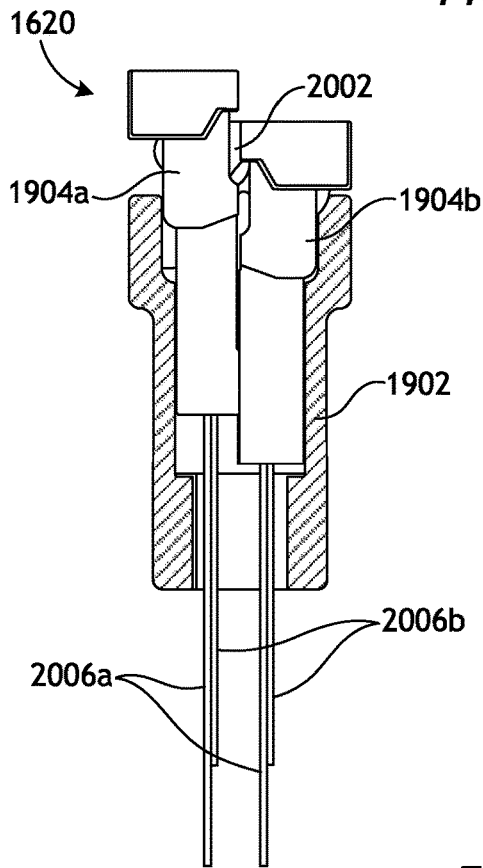
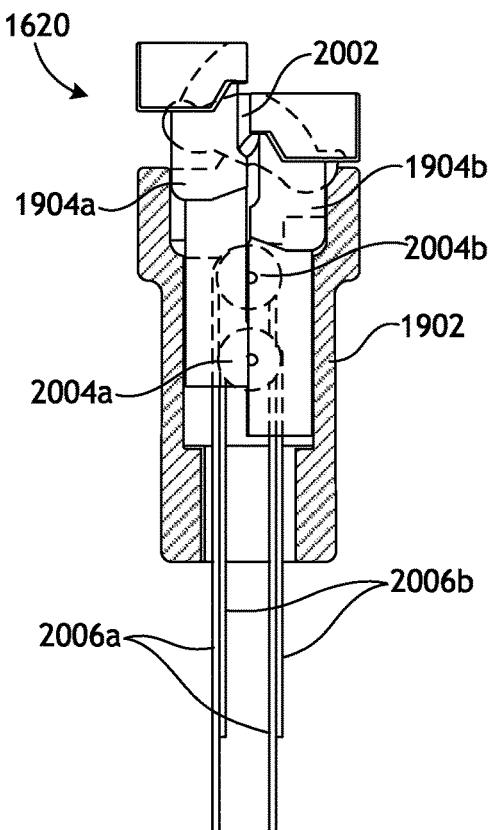
FIG. 20B

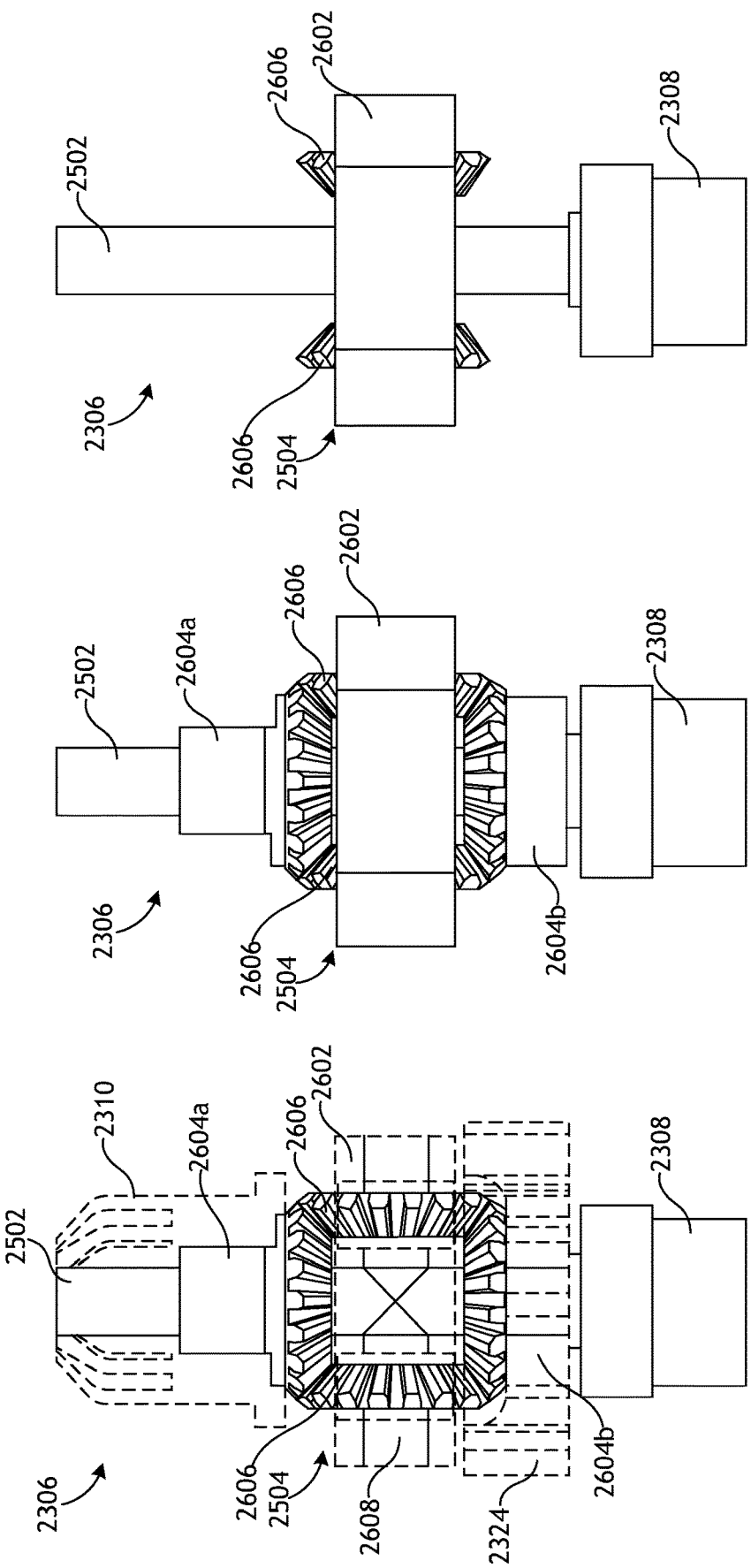

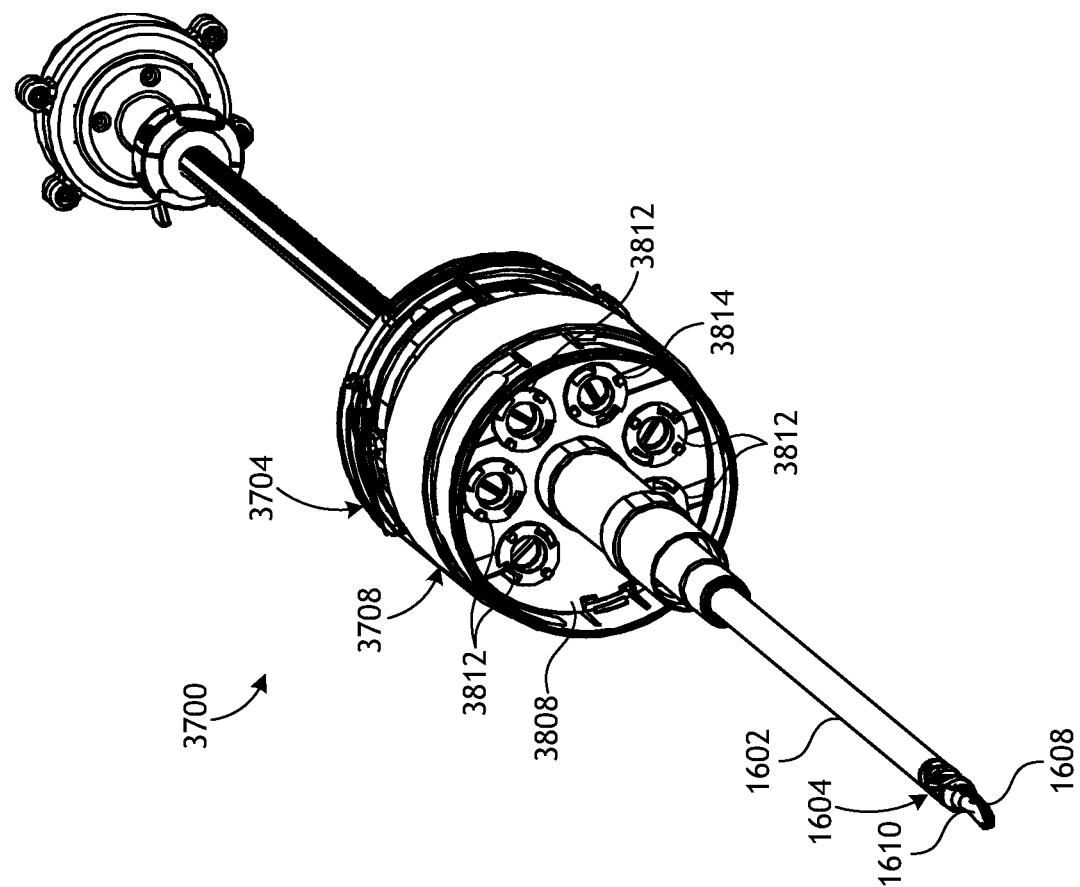
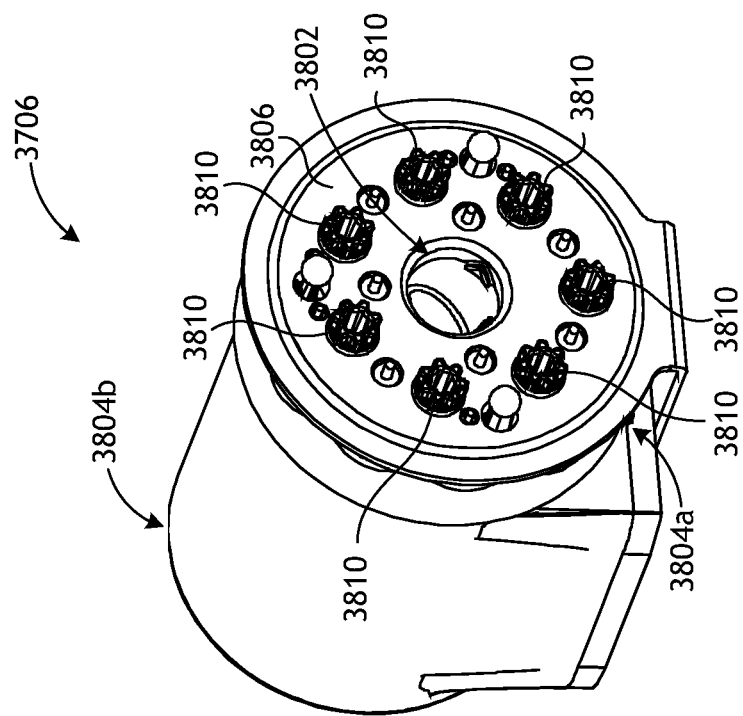
FIG. 38

SURGICAL INSTRUMENTS WITH ACTUATABLE TAILPIECE

TECHNICAL FIELD

The systems and methods disclosed herein are directed to robotic surgical tools and, more particularly to, actuatable tailpiece assemblies for surgical tools that allow a user to manually manipulate operation of the surgical tool.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar are used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system and thereby actively controlling the tension balance in the drive cables. Moving the drive cables articulates the end effector to desired angular positions and configurations.

Improvements to robotically-enabled medical systems will provide physicians with the ability to perform endoscopic and laparoscopic procedures more effectively and with improved ease.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 20A and 20B show example operation of the tailpiece (pantograph) of FIG. 19, according to one or more embodiments.

FIGS. 26A-26C are side views of the differential assembly of FIG. 25 in various stages of deconstruction, according to one or more embodiments.

FIG. 38 depicts separated isometric end views of the instrument driver and the surgical tool of FIG. 37.

DETAILED DESCRIPTION

1. Overview.

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance, to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto, as such concepts may have applicability throughout the entire specification.

A. Robotic System—Cart.

Figure 1:
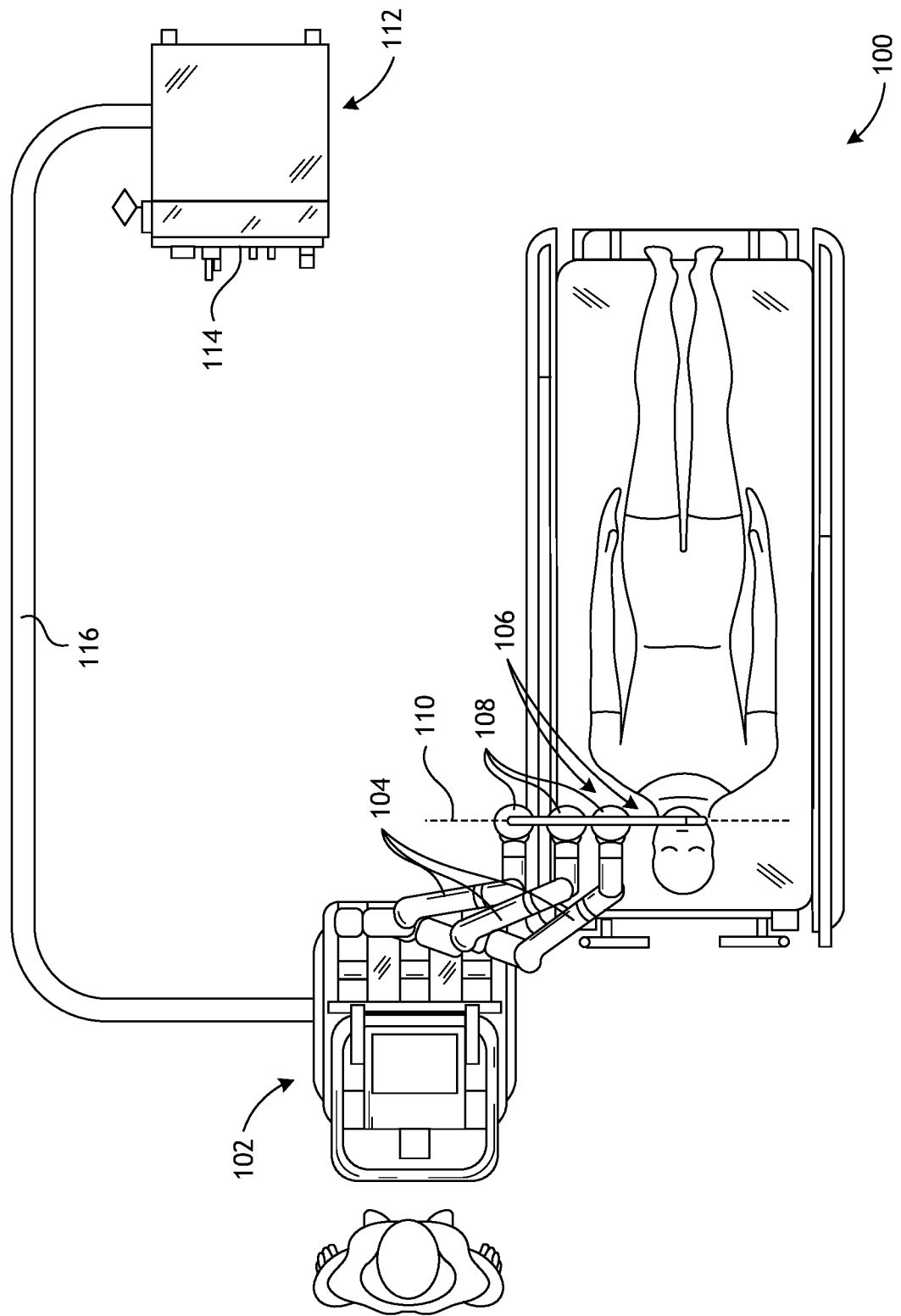
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or repositioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
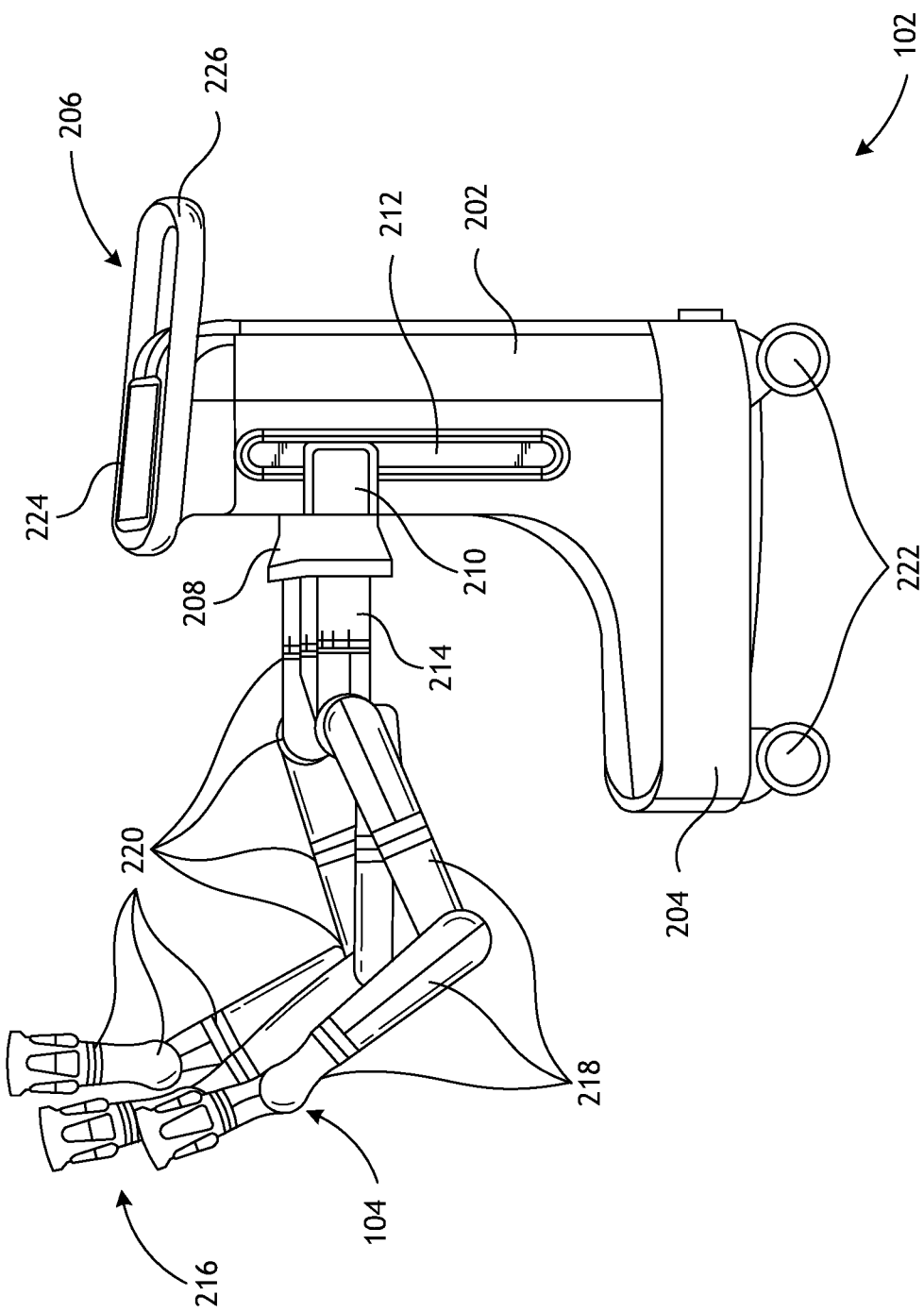
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, which are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, the carriage 208, and the arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
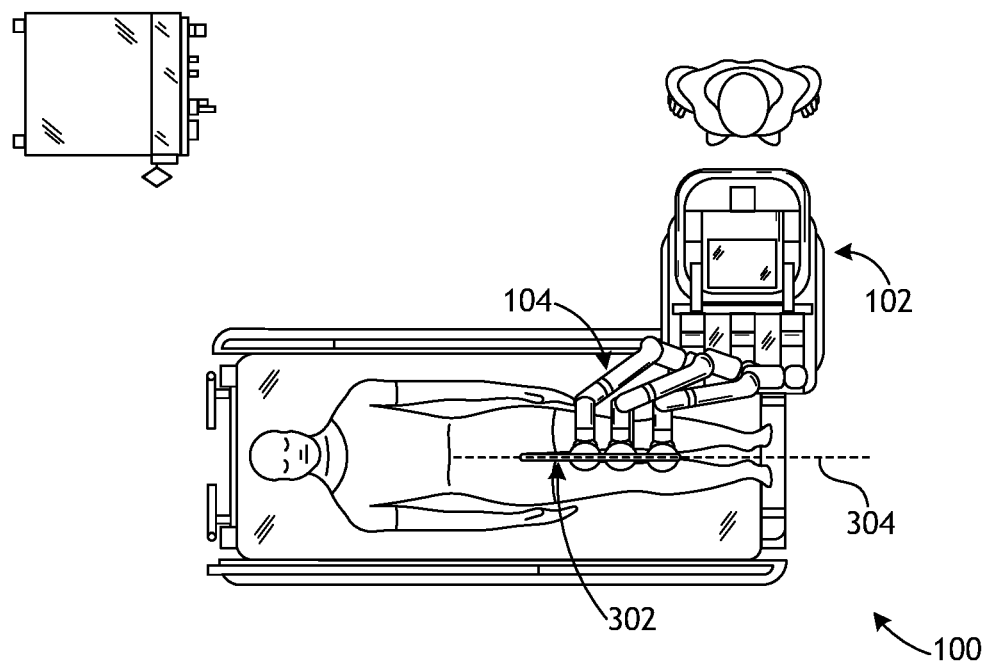
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
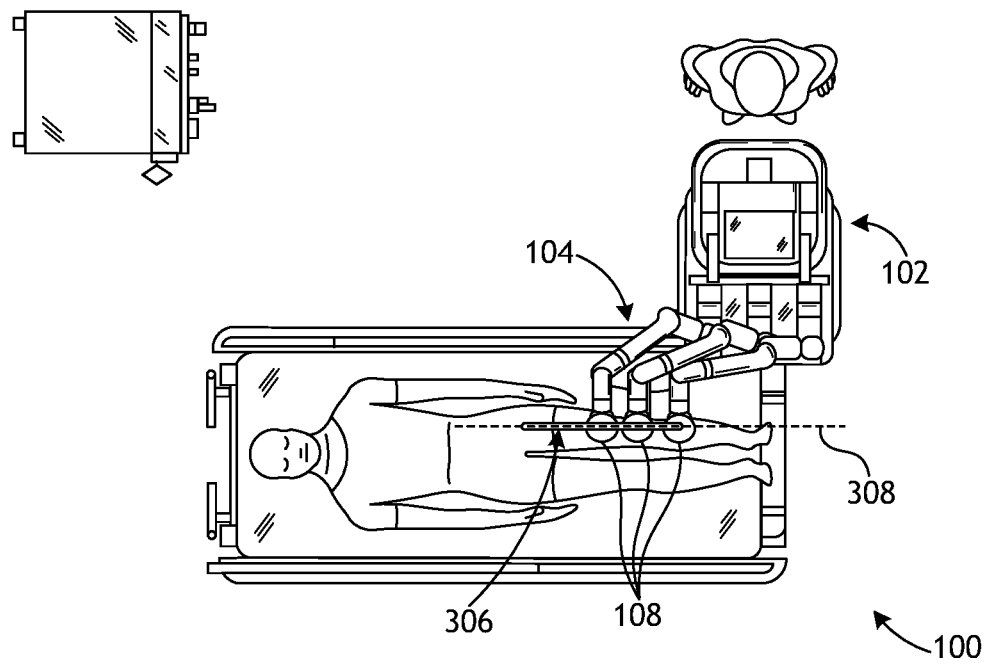
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
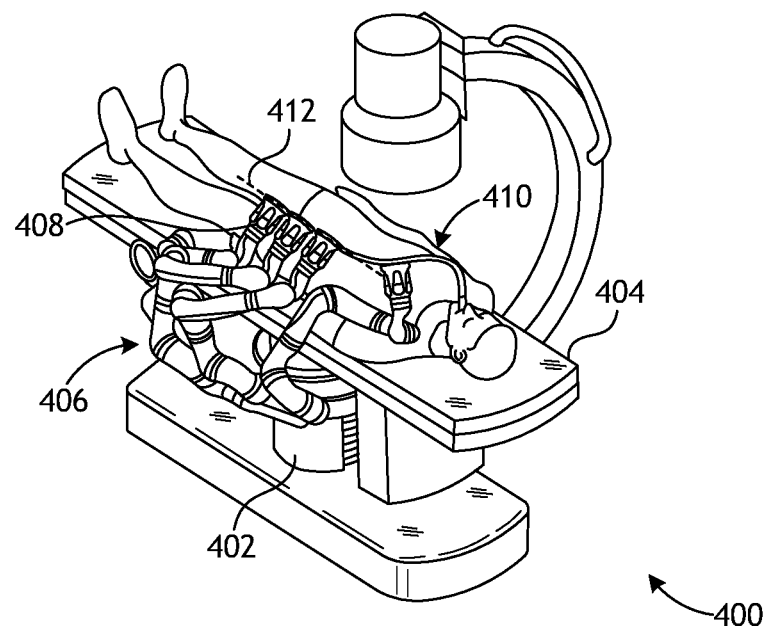
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
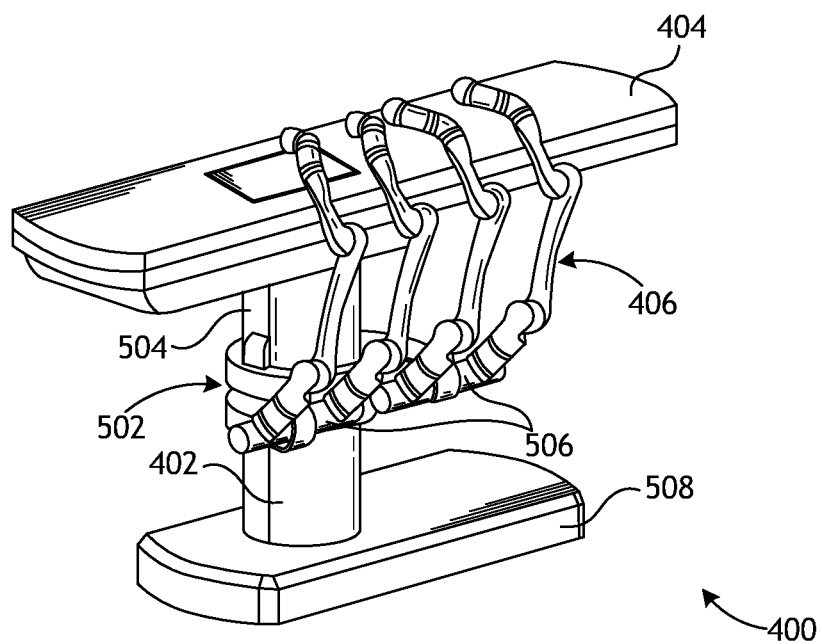
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
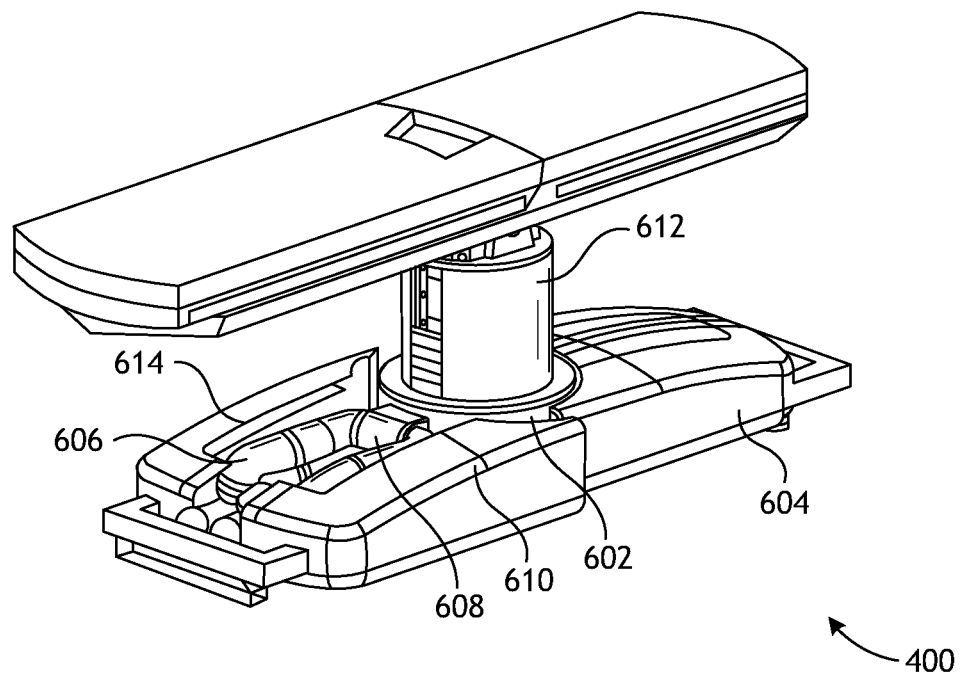
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
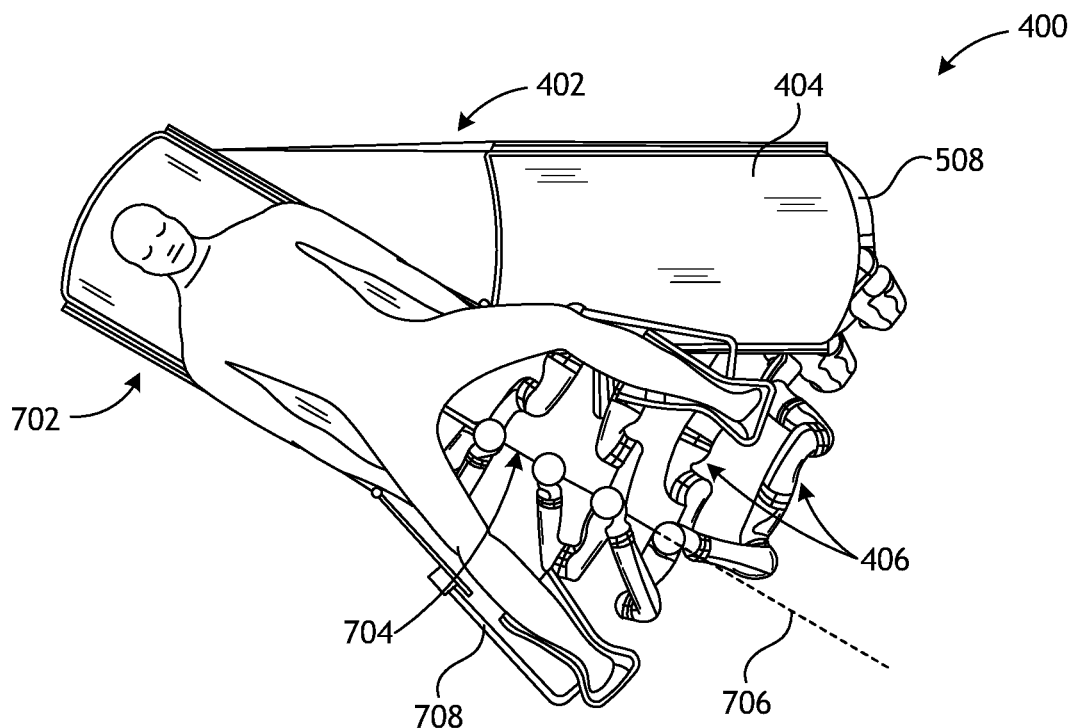
FIG. 7A illustrates an embodiment of a table-based robotic system configured for a ureteroscopy procedure.
Figure 7B:
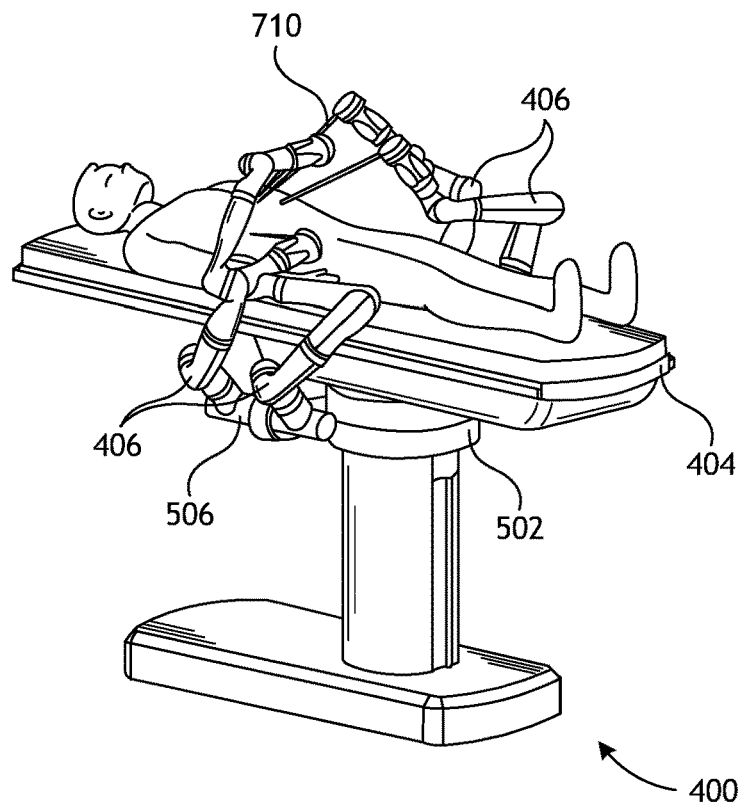
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
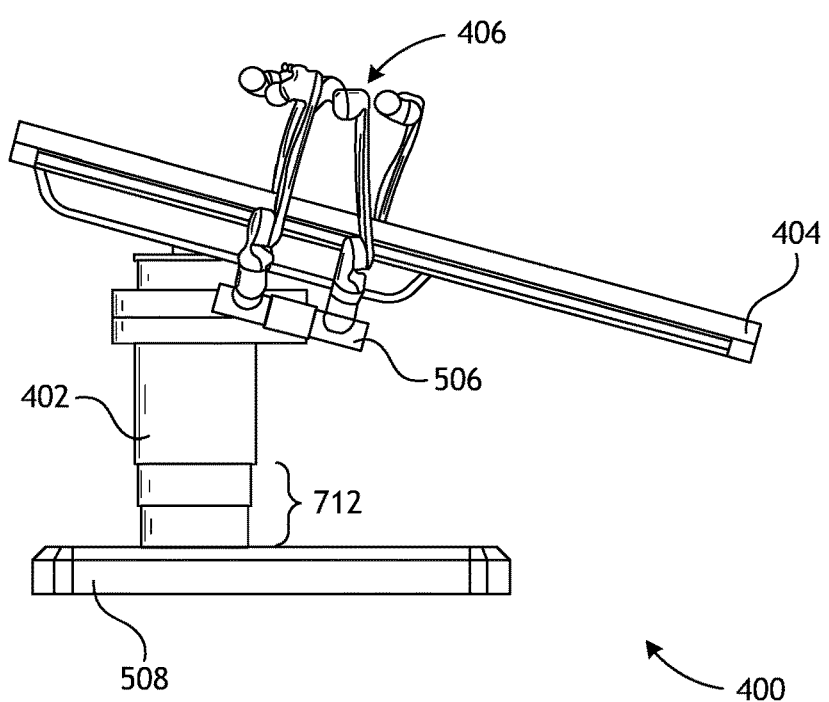
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
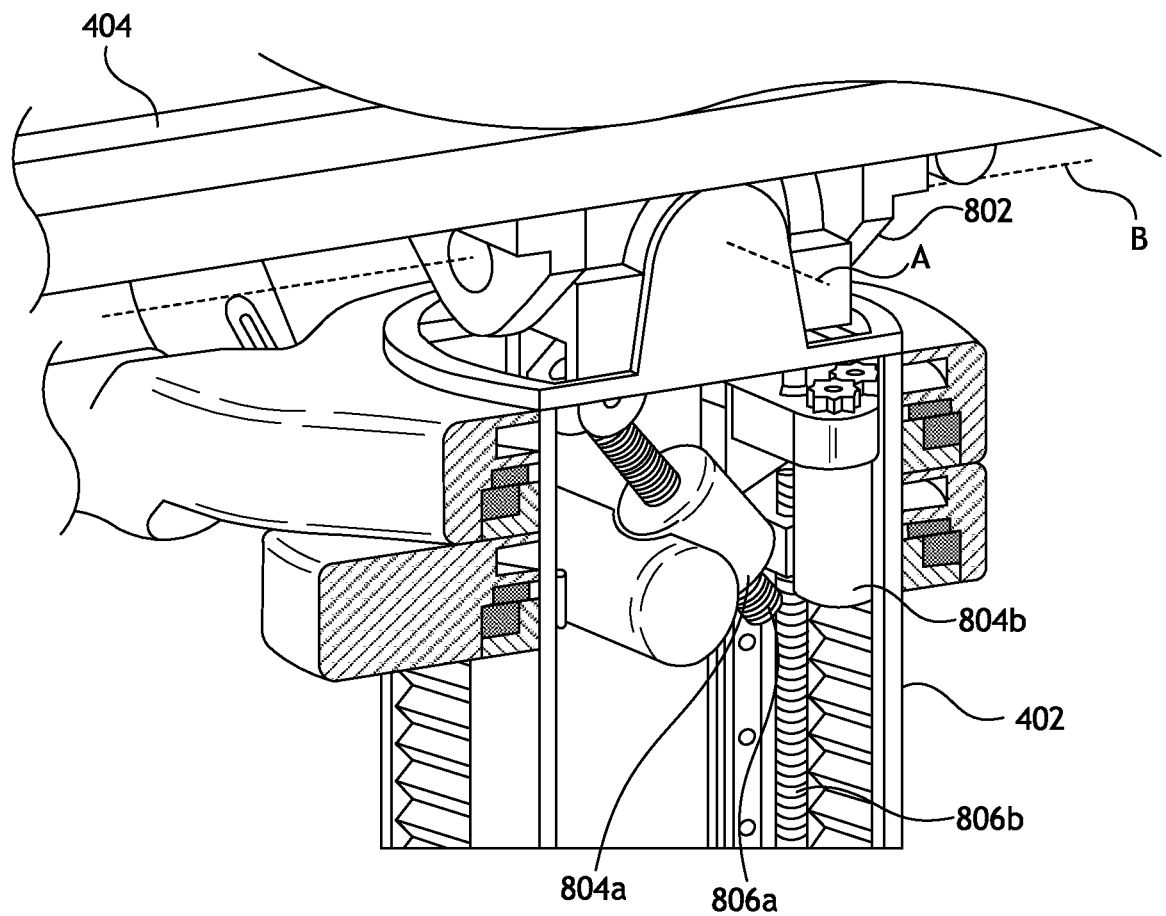
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
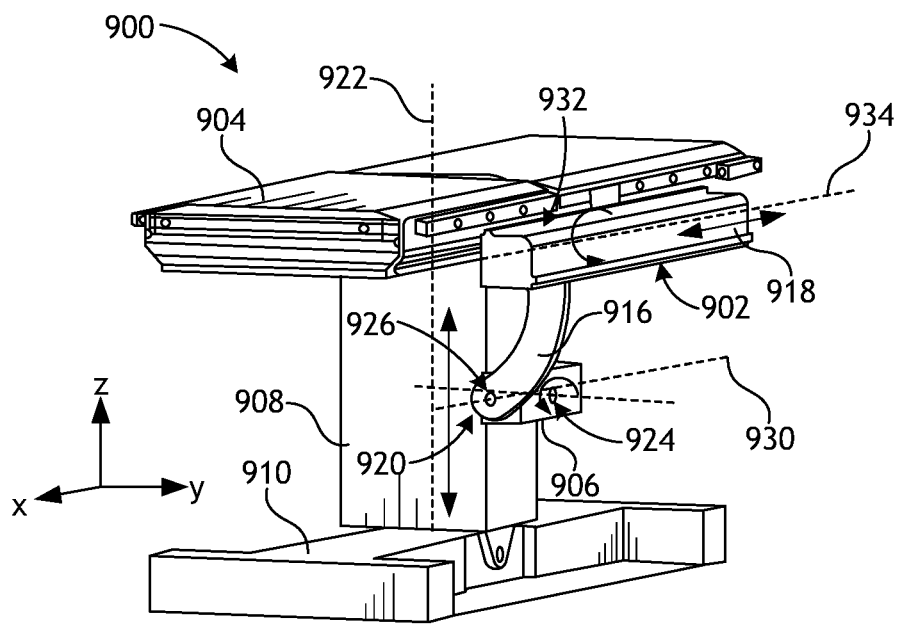
FIG. 9A illustrates an alternative embodiment of a table-based robotic system.
Figure 9B:
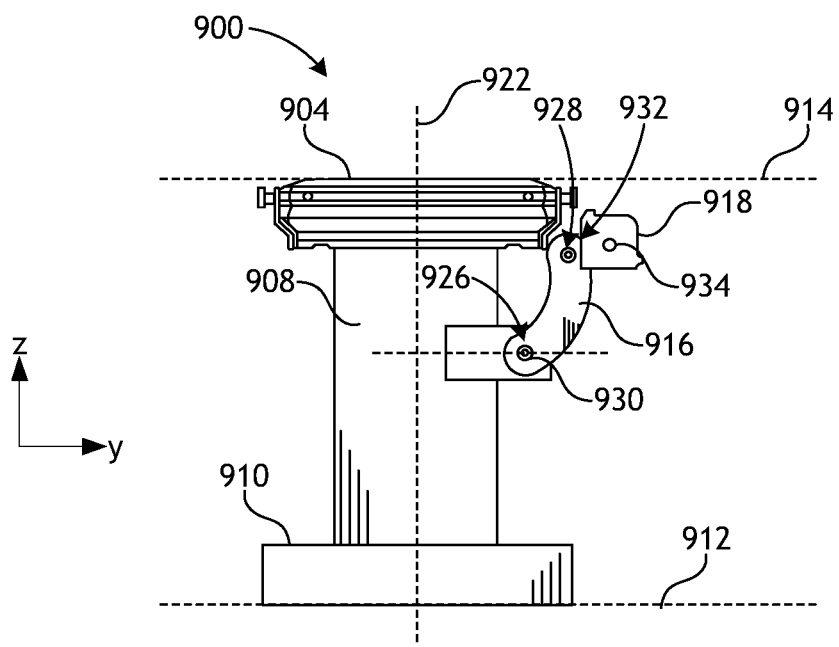
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
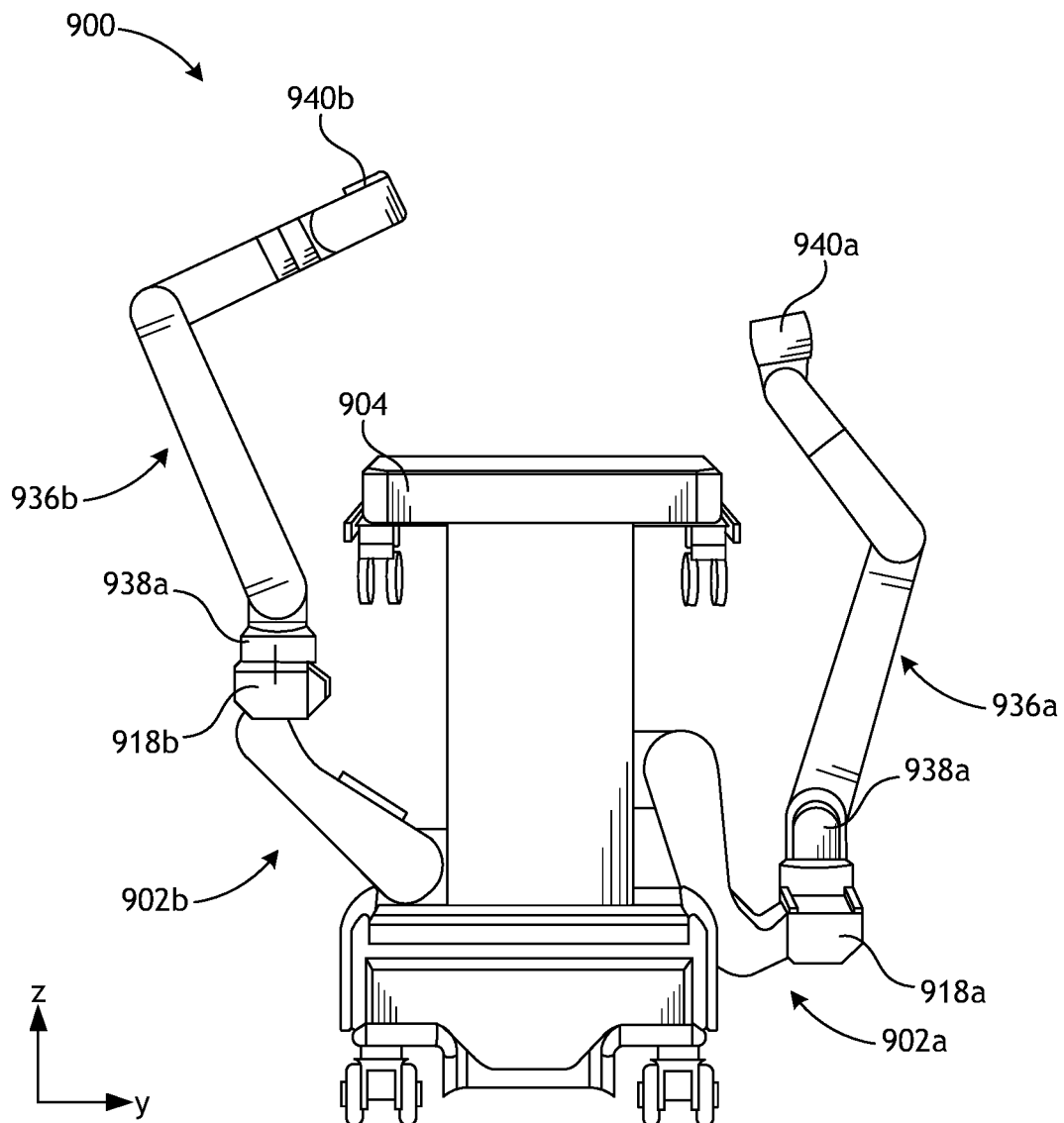
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electro-mechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
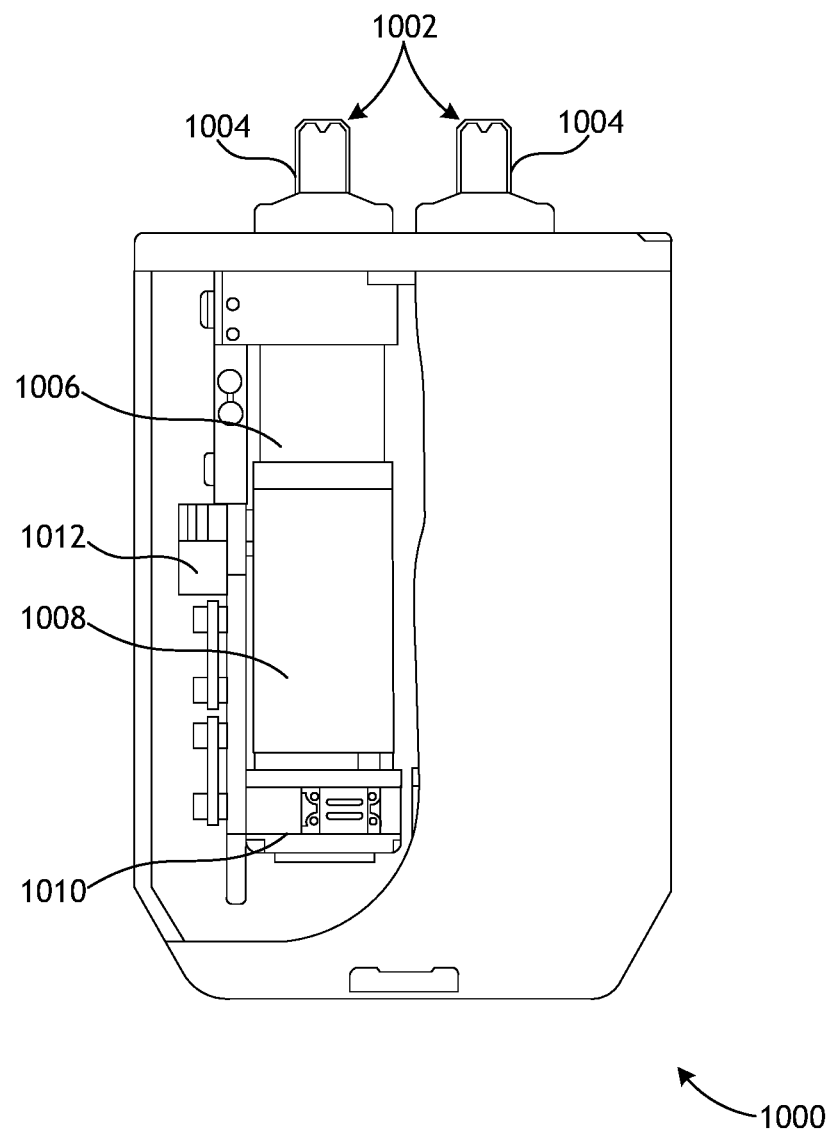
FIG. 10 illustrates an exemplary instrument driver.

FIG. 10 illustrates an example instrument driver 1000, according to one or more embodiments. Positioned at the distal end of a robotic arm, the instrument driver 1000 includes one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independently controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
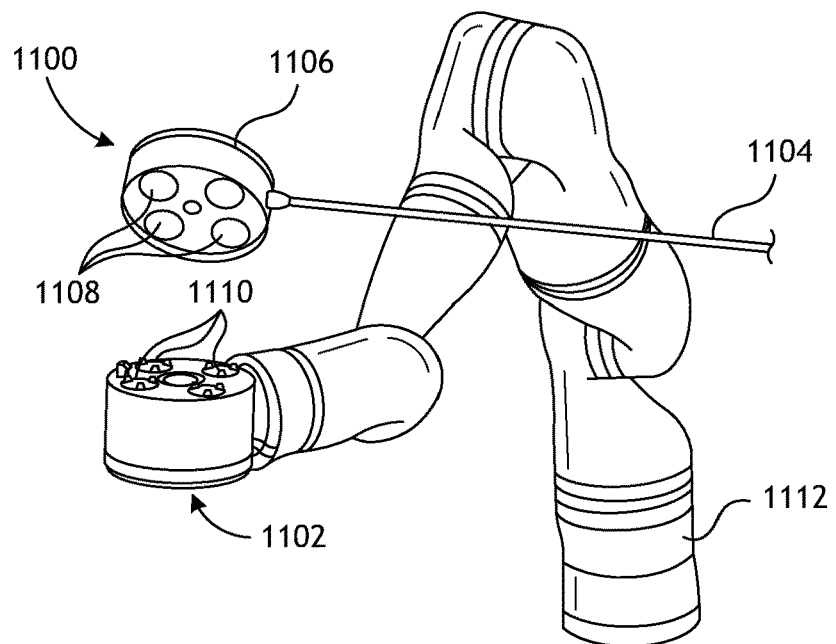
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
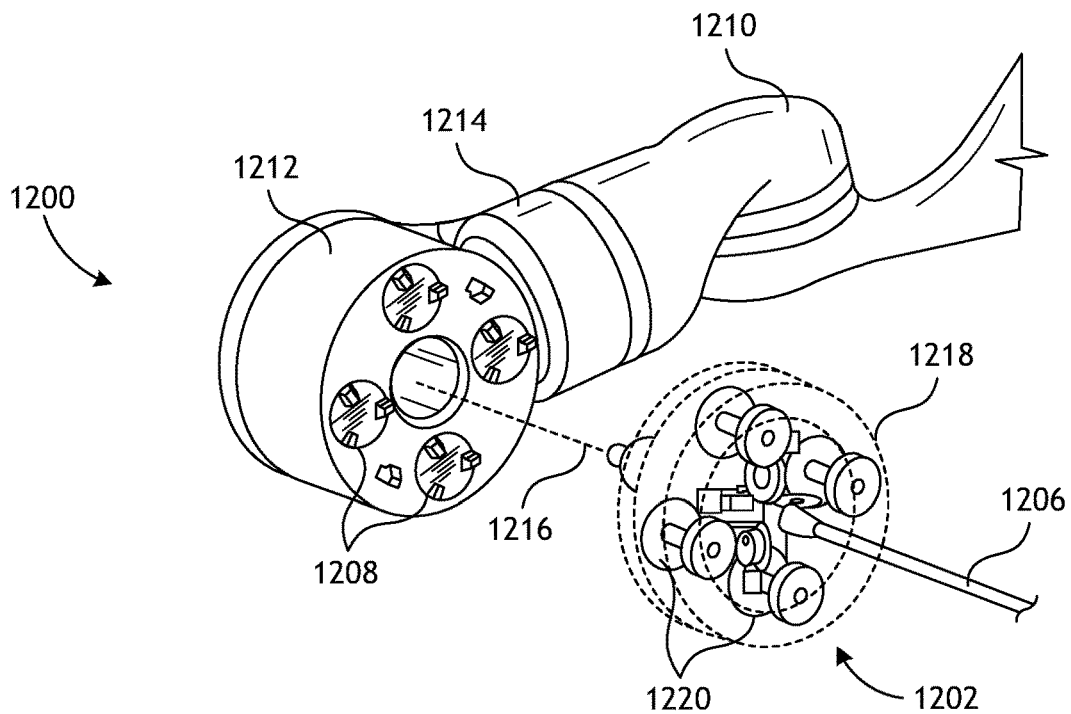
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
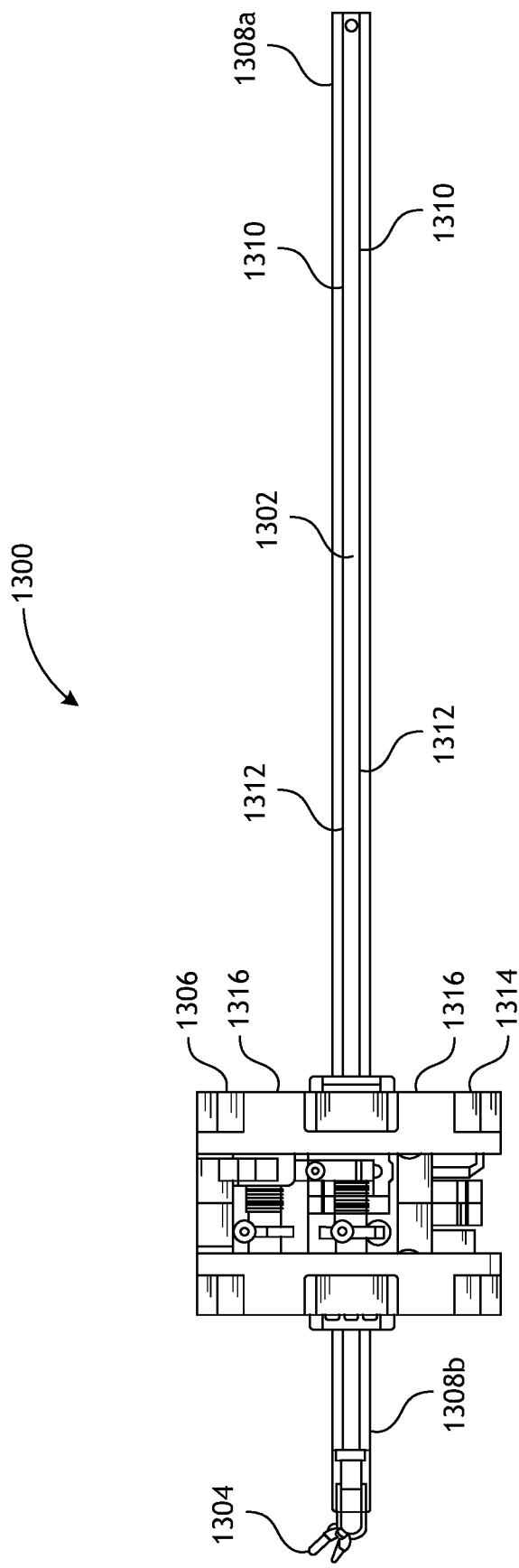
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument 1300, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
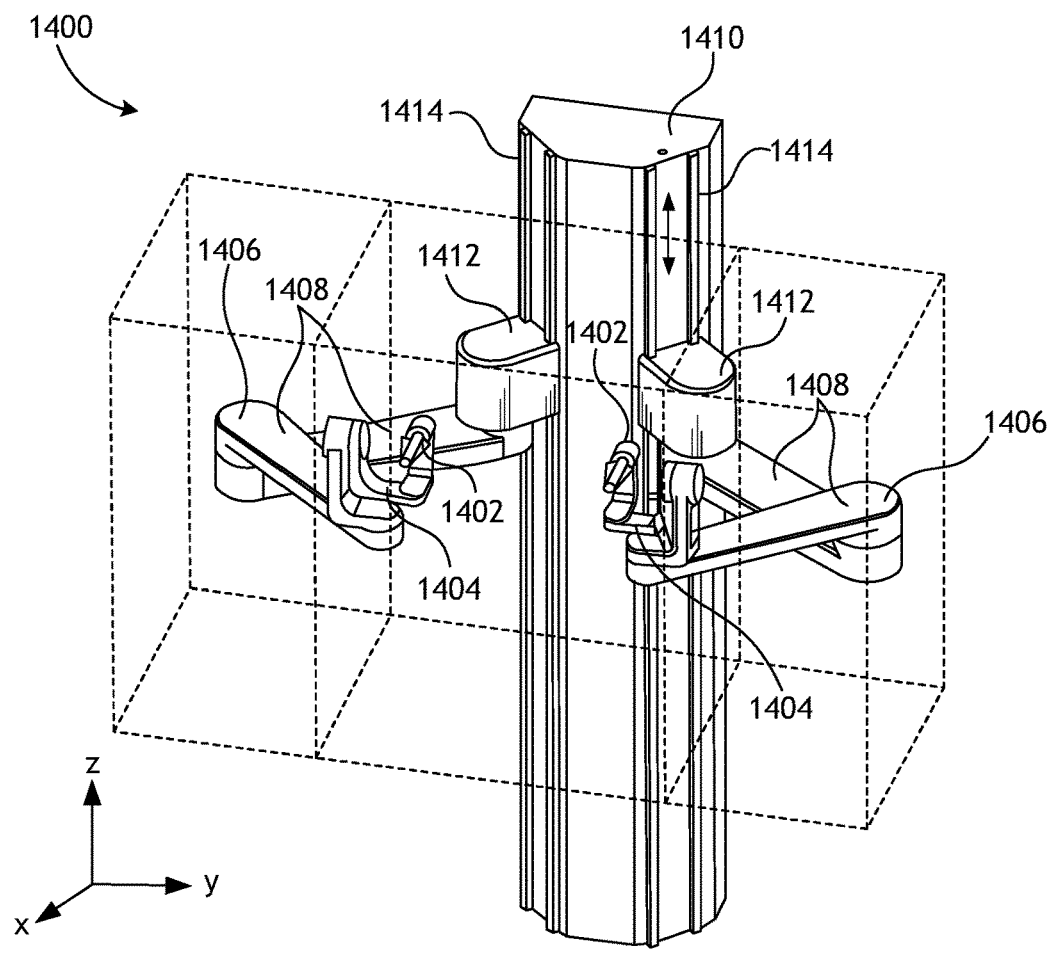
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
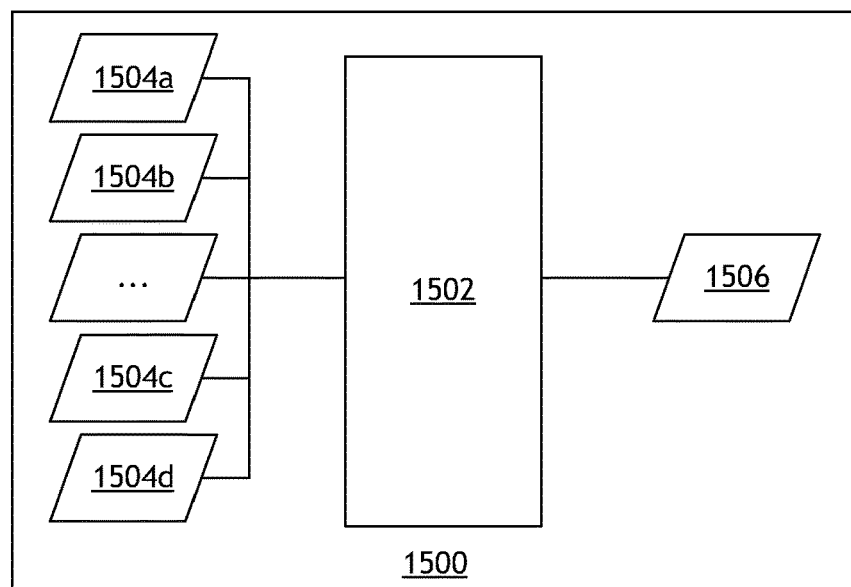
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504*a* that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504*b* to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504*c*. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504*d* may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504*a-d* in combination(s). In some cases, such a combination may use a probabilistic approach where the localization module 1502 assigns a confidence weight to the location determined from each of the input data 1504*a-d*. Thus, where the EM data 1504*c* may not be reliable (as may be the case where there is EM interference) the confidence of the location determined by the EM data 1504*c* can be decrease and the localization module 1502 may rely more heavily on the vision data 1504*b* and/or the robotic command and kinematics data 1504*d*.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Description.

Insertion Coupled Inserting Surgical Instrument

Figure 16:
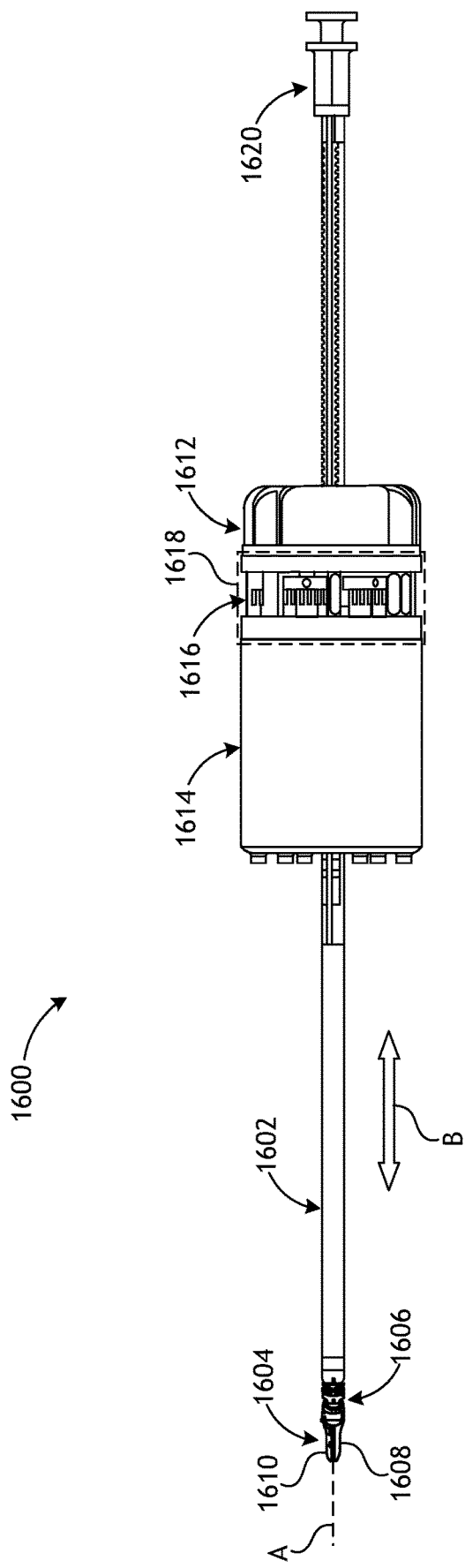
FIG. 16 is a side view of an example surgical tool that may incorporate some or all of the principles of the present disclosure.

FIG. 16 is a side view of an example surgical tool 1600 that may incorporate some or all of the principles of the present disclosure. The surgical tool 1600 may be similar in some respects to any of the surgical tools and medical instruments described above with reference to FIGS. 11-13 and, therefore, may be used in conjunction with a robotic surgical system, such as the robotically-enabled systems 100, 400, and 900 of FIGS. 1-9C. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602. In some embodiments, the wrist 1606 may be omitted, without departing from the scope of the disclosure.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a tissue grasper capable of grasping onto tissue or vessels. The end effector 1604 includes opposing jaws 1608, 1610 configured to move (articulate) between open and closed positions. Alternatively, the end effector 1604 may comprise other types of instruments with opposing jaws such as, but not limited to, a surgical stapler, a vessel sealer, surgical scissors, clip appliers, needle drivers, a babcock including a pair of opposed grasping jaws, bipolar jaws (e.g., bipolar Maryland grasper, forceps, a fenestrated grasper, etc.), etc.

One or both of the jaws 1608, 1610 may be configured to pivot to actuate the end effector 1604 between open and closed positions. In the illustrated example, both jaws 1608, 1610 simultaneously move to pivot the jaws 1608, 1610 between an open, unclamped position and a closed, clamped position and are thus referred to as "bifurcating" jaws. In other embodiments, however, only one of the jaws 1608, 1610 may be rotatable (pivotable) relative to the opposing jaw to actuate the end effector 1604 between the open and closed positions.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The end effector 1604 is depicted in FIG. 16 in the unarticulated position where the longitudinal axis of the end effector 1604 is substantially aligned with the longitudinal axis $A_1$ of the shaft 1602, such that the end effector 1604 is at a substantially zero angle relative to the shaft 1602. In the articulated position, the longitudinal axis of the end effector 1604 would be angularly offset from the longitudinal axis $A_1$ such that the end effector 1604 would be oriented at a non-zero angle relative to the shaft 1602.

Still referring to FIG. 16, the surgical tool 1600 may include a drive housing or "handle" 1612, and the shaft 1602 extends longitudinally through the handle 1612. The handle 1612 houses an actuation system designed to facilitate articulation of the wrist 1606 and actuation (operation) of the end effector 1604 (e.g., clamping, firing, rotation, articulation, energy delivery, etc.). As discussed in more detail below, the handle 1612 may include and otherwise house a plurality of drive gears that are actuatable to axially move (translate) a plurality of sliding rack gears nested within corresponding longitudinal channels defined along all or a portion of the shaft 1602. In some embodiments, the distal end of each rack gear is attached to distal cables that extend to the end effector 1604 or the wrist 1606 at the distal end of the shaft 1602, and the proximal end of the each rack gear is attached to proximal cables that extend to a proximal end of the shaft 1602. In other embodiments, however, the distal end of one or more of the rack gears may be directly attached to portions of the end effector 1604 or the wrist 1606 to enable a push-pull translation action (e.g., in the case of push/pull rods).

Selective actuation of one or more of the sliding rack gears, for example, may cause the end effector 1604 to articulate (pivot) relative to the shaft 1602 at the wrist 1606. Selective actuation of one or more additional sliding rack gears may cause the end effector 1604 to actuate (operate). Actuating the end effector 1604 depicted in FIG. 16 may entail closing and/or opening the jaws, 1608, 1610 and thereby enabling the end effector 1604 to grasp (clamp) onto tissue. In embodiments where the end effector 1604 comprises a vessel sealer, once tissue is grasped or clamped between the opposing jaws 1608, 1610, actuating the end effector 1604 may further include "firing" the end effector 1604, which may refer to causing a cutting element or knife (not visible) to advance distally within a slot or "guide track" defined in the first jaw 1610. As it moves distally within the guide track, the knife transects tissue grasped between the opposing jaws 1608, 1610.

The actuation system housed within the handle 1612 may further be designed to move the shaft 1602 relative to (through) the handle 1612 and along the longitudinal axis $A_1$. More particularly, the actuation system may also include a drive gear actuatable to engage a rack gear defined on the shaft 1602 itself; i.e., a "shaft rack gear". When the drive gear drives against the shaft rack gear, the shaft 1602 along with the nested sliding rack gears are moved (translated) axially relative to the handle 1612, as indicated by the arrows B. Moreover, as the shaft 1602 moves, the end effector 1604 and the wrist 1606 are simultaneously advanced or retracted, depending on the driving direction.

The handle 1612 may be operatively coupled to an instrument driver 1614 of a robotic surgical system. The instrument driver 1614 may be similar in some respects to the instrument drivers 1102, 1200 of FIGS. 11 and 12, respectively, and therefore may be best understood with reference thereto. Similar to the instrument drivers 1102, 1200, for example, the instrument driver 1614 may be mounted to or otherwise positioned at the end of a robotic arm (not shown) and is designed to provide the motive forces required to operate the surgical tool 1600. Unlike the instrument drivers 1102, 1200, however, the shaft 1602 of the surgical tool 1600 extends through and penetrates the instrument driver 1614.

The handle 1612 includes a plurality of rotatable drive inputs (not visible) that can be driven by a corresponding plurality of drive outputs (not visible) of the instrument driver 1614. Each drive input is actuatable to independently drive (actuate) various portions of the actuation system housed within the handle 1612 and thereby operate the surgical tool 1600, as generally described above. The number of drive outputs will generally be the same as the number of drive inputs, but the instrument driver 1614 can have additional drive outputs, without departing from the scope of the disclosure. Movement (rotation) of a given drive output correspondingly moves (rotates) an associated drive input and thereby operates the surgical tool 1600. Actuation of the drive inputs drives the various drive gears mentioned above, which may be arranged to drive the corresponding rack gears, and moving the rack gears causes the end effector 1604 to articulate and/or actuate (operate) and the shaft 1602 to axially move (translate) relative to the handle 1612.

In the illustrated embodiment, a decoupler subassembly or "decoupler" 1616 is arranged between and otherwise interposes the handle 1612 and the instrument driver 1614. Among other functions described herein, the decoupler 1616 transfers torque from the drive outputs of the instrument driver 1614 to the drive inputs of the handle 1612, and thus operates as a type of torque transfer apparatus. Once the drive outputs are operatively and indirectly coupled to corresponding drive inputs via the decoupler 1616, rotational torque may be transferred from the drive outputs to the corresponding drive inputs through (via) the decoupler

1616, thus being able to operate the handle 1612. As discussed in more detail below, the decoupler 1616 may also be advantageous in transferring insertion motion (e.g., movement of the shaft 1602) to all the drive inputs, thus allowing one robot motor to control insertion of the surgical tool 1600, while allowing the other motors of the instrument driver 1614 to drive the sliding rack gears independent of insertion.

For procedures that require a sterile environment, an instrument sterile adapter 1618 (shown in dashed lines) connected to a sterile drape may be incorporated into the surgical tool 1600 upon mounting to the instrument driver 1614. Depending on design or application, the decoupler 1616 can form part of the instrument driver 1614, the sterile adaptor 1618, the handle 1612, or a combination of the foregoing. Since it has many complex parts, it may be advantageous for the decoupler 1616 to not be integrated with the handle 1612, which is commonly the disposable portion of the surgical tool 1600. This reduces the cost of the surgical tool 1600 and the quantity of decouplers 1616 needed per procedure. In some embodiments, the decoupler 1616 could be integrated into the sterile adaptor 1618, as shown in FIG. 16. The sterile adaptor 1618 can be designed to have a longer lifetime than the surgical tool 1600 and fewer are needed per procedure, thus, moving the decoupler 1616 can reduce the cost of the device. Moreover, this has the benefit that the instrument driver 1614 remains unchanged, which is important for driving non-inserting tools, such as endoscopy tools.

In other embodiments, however, the decoupler 1616 may be integrated into and otherwise form part of the instrument driver 1614. In such embodiments, the decoupler 1616 is never disposed of and thus entails a one-time cost for the user. However, this may create an issue when trying to drive non-inserting instruments. In such scenarios, the decoupler 1616 may be configured such that each motor of the instrument driver 1614 has two outputs; one output would be the insertion-decoupled motion while the other output is not. The instrument driver 1614 would then be designed to selectively engage the appropriate outputs. This may be helpful for instruments where both coupled and uncoupled motions are desired. For example, a suction irrigator with valves driven by the inputs could operate with coupled motions for the wrist 1606 and uncoupled motion for the valves that are not inserting with the tool shaft 1602.

In yet other embodiments, the decoupler 1616 could be a stand-alone separable assembly that can attach to the instrument driver 1614 as desired. In such embodiments, the decoupler 1616 could be designed to be mounted below the sterile barrier 1618, or outside of it. The stand-alone version of the decoupler 1616 may be designed and otherwise capable of being sterilized for multiple procedures (e.g., 100 uses), and multiple different tools of single or multiple use design could be attached on top of it.

Lastly, in some embodiments, the surgical tool 1600 may include a tailpiece 1620 arranged at the proximal end of the shaft 1602. The tailpiece 1620, its operation, and various embodiments will be described in more detail below. Briefly, however, the tailpiece 1620 may comprise a mechanical device that provides a means for manually controlling the end effector 1604 and/or the wrist 1606. The tailpiece 1620 can be designed to hold a mechanism referred to herein as a "pantograph" or a "pantograph button". The pantograph essentially acts as a mirror to the wrist 1606 ensuring that the system maintains tension in the surgical tool 1600 when disconnected from the instrument driver 1614 (e.g., the robot). As described herein, however, the tailpiece 1620 can be provided in various forms and still perform essentially the same function, without departing from the scope of the present disclosure. In at least one embodiment, as described herein, the pantograph can receive a separate input for manual activation, such as a slider that allows the user to manually actuate one of the degrees of freedom of the wrist 1606, such as jaw opening.

Figure 17A:
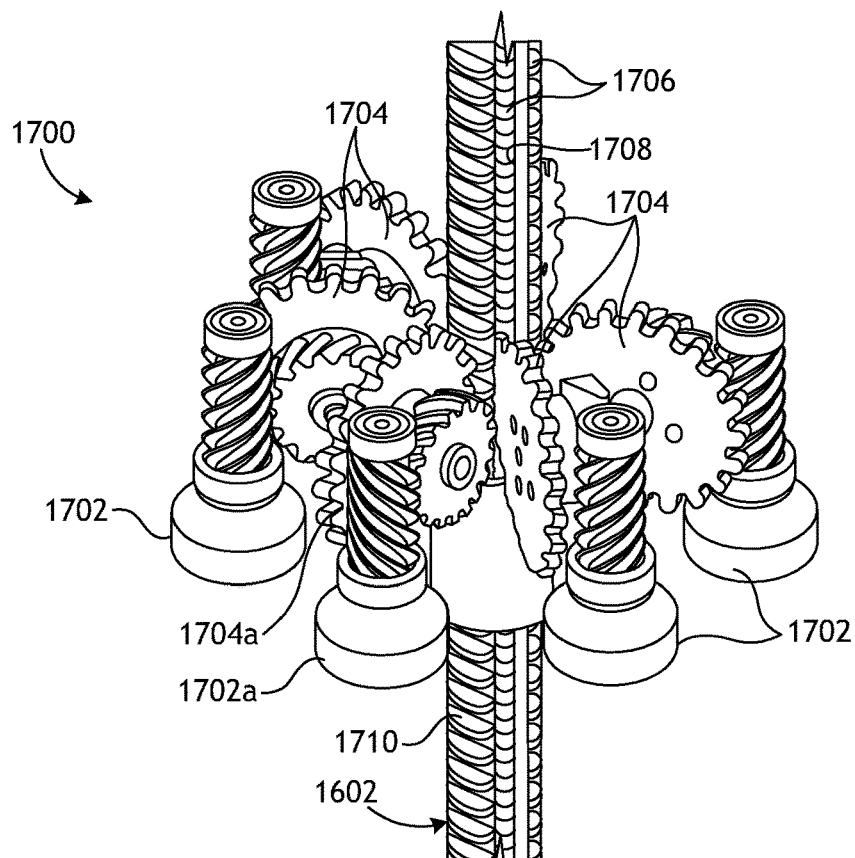
FIGS. 17A and 17B are isometric and bottom views, respectively, of an example actuation system, according to one or more embodiments.
Figure 17B:
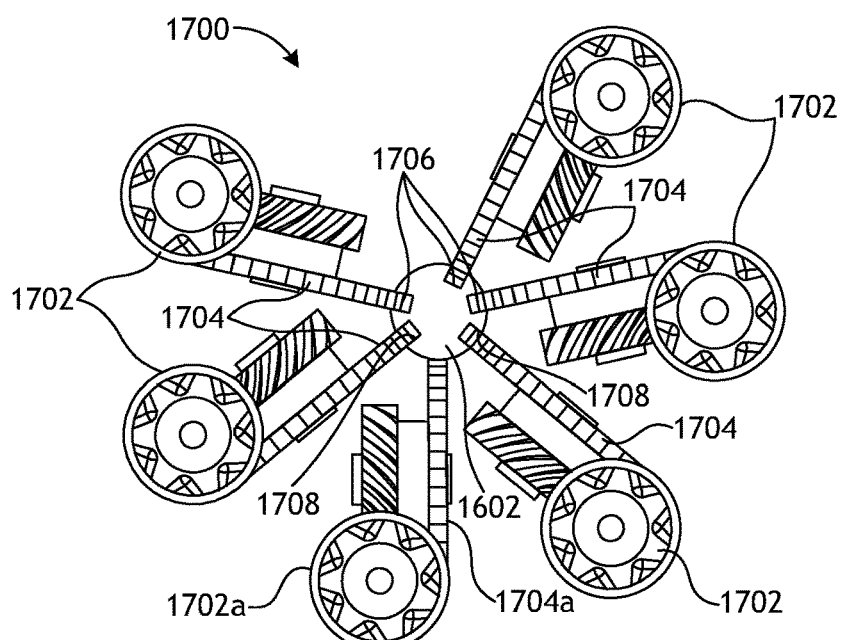

FIGS. 17A and 17B are isometric and bottom views, respectively, of an example actuation system 1700, according to one or more embodiments. The actuation system 1700 may be housed within the handle 1612 (FIG. 16) and operable to actuate (operate) the end effector 1604 (FIG. 16), articulate the wrist 1606 (FIG. 16), and axially move (translate) the shaft 1602 relative to (i.e., through) the handle 1612. Several parts and structural elements of the handle 1612, such as the outer housing, are omitted from FIGS. 17A-17B to enable ease of viewing of the actuation system 1700 for purposes of discussion.

As illustrated, the actuation system 1700 may include a plurality of rotatable drive inputs 1702. As discussed above, the drive inputs 1702 can be driven by a corresponding plurality of drive outputs of the instrument driver 1614. In embodiments that include the decoupler 1616, however, a transmission differential or differential assembly provided by the decoupler 1616 will axially interpose corresponding drive inputs and drive outputs, such that any rotational torque provided by a given drive output will be transferred to the corresponding drive input via the corresponding transmission differential.

Rotating a given drive input 1702 will cause a corresponding drive gear 1704 to rotate (operate), and each drive gear 1704 may be arranged to drive against an adjacent sliding rack gear 1706. Each sliding rack gear 1706 is movably nested within a corresponding longitudinal channel 1708 defined along all or a portion of the shaft 1602. In the illustrated embodiment, the drive gears 1704 are depicted as spur gears with teeth matable with corresponding teeth defined on the opposing sliding rack gear 1706. Accordingly, the drive gears 1704 may alternatively be referred to herein as "spur" gears, and operation of the spur gears 1704 and corresponding rack gears 1706 may be similar to rack-and-pinion operation. Driving a given sliding rack gear 1706 will urge the sliding rack gear 1706 to move (slide) within the corresponding longitudinal channel 1708, and moving the rack gears 1706 within the channels 1708 may actuate (operate) the end effector 1604 (FIG. 16) and/or articulate the wrist 1606 (FIG. 16).

The rack gears 1706 may prove advantageous over cable-based systems since they have a much larger cross-sectional area than cables, so their stiffness is much higher than cables. Consequently, the performance of the tool can be more robust and predictable. Moreover, rack gears 1706 enable the driving of instrument end effectors that do not use cables, such as push/pull rods that are often used in certain designs, such as vessel sealers or staplers.

One of the drive inputs, shown as drive input 1702a, may be configured to cause a corresponding shaft drive gear 1704a to rotate (operate), and the shaft drive gear 1704a may be arranged to drive against an adjacent shaft rack gear 1710. Accordingly, the drive input 1702a may be referred to herein as the "shaft" drive input 1702a. As illustrated, the shaft rack gear 1710 may form part of and may otherwise be defined along all or a portion of the outer surface of the shaft 1602. Driving against the shaft rack gear 1710 will cause the shaft 1602 to move (translate) axially relative to (i.e., through) the handle 1612 (FIG. 16).

Movement of the shaft 1602 via actuation of the shaft drive input 1702a is one reason why the decoupler 1616 (FIG. 16) may be advantageous or even needed in the surgical tool 1600 (FIG. 16). As the shaft drive gear 1704a is actuated (driven) to move the shaft 1602, the remaining drive gears 1704 must also be driven or the sliding rack gears 1706 will be inadvertently moved, thus affecting articulation, end effector operation, etc. This would require all motors in the instrument driver 1614 (FIG. 16) to operate concurrently whenever the shaft 1602 is axially translated. Moreover, if the shaft drive gear 1704a is actuated (driven) without driving any of the remaining drive gears 1704, the shaft 1602 would bind against opposing forces or would inadvertently move the wrist 1606 (FIG. 16) or actuate the end effector 1604 (FIG. 16). As described in more detail below, the differential assemblies included in the decoupler 1616 may be configured to transfer insertion motion (e.g., movement of the shaft 1602) to all the drive inputs 1702, thus allowing one robot motor to control insertion of the surgical tool 1600 (FIG. 16), while allowing the other motors of the instrument driver 1614 to drive the sliding rack gears 1706 independent of insertion. In addition to applying insertion motion to all inputs, the decoupler 1616 may be designed to cancel out reaction loads, such that tensions applied to wrist actuators are not realized as reaction torques on the insertion driver.

In some embodiments, a gear train including one or more intermediate gears may interpose each drive input 1702 and the corresponding drive gear 1704, such that rotating the drive input 1702 will correspondingly rotate the corresponding drive gear 1704 via the interposing gear train. A similar type of gear train may interpose the shaft drive input 1702a and the shaft drive gear 1704a. Those skilled in the art will readily appreciate that this gear train can assume a variety of configurations. In the illustrated embodiment, for example, the gear train includes mating helical gears that transition the rotational axis of the drive inputs 1702, 1702a 90° to enable the drive gears 1704 and the shaft drive gear 1704a to properly engage the rack gears 1706 and the shaft rack gear 1710, respectively. In at least one embodiment, however, the gear train may be omitted and rotating the drive inputs 1702, 1702a may directly drive the adjacent rack gear 1706, 1710, without departing from the scope of the disclosure.

Figure 17C:
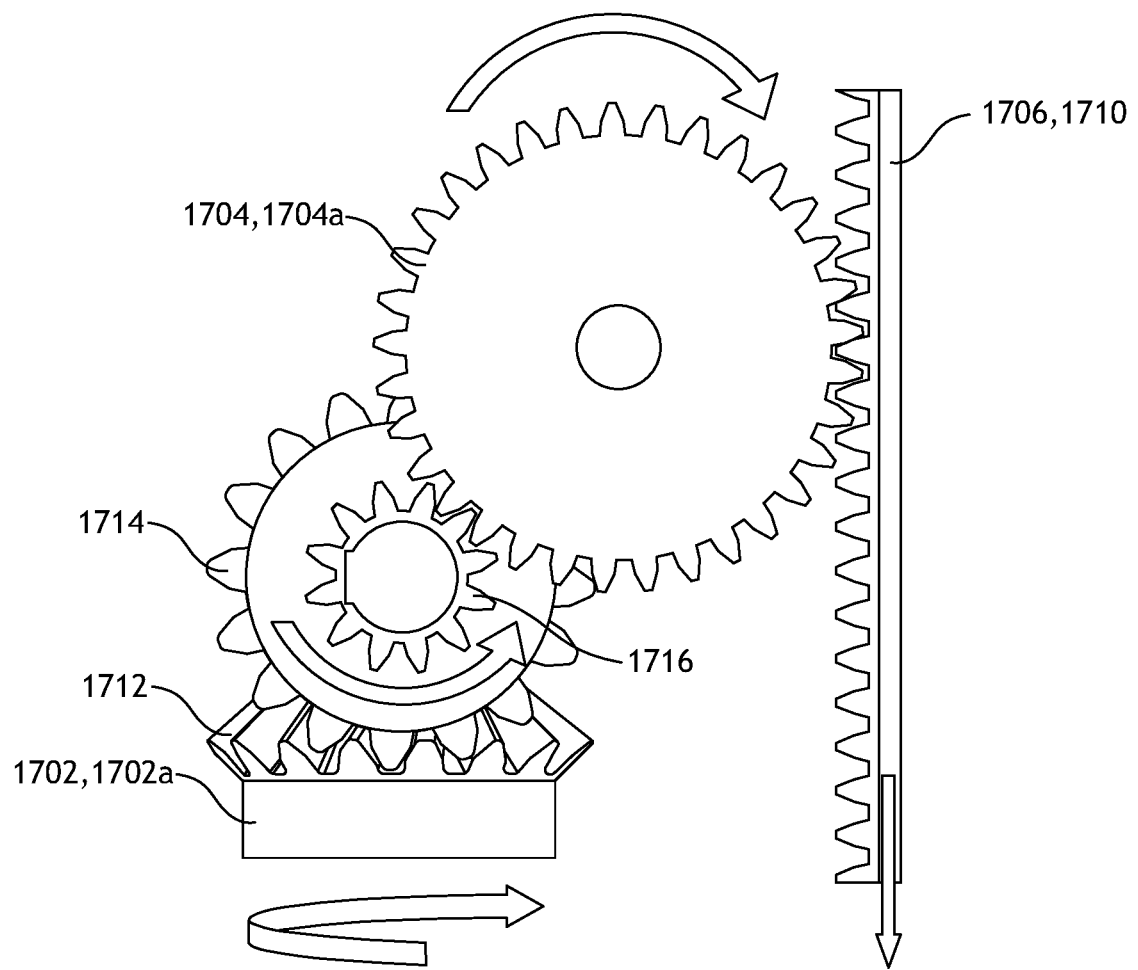
FIG. 17C is another example of a gear train that may be used to transfer rotational torque from the drive inputs to the rack gears.

FIG. 17C is another example of a gear train that may be used to transfer rotational torque from the drive inputs 1702, 1702a to the rack gears 1706 or the shaft rack gear 1710, respectively. In the illustrated embodiment, the drive input 1702, 1702a may include a bevel drive gear 1712 arranged to drive a bevel driven gear 1714, and the bevel driven gear 1714 may further include a spur gear 1716 arranged to drive the drive gear 1704, 1704a. The intermeshed bevel gears 1712, 1714 facilitates the directional change required in the handle 1612 (FIG. 16). Through the depicted gear train arrangement, rotation of the drive input 1702, 1702a will correspondingly move the rack gears 1706 or the shaft rack gear 1710. In other embodiments, other known gearing mechanisms may be utilized or combined in any number of configurations and dimensioned for optimal torque and/or speed outputs. In at least one embodiment, for example, the gear train may incorporate worm gears or a combination of bevel and spur gears.

FIGS. 18A-18D are schematic diagrams of example operation of a portion of the actuation system 1700, according to one or more embodiments. As mentioned above, the actuation system 1700 is housed within the handle 1612 and includes the drive gears 1704 rotatable (operable) to drive against adjacent sliding rack gears 1706. As also mentioned above, the rack gears 1706 are nested within corresponding longitudinal channels 1708 defined along all or a portion of the shaft 1602. As depicted, the drive and rack gears 1704, 1706 provide or define meshing gear teeth that allows the drive gears 1704 to drive the rack gears 1706 longitudinally along the length of the shaft 1602. A distal structure 1802a (shown in dashed lines) is provided at the distal end of the shaft 1602 and is representative of the end effector 1604, the wrist 1606 (FIG. 16), or another mechanism that may be driven or operated through operation of the actuation system 1700. Similarly, a proximal structure 1802b (shown in dashed lines) is positioned at the proximal end of the shaft 1602 and is representative of the tailpiece 1620 (FIG. 16) or another mechanism that may be driven or operated through operation of the actuation system 1700.

In some embodiments, a distal cable 1804a may be attached to the distal end of each rack gear 1706, and a proximal cable 1804b may be attached to the proximal end of each rack gear 1706. In the illustrated embodiment, the distal cable 1804a extends from one of the rack gears 1706, wraps around a distal pulley 1806a, and is attached to an opposing rack gear 1706. Similarly, the proximal cable 1804b extends from one of the rack gears 1706, wraps around a proximal pulley 1806b, and is attached to the opposing rack gear 1706. The cables 1804a,b can be made from a variety of materials including, but not limited to, a metal (e.g., tungsten, stainless steel, nitinol, etc.) a polymer (e.g., ultra-high molecular weight polyethylene), a synthetic fiber (e.g., KEVLAR®, VECTRAN®, etc.), an elastomer, or any combination thereof.

The coupled assembly of the rack gears 1706, the distal and proximal cables 1804a,b, and the distal and proximal pulleys 1806a,b completes or provides a cable loop, which allows the rack gears 1706 to operate in an antagonistic relationship where movement of one rack gear 1706 in one longitudinal direction can cause the other rack gear to move in the opposite direction and thereby manipulate the angular position of the distal structure 1802a (e.g., the end effector 1604 or the wrist 1806). In this example, selective actuation of the drive gears 1704 can cause the end effector 1604 (FIG. 16) to open or close, or may alternatively cause the wrist 1606 (FIG. 16) to articulate.

Figure 18A:
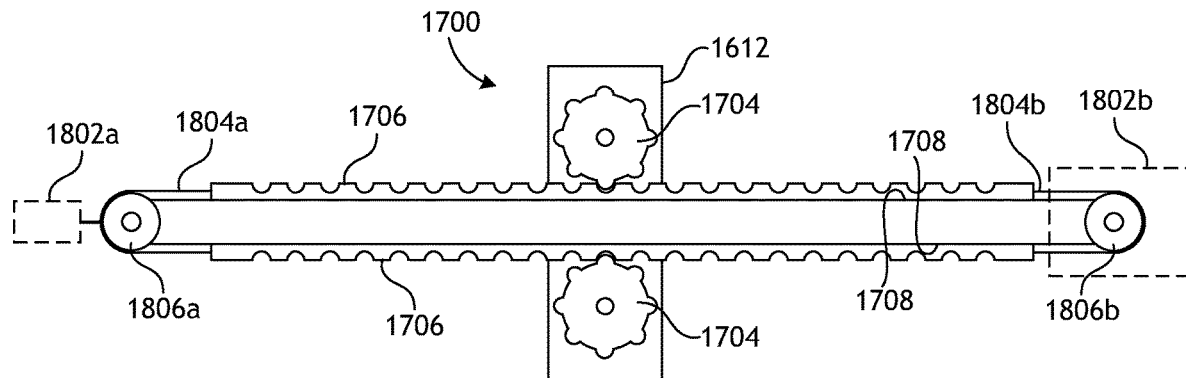
FIGS. 18A-18D are schematic diagrams of example operation of the actuation system of FIGS. 17A-17B, according to one or more embodiments.
Figure 18B:
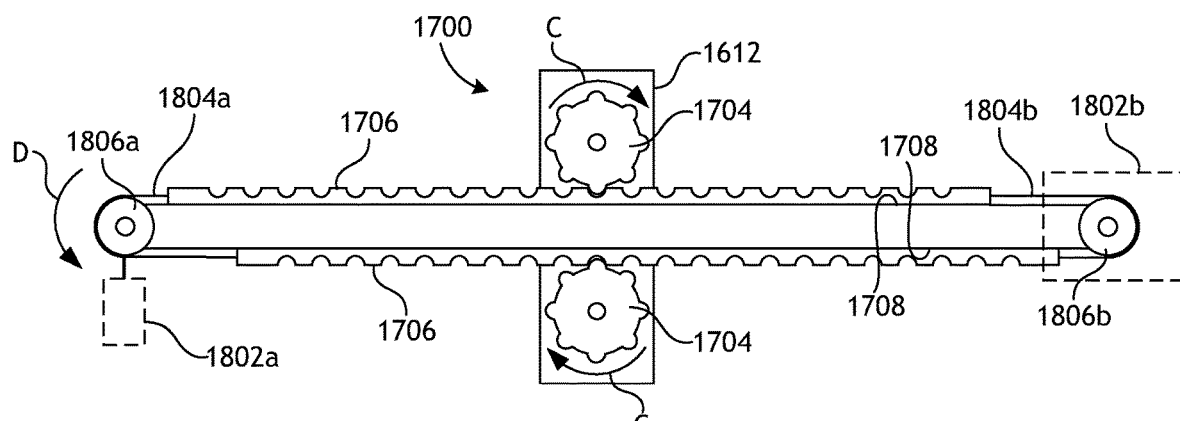

In FIG. 18B, for example, actuation (articulation) of the wrist 1606 may be accomplished by rotating the drive gears 1704 in the same direction, as indicated by the arrows C. This allows the rack gears 1706 to antagonistically operate and cause the distal structure 1802a to move (rotate) in the direction D. Alternatively, and depending on how the distal pulley 1806a is configured, rotating the drive gears 1704 in the same direction C may also cause one of the jaws 1608, 1610 (FIG. 16) of the end effector 1604 to open or close.

Figure 18C:
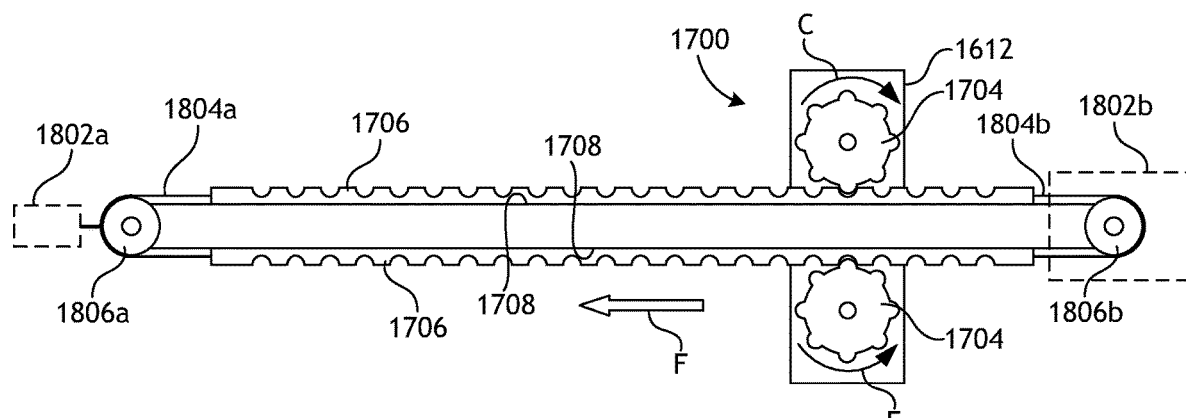

In FIG. 18C, axial movement of the shaft 1602 (e.g., insertion of the instrument) may be accomplished by rotating the drive gears 1704 in opposite directions, as shown by the arrows C and E. In this scenario, the shaft 1602 and the rack gears 1706 will be moved (translated) along its axis through the handle 1612 in the direction F. As will be appreciated, the configuration of the actuation system 1700 may be altered and otherwise modified to facilitate pitch, yaw, and jaw actuation of the distal structure 1802a.

This concept extends to more complicated wrists (e.g., the wrist 1606 of FIG. 16) that have more than one degree of freedom and follows N+1 rules where there are N+1 cables 1804a,b for N degrees of freedom in the wrist 1606. The handle 1612 would contain N+1 drive gears 1704 that each drive a rack gear 1706. The proximal structure 1802b at the proximal end of the shaft 1602 would also change to accommodate a wrist with more degrees of freedom. For instance, an example needle driver wrist may be driven by four cables 1804a,b, so the instrument would have four drive gears 1704 and four rack gears 1706. Additionally, this design could support more wrist concepts, such as a 2N wrist, and the proximal structure 1802b would have to change to appropriately mirror the wrist configuration.

Figure 18D:
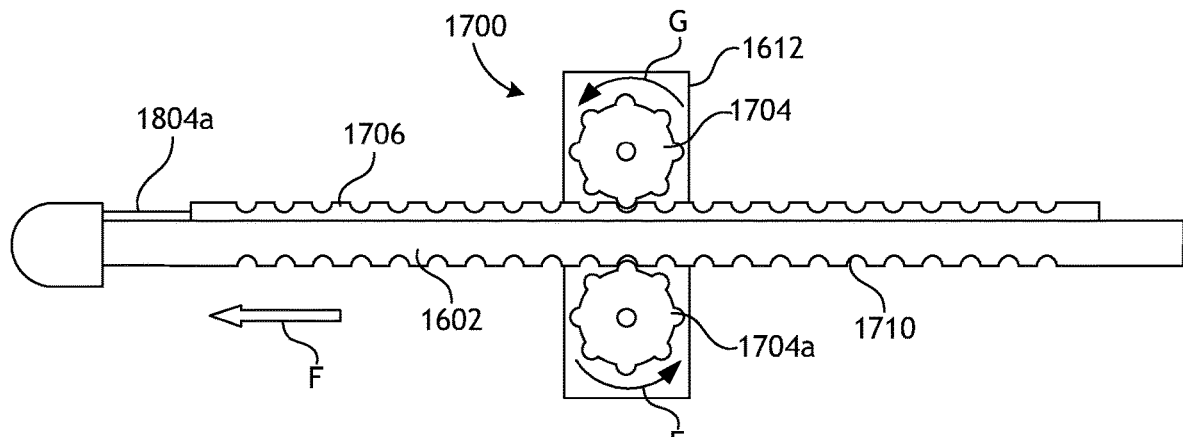

In FIG. 18D, the actuation system 1700 is shown with the shaft drive gear 1704a arranged to drive against the adjacent shaft rack gear 1710, where the teeth of the shaft rack gear 1710 are defined along all or a portion of the shaft 1602. In some embodiments, as discussed above, driving against the shaft rack gear 1710 will cause the shaft 1602 to move (translate) axially relative to (i.e., through) the handle 1612. In other embodiments, however, driving against the shaft rack gear 1710 may help adjust tension in the cables (e.g., the distal cable 1804a). More specifically, in order to facilitate on-robot tensioning, each of the drive gears 1704 (only one shown) may be rotated in the direction G, which places the distal cables 1804a (only one shown) in tension. The generated tension may then be resolved by actuating the shaft drive gear 1704a in the direction E, which urges the shaft 1602 in the direction F. Consequently, the insertion degree of freedom may also be used to place tension on the robot, and, theoretically, all backlash in the system is now taken up when the robot tensions the tool.

In this scenario, portions of the shaft 1602 and the shaft rack gear 1710 located distal to the handle 1612 (i.e., to the left of the handle 1612 in FIG. 18D) will be under load when the robot puts tension in the tool. More specifically, portions of the shaft 1602 distal to the handle 1612 will be in compression and portions of the rack gear 1706 distal to the handle 1612 will be in tension. The remaining portions of the shaft 1602 and the rack gear 1706 proximal to the handle 1612, however, will not be loaded. This is in contrast to cable-based surgical tool designs, where the loaded regions extend the entire length of the tool shaft with the cable in tension and the tool shaft in compression. Here, the actuation system 1700 results in a shorter loading path, which may be advantageous in generating smaller amounts of deflection at the wrist 1606 (FIG. 16) because the potential "spring" length is shorter. This may also result in the deflection length being dependent on the insertion length, but the input motion may be software adjusted based on the insertion length.

This architecture may further prove advantageous in removing backlash from insertion of the surgical tool 1600 (FIG. 16) and the sterile adaptor 1618 (FIG. 16). In this architecture, tension in the cables extending through the wrist 1606 (FIG. 16) may be able to react against the compressive load through the shaft 1602. This means that the gear trains located in the handle 1612 and the decoupler 1616 (FIG. 16) are all preloaded and all backlash in the decoupler 1616 and the surgical tool 1600 are removed. If the decoupler 1616 is located in the instrument driver 1614 (FIG. 16), however, the driver motors can be attached directly to the drive inputs provided on the decoupler 1616, all components between the wrist 1606 and the motors of the instrument driver 1614 are preloaded, and all backlash is theoretically eliminated.

Additionally, this architecture allows for more complicated components to be moved or designed into the instrument driver 1614 (FIG. 16). If the decoupler 1616 (FIG. 16) is integrated into the instrument driver 1614 or the sterile adaptor 1618 (FIG. 16), the surgical tool 1600 (FIG. 16) would contain fewer parts than a cable-differential design. As will be appreciated, this will help drive down the cost of the disposable component of the system, reduce manufacturing time, and lower the number of failure points in the instrument.

Figure 19:
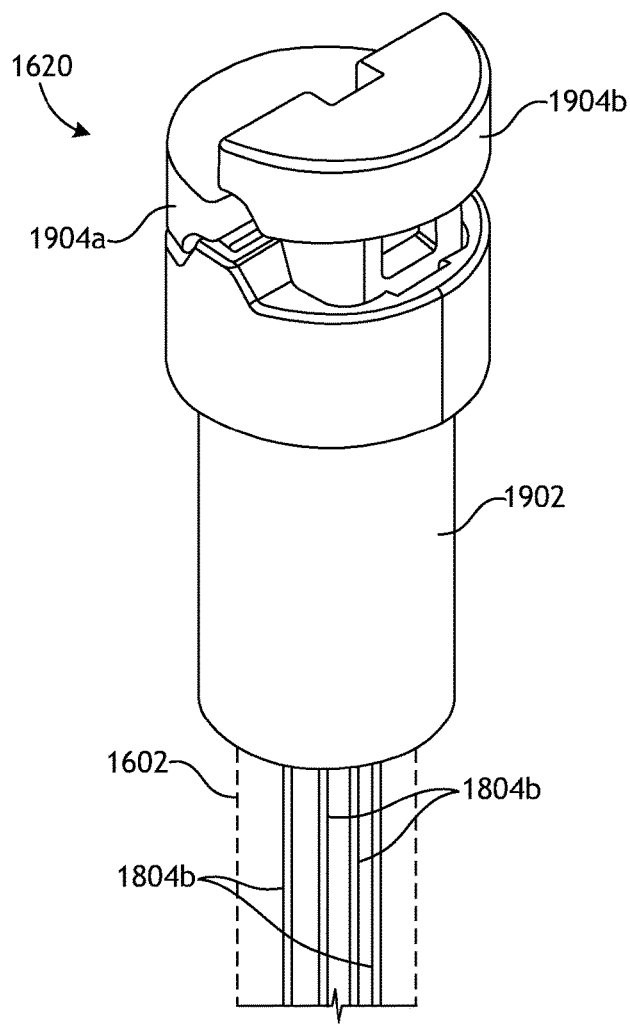
FIG. 19 is an isometric view of one example of the tailpiece of FIG. 16, according to one or more embodiments.

FIG. 19 is an isometric view of one example of the tailpiece 1620, according to one or more embodiments. As mentioned above, the tailpiece 1620 may be alternately referred to as a "pantograph" or "pantograph button," and may provide a means for maintaining tension in the surgical tool 1600 (FIG. 16) when the instrument is detached from the instrument driver 1614 (FIG. 16). The pantograph 1620 may additionally provide a way to manually control the end effector 1604 (FIG. 16) and/or the wrist 1606 (FIG. 16).

In the illustrated embodiment, the tailpiece 1620 includes a housing 1902 arranged at the distal end of the shaft 1602 (shown in dashed lines). A manual actuation device may be mounted to the housing 1902. In this embodiment, the manual actuation device includes first and second buttons 1904a and 1904b pivotably coupled to the housing 1902 and laterally offset from each other. Each button 1904a,b may be coupled to a corresponding one of the proximal cables 1804b. In the illustrated configuration, manipulation of the buttons 1904a,b may cause the jaws 1608, 1610 (FIG. 16) to open and close. More specifically, when the first button 1904a is depressed, the jaws 1608, 1610 open, and when the second button 1904b is depressed, the jaws 1608, 1610 close. The architecture of the pantograph 1620 could be altered, however, such that manipulation of the buttons 1904a,b may cause the wrist 1606 (FIG. 16) to articulate, without departing from the scope of the disclosure.

FIGS. 20A and 20B depict example operation of the tailpiece (pantograph) 1620 of FIG. 19, according to one or more embodiments. Each of FIGS. 20A-20B include two images of the pantograph 1620, the left image being a partial, cross-sectional view, and the right image including portions in phantom (dashed lines) to enable viewing of various internal components. As illustrated, the first and second buttons 1904a,b may be coupled to a toggle or "rocker" 2002 pivotably coupled to the housing 1902 such that pressing down on one button 1904a,b simultaneously causes the other button 1904a,b to pivot upward.

First and second proximal pulleys 2004a and 2004b may be rotatably mounted to the first and second buttons 1904a,b and are axially movable therewith during actuation of the pantograph 1620 and within the housing 1902. The proximal pulleys 2004a,b may be similar to the proximal pulley 1806b of FIGS. 18A-18C and thus have corresponding proximal cables 2006a and 2006b extending (wrapped) thereabout, where the proximal cables 2006a,b are similar to the proximal cable 1804b of FIGS. 18A-18C.

As mentioned above, the purpose of the pantograph 1620 is to maintain tension in the surgical tool 1600 (FIG. 16) when disconnected from the instrument driver 1614 (FIG. 16), but additionally, to provide a way to manually control the end effector 1604 (FIG. 16) and/or the wrist 1606 (FIG. 16). The pantograph 1620 ensures that cable length is conserved within the surgical tool 1600, which prevents the cables 2006a,b from derailing off the pulleys 2004a,b (also prevents the distal cables 1804a of FIGS. 18A-18C from derailing off the distal pulleys 1806a of FIGS. 18A-18C). The pantograph 1620 maintains tension in the surgical tool 1600 by completing the cable loops and conserving cable length.

In the illustrated embodiment, manually depressing the first button 1904a may cause the jaws 1608, 1610 (FIG. 16) to open, and manually depressing the second button 1904b may cause the jaws 1608, 1610 to close. The buttons 1904a,b are pivotably constrained together by the rocker 2002 such that if one button 1904a,b is pressed down, the opposite button 1904a,b correspondingly moves up with the same axial displacement. Moreover, since the pulleys 2004a,b are coupled to the buttons 1904a,b, as one button 1904a,b is pressed down, the corresponding pulley 2004a,b also moves down, and the opposing button 1904a,b and its corresponding pulley 2004a,b moves up with the same displacement. Consequently, the net cable length of the cables 2006a,b remains the same because the two pulleys 2004a,b have the same displacement, but the change in length of each pair changes, which causes movement of the jaws 1608, 1610.

Figure 21:
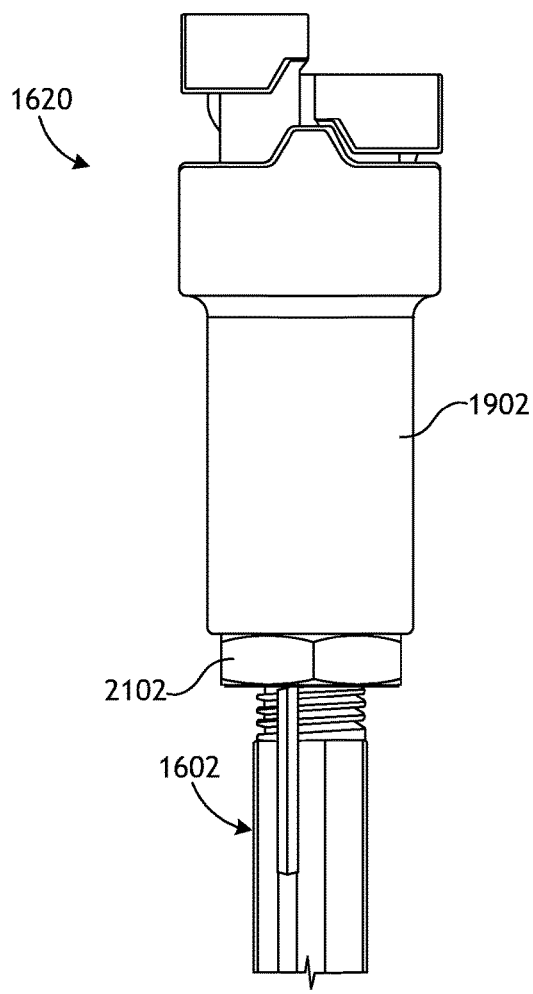
FIG. 21 is an enlarged side view of the tailpiece (pantograph) of FIG. 19, according to one or more embodiments.

FIG. 21 is an enlarged side view of the tailpiece (pantograph) 1620 of FIG. 19, according to one or more embodiments. The pantograph 1620 can also simplify the process of tensioning the surgical tool 1600 (FIG. 16). In the illustrated embodiment, for example, the housing 1902 is movably mounted to the shaft 1602 adjacent a tensioning nut 2102 threaded to the proximal end of the shaft 1602. Rotating the tensioning nut 2102 may apply an axial load on the bottom of the housing 1902, which may correspondingly extend the cable paths and thus tension the cables 2006a,b (FIGS. 20A-20B) in the system. Accordingly, pushing against the housing 1902 with the tensioning nut 2102 applies tension equally to all cables 1804a,b (FIGS. 18A-18C) in the system.

Figure 22:
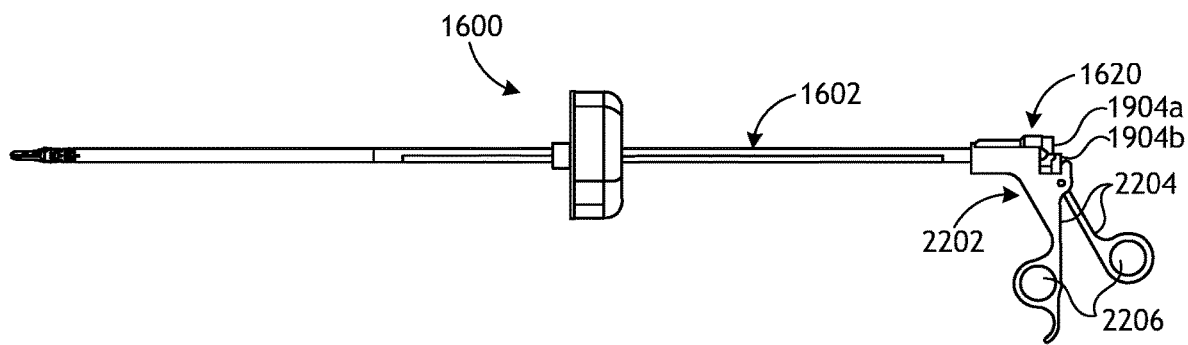
FIG. 22 is a side view of the surgical tool of FIG. 16, according to one or more additional embodiments.

FIG. 22 is a side view of the surgical tool 1600, according to one or more additional embodiments. The tailpiece (pantograph) 1620 arranged at the proximal end of the shaft 1602 may further prove advantageous in converting the surgical tool 1600 into a type of manual laparoscopic surgical tool. More specifically, a manual accessory 2202 may be mounted to or otherwise secured to the tailpiece 1620. In the illustrated embodiment, for instance, the manual accessory may include ergonomic features, such as opposing handles 2204 and finger holes 2206, that allow a user to operate the manual accessory 2202 and thereby manually operate at least one of the buttons 1904a,b to control the end effector 1604 (FIG. 16) or the wrist 1606 (FIG. 16). In at least one embodiment, the manual accessory 2202 may be used to lock the wrist 1606 so manual actuation of the pantograph 1620 only articulates the jaws 1608, 1610 (FIG. 16) open and closed.

Figure 23A:
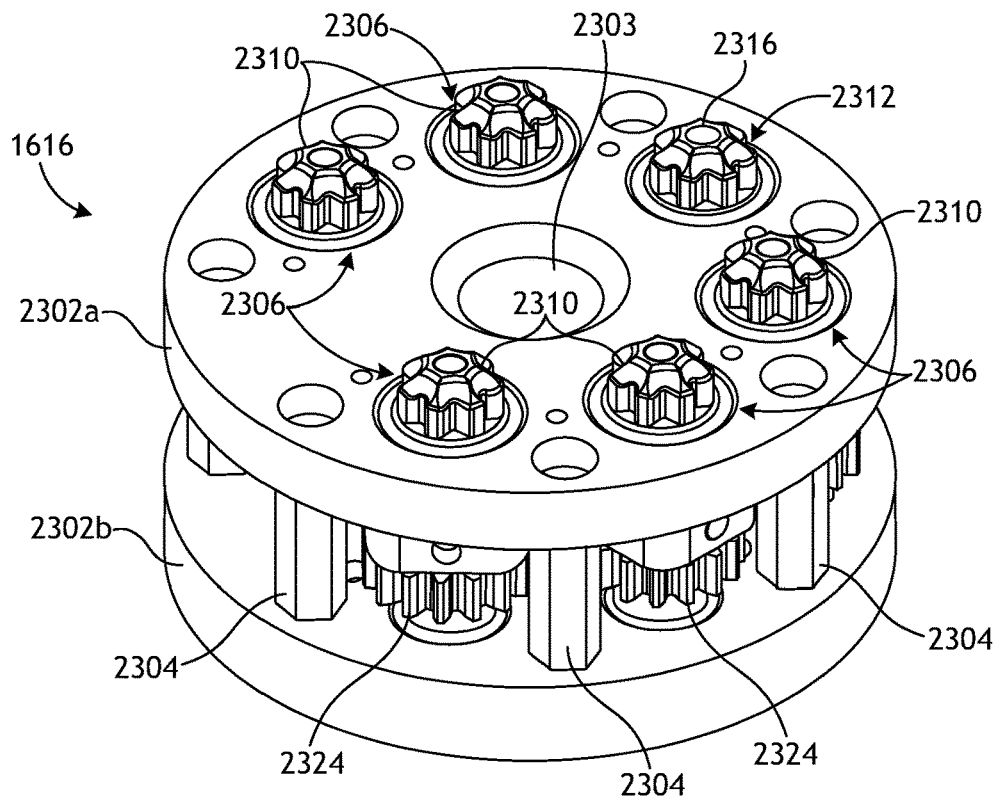
FIGS. 23A and 23B are isometric and bottom views, respectively, of one example of the decoupler of FIG. 16, according to one or more embodiments.
Figure 23B:
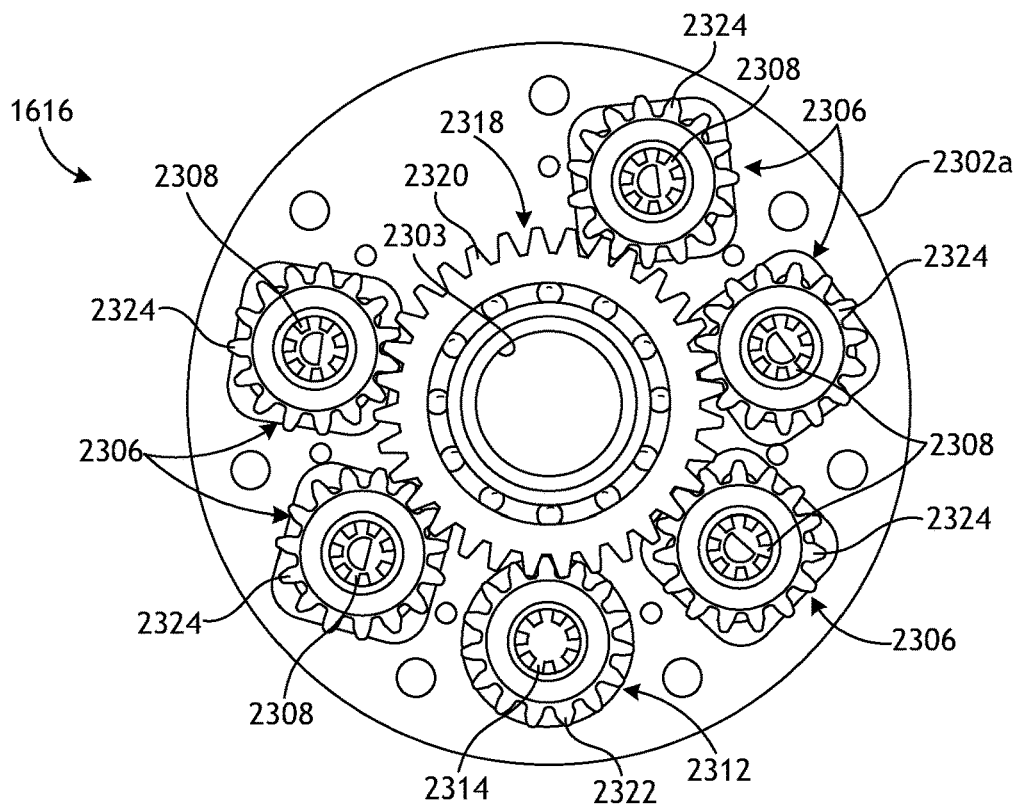

FIGS. 23A and 23B are isometric and bottom views, respectively, of one example of the decoupler 1616 of FIG. 16, according to one or more embodiments. As discussed above, the decoupler 1616 may interpose the handle 1612 (FIG. 16) and the instrument driver 1614 (FIG. 16), and may otherwise operate to transfer torque from the drive outputs of the instrument driver 1614 to the drive inputs of the handle 1612. The architecture of the decoupler 1616 further allows for the transfer of insertion motion (e.g., movement of the shaft 1602) to all the drive inputs of the handle 1612, thus allowing one robot motor from the instrument driver 1614 to control insertion of the surgical tool 1600, while allowing the other driver motors to drive the sliding rack gears independent of insertion.

As best seen in FIG. 23A, the decoupler 1616 may include a first or "upper" flange 2302a and a second or "lower" flange 2302b axially offset from the upper flange 2302a. Concentrically aligned central apertures 2303 are defined in each flange 2302a,b and through which the shaft 1602 (FIG. 16) can extend. The flanges 2302a,b may be operatively coupled with one or more columns 2304 that extend between the flanges 2302a,b. In FIG. 23B, the lower flange 2302b and the columns 2304 are omitted to enable viewing of the internal components of the decoupler 1616 from a bottom perspective.

The decoupler 1616 includes a plurality of differential assemblies 2306 rotatably mounted between the upper and lower flanges 2302a,b. While five differential assemblies 2306 are depicted in FIGS. 23A-23B, more or less than five may be included in the decoupler 1616, without departing from the scope of the disclosure. As best seen in FIG. 23B, each differential assembly 2306 includes a differential input 2308, which is matable with a corresponding one of the drive outputs of the instrument driver 1614 (FIG. 16); each motor in the instrument driver 1614 drives one of the differential assemblies 2306. As illustrated, each differential input 2308 may define a receptacle that defines splines, protrusions, or other structural features designed to mate with corresponding features of the drive outputs of the instrument driver 1614, or vice versa. Once properly mated, the differential inputs 2308 will share axes of rotation with the corresponding drive outputs of the instrument driver 1614 to allow the transfer of rotational torque from the drive output to the corresponding differential input 2308.

As best seen in FIG. 23A, each differential assembly 2306 may also include a differential output 2310, which is matable with a corresponding one of the drive inputs 1702 (FIGS. 17A-17B) of the actuation system 1700 (FIGS. 17A-17B). As illustrated, each differential output 2310 may define splines, protrusions, or other structural features designed to mate with corresponding receptacles of the drive inputs 1702, or vice versa. Once properly mated, the drive inputs 1702 will share axes of rotation with a corresponding differential output 2310 to allow rotational torque from the differential output 2310 to be transferred to the corresponding drive inputs 1702. Accordingly, once the decoupler 1616 is properly installed between the handle 1612 (FIG. 16) and the instrument driver 1614 (FIG. 16), the drive inputs 1702 will share axes of rotation with the corresponding drive outputs of the instrument driver 1614 (FIG. 16) via the decoupler 1616, which allows the transfer of rotational torque from the drive outputs to the corresponding drive inputs 1720.

The decoupler 1616 further includes an insertion assembly 2312 also rotatably mounted between the upper and lower flanges 2302a,b. As best seen in FIG. 23B, the insertion assembly 2312 includes an insertion input 2314, which is matable with a corresponding one of the drive outputs of the instrument driver 1614 (FIG. 16); referred to herein as the "shaft drive output". The insertion input 2314 may define a receptacle that defines splines, protrusions, or other structural features designed to mate with corresponding features of the corresponding drive output of the instrument driver 1614, or vice versa. Once properly mated, the insertion input 2314 will share an axis of rotation with the corresponding drive output of the instrument driver 1614 to allow the transfer of rotational torque from the drive output to the insertion input 2314.

As seen in FIG. 23A, the insertion assembly 2312 further includes an insertion output 2316, which is matable with a corresponding one of the drive inputs 1702 (FIGS. 17A-17B) of the actuation system 1700 (FIGS. 17A-17B); referred to herein as the "shaft drive input". As illustrated, the insertion output 2316 may define splines, protrusions, or other structural features designed to mate with a receptacle of a corresponding drive input 1702, or vice versa. Once properly mated, the insertion output 2316 will share an axis of rotation with the corresponding drive input 1702 to allow the transfer of rotational torque from the insertion output 2316 to the corresponding drive input 1702. Accordingly, once the decoupler 1616 is properly installed between the handle 1612 (FIG. 16) and the instrument driver 1614 (FIG. 16), the drive input 1702 mated to the insertion output 2316 will share an axis of rotation with the drive output of the instrument driver 1614 (FIG. 16) mated with the insertion input 2314 via the decoupler 1616, which allows the transfer of rotational torque from the drive output to the corresponding drive input 1720.

In the case of an insertion-coupled instrument, such as the surgical tool 1600 (FIG. 16), when the shaft 1602 (FIG. 16) is inserted or retracted, all the sliding rack gears 1706 (FIGS. 17A-17B and 18A-18D) need to move at the same rate to maintain the position of the wrist 1606 (FIG. 16). One solution to accomplish this may be to have the motors of the instrument driver 1614 (FIG. 16) jointly perform the coupled motion. In this solution, however, the power requirements for the motors increases because the performance of the surgical tool 1600 is based on maintaining a grip force and a tip velocity. If the motors were to drive in a coupled fashion, then the motors would have to move faster and still maintain the same force output. This is particularly difficult because the required insertion velocity is much higher than the velocity to drive the sliding rack gears 1706.

In contrast, the decoupler 1616 allows the surgical tool 1600 (FIG. 1) with coupled motions to be driven by uncoupled inputs. More specifically, the decoupler 1616 allows one motor from the instrument driver 1614 (FIG. 16) to control insertion of the surgical tool 1600 (i.e., axial movement of the shaft 1602 of FIG. 16) while simultaneously allowing the other motors of the instrument driver 1614 to drive the sliding rack gears 1706 (FIGS. 17A-17B and 18A-18D) independent of insertion. To accomplish this, the decoupler 1616 includes a differential gear train 2318, which can include a system of mechanically-linked differential sub-assemblies that allow the insertion input 2314 to simultaneously drive each differential output 2310 of the decoupler 1616, while also allowing each differential input 2308 to independently drive the corresponding differential output 2310.

As best seen in FIG. 23B, the differential gear train 2318 includes an insertion transmission gear 2320 that may be driven by an insertion input gear 2322 mounted to and otherwise forming part of the insertion assembly 2312. As the insertion assembly 2312 is driven (rotated), the insertion input gear 2322 drives against and causes the insertion transmission gear 2320 to rotate, and the insertion transmission gear 2320 is arranged to interface with a differential insertion input gear 2324 mounted to and otherwise forming part of each differential assembly 2306. As the insertion transmission gear 2320 drives against the differential insertion input gears 2324 simultaneously, each differential assembly 2306 correspondingly rotates. Accordingly, the insertion assembly 2312 is coupled to all the differential assemblies 2306 in the decoupler 1616 by a single gear; i.e., the insertion transmission gear 2320. Thus, when insertion is driven by operation (rotation) of the insertion assembly 2312, each of the differential assemblies 2306 is simultaneously rotated, which means that by driving the insertion input 2314, all the differential outputs 2310 simultaneously rotate. Additionally, if a motor input to any of the differential assemblies 2306 is rotated, then the corresponding differential output 2310 is simultaneously rotated. As will be appreciated, the result of this is the separation of the insertion motion from the motions (articulation) of the wrist 1606 (FIG. 16).

Figure 24:
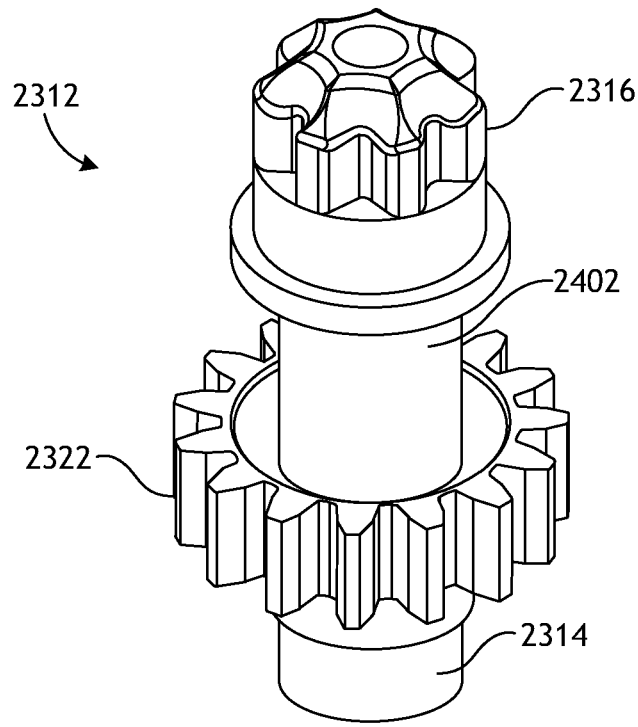
FIG. 24 is an isometric view of one example of the insertion assembly of FIGS. 23A-23B, according to one or more embodiments.

FIG. 24 is an isometric view of one example of the insertion assembly 2312, according to one or more embodiments. As illustrated, the insertion assembly 2312 includes a drive shaft 2402, and the insertion input 2314 is located at a first end of the drive shaft 2402 while the insertion output 2316 is located at a second (opposite) end of the drive shaft 2402. The insertion input gear 2322 is mounted to the drive shaft 2402 at a location between the insertion input and output 2314, 2316. In some embodiments, as illustrated, the insertion input and output 2314, 2316 and the insertion input gear 2322 may form an integral part of the drive shaft 2402, thus making the insertion assembly 2312 a monolithic part. In other embodiments, however, one or more of the insertion input and output 2314, 2316 and the insertion input gear 2322 may be coupled (fixed) to the drive shaft 2402, without departing from the scope of the disclosure.

Figure 25:
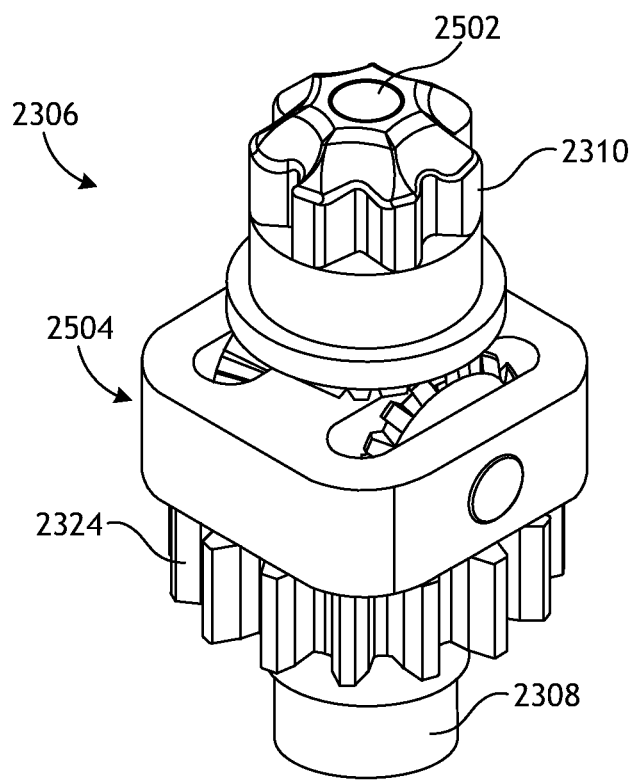
FIG. 25 is an isometric view of an example differential assembly of FIGS. 23A-23B, according to one or more embodiments.

FIG. 25 is an isometric view of an example differential assembly 2306, according to one or more embodiments. As illustrated, the differential assembly 2306 includes a drive shaft 2502, and the differential input 2308 is located at a first end of the drive shaft 2502 while the differential output 2310 is located at a second (opposite) end of the drive shaft 2502. The differential insertion input gear 2324 is mounted to or otherwise provided on the drive shaft 2502 at a location between the differential input 2308 and the differential output 2310.

The differential assembly 2306 may further include a differential 2504 also mounted to the drive shaft 2502 at a location between the differential input 2308 and the differential output 2310. The differential 2504 allows the differential output 2310 to be driven by the difference of two inputs; i.e., one from the differential input 2308 and another from the differential insertion input gear 2324 as driven by operation of the insertion assembly 2312 (FIGS. 23A-23B and 24).

FIGS. 26A-26C are side views of the differential assembly 2306 of FIG. 25 in various stages of deconstruction, according to one or more embodiments. In FIG. 26A, various parts of the differential assembly 2306 are shown in phantom (dashed lines) to enable viewing of various internal parts of the differential 2504. As illustrated, the differential 2504 may include a differential gear box or "carrier" 2602, a first or "upper" bevel gear 2604a, a second or "lower" bevel gear 2604b, and a pair of opposing side bevel gears or "carrier gears" 2606 extending between the upper and lower bevel gears 2604a,b.

The lower bevel gear 2604b operates as an input gear and may be secured to the drive shaft 2502 such that rotation of the drive shaft 2502 rotates the lower bevel gear 2604b and the differential output 2310. In some embodiments, the lower bevel gear 2604b may form part of the differential insertion input gear 2324, but may alternatively be nested within a portion of the differential insertion input gear 2324. The differential insertion input gear 2324, however, may nonetheless be able to drive rotation of the lower bevel gear 2604b, which drives rotation of the drive shaft 2502 and the differential output 2310 via interaction with the carrier gears 2606 and the upper bevel gear 2604a. The upper bevel gear 2604a operates as an output gear and may rotatably mounted to the drive shaft 2502 (i.e., free floating). While rotation of the lower bevel gear 2604b creates rotation input to the carrier 2602, the upper bevel gear 2604a rotates as a combination of rotation of the lower bevel gear 2604b and the carrier 2602. As the upper bevel gear 2604a rotates, the differential output 2310 correspondingly rotates.

An axle 2608 may be mounted to the carrier 2602, and the carrier gears 2606 may be rotatably mounted to the axle

2608. When the differential input 2308 is actuated, as discussed above, the drive shaft 2502 will rotate and correspondingly rotate the lower bevel gear 2604b and the differential output 2310. Rotation of the lower bevel gear 2604b will also drive against and cause the carrier gears 2606 to rotate about (on) the upper bevel gear 2604a, which results in rotation of the carrier 2602 while the upper bevel gear 2604a remains stationary. In contrast, however, when the differential insertion input gear 2324 is rotated via actuation of the insertion assembly 2312, the upper bevel gear 2604a will rotate and thereby cause the carrier gears 2606 to drive against the lower bevel gear 2604b, which correspondingly rotates the drive shaft 2502 and the differential output 2310. In this scenario, the carrier 2602 remains stationary. Accordingly, the differential 2504 may allow two inputs to create rotation of the differential output 2310. As will be appreciated, the insertion motion generated by the insertion assembly 2312 is transferred to all differential assemblies 2306 of the decoupler 1616.

While this design uses bevel gear differentials, those skilled in the art will readily appreciate that this same concept may be realized with any type of differential, such as a planetary or spur differential, which are described in more detail herein. Moreover, as mentioned above, the decoupler 1616 (FIGS. 23A-23B) could be integrated into the instrument driver 1614 1614 (FIG. 16). In such embodiments, the decoupler 1616 may be integrated into the gearbox of the motors of the instrument driver 1614 because the differentials can provide a gear reduction. This may require a redesign of the decoupler 1616 such that each motor of the instrument driver 1614 has two outputs. One would be the insertion-decoupled motion while the other is not, and the instrument driver 1614 would then be designed to selectively engage the appropriate outputs. One way to accomplish this is graphically depicted in FIGS. 27A and 27B.

Figure 27A:
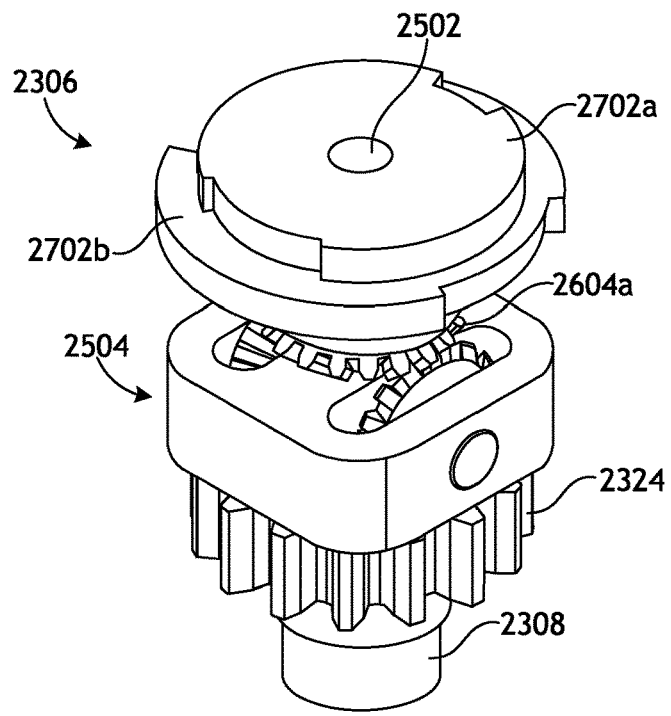
FIGS. 27A and 27B are isometric and cross-sectional side views, respectively, of another example differential assembly of FIG. 25, according to one or more additional embodiments.
Figure 27B:
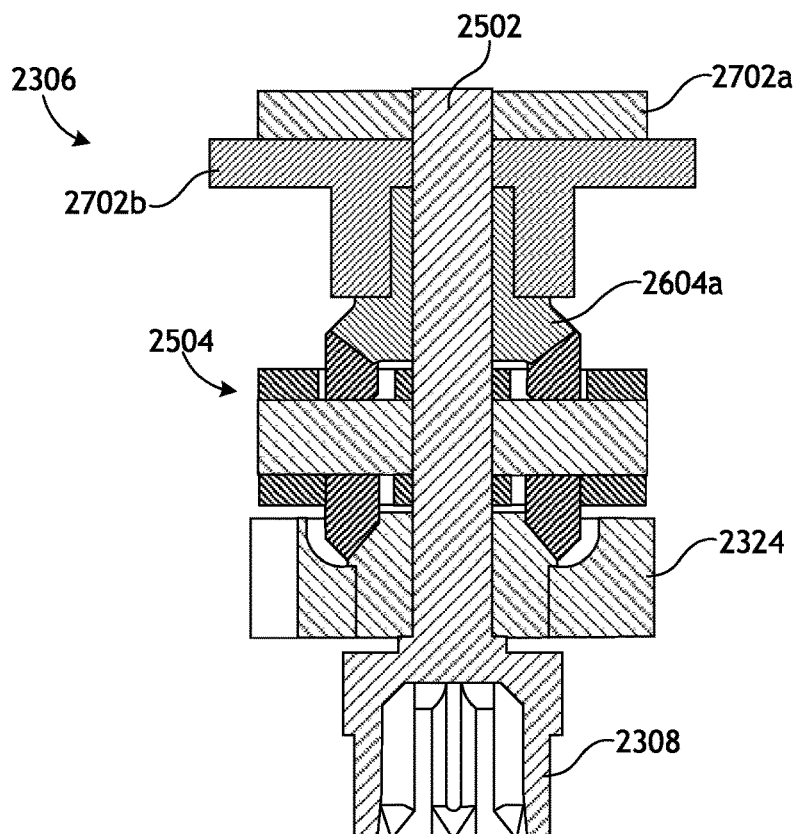

FIGS. 27A and 27B are isometric and cross-sectional side views, respectively, of another example differential assembly 2306, according to one or more additional embodiments. The differential assembly 2306 of FIGS. 27A-27B may be similar in some respects to the differential assembly 2306 of FIGS. 25 and 26A-26B, and therefore may be best understood with reference thereto, where like numerals will represent like components not described again in detail. As illustrated, for example, the differential assembly 2306 of FIGS. 27A-27B includes the drive shaft 2502, the differential input 2308 located at the first end of the drive shaft 2502, the differential insertion input gear 2324, and the differential 2504.

Unlike the differential assembly 2306 of FIGS. 25 and 26A-26C, however, the differential assembly 2306 of FIGS. 27A-27B may include first and second differential outputs 2702a and 2702b located at the second (opposite) end of the drive shaft 2502. The first and second differential outputs 2702a,b are coaxially aligned with each other and able to rotate independent of the other. More specifically, the first differential output 2702a is coupled to the drive shaft 2502 such that actuating the differential input 2308 drives the drive shaft 2502 and rotates the first differential output 2702a. In contrast, when the differential insertion input gear 2324 is rotated via actuation of the insertion assembly 2312 (FIGS. 23A-23B and 24), the differential 2504 operates to drive against the upper bevel gear 2604a, which correspondingly rotates the second differential output 2702b. In such embodiments, a corresponding drive input of the handle 1612 (FIG. 16) will be configured to engage with one of the differential outputs 2702a,b, while the other differential output 2702a,b is able to freely spin. This allows the instrument input design to determine which differential output 2702a,b is used.

Another solution could be a mechanism that uncouples the insertion assembly 2312 (FIGS. 23A-23B and 24) from the differential insertion input gears 2324 on each differential assembly 2306 then keeps the differential insertion input gears 2324 on all the differential assemblies 2306 stationary. With this setup, the differential assembly 2306 only has one input driving the differential output 2310, so they drive the differential output 2310 as normal. One design to execute this concept may be to have the insertion transmission gear 2320 (FIG. 23) on a shifter such that it could be selectively engaged or disengaged with the differential insertion input gears 2324 on each differential assembly 2306, and then lock the insertion transmission gear 2320. This design could be actuated by a single solenoid in the instrument driver 1614 (FIG. 16), for example.

Figure 28:
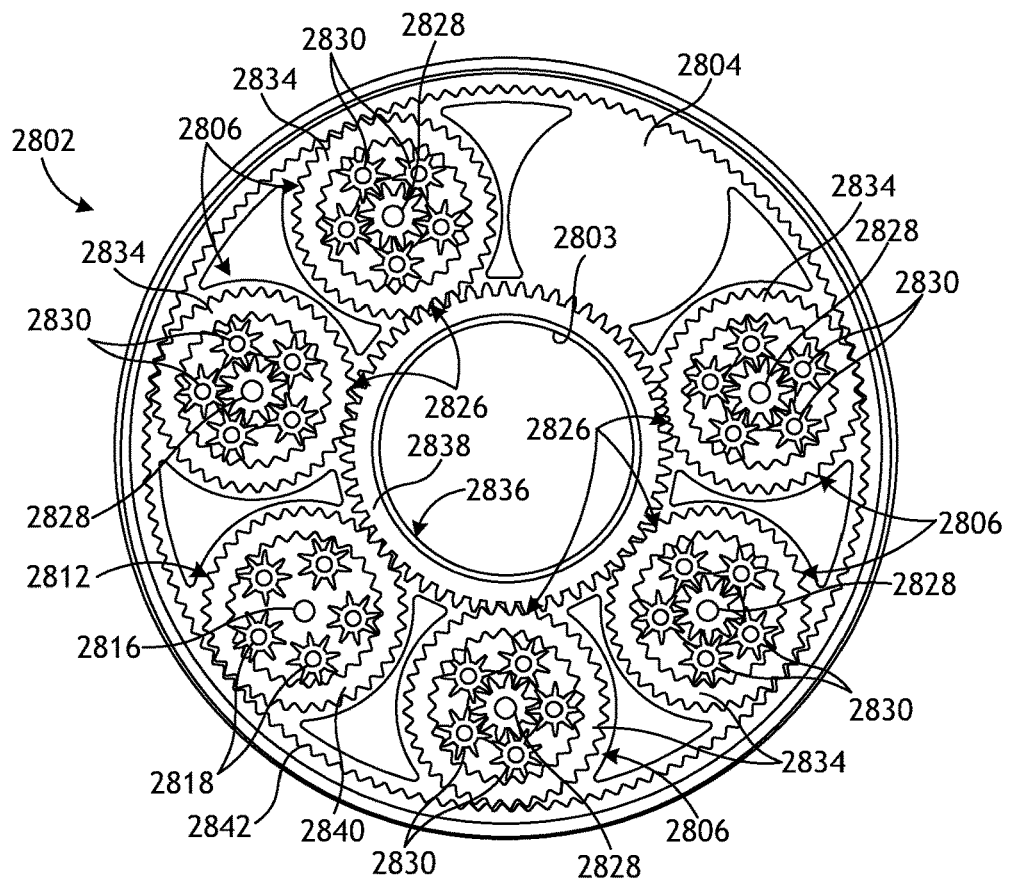
FIG. 28 is a top view of another example of the decoupler of FIG. 16, according to one or more additional embodiments.

FIG. 28 is a top, schematic view of another example decoupler 2802, according to one or more additional embodiments. The decoupler 2802 may be similar in some respects to the decoupler 1616 of FIGS. 23A-23B, and therefore may be best understood with reference thereto. Similar to the decoupler 1616, for example, the decoupler 2802 may be incorporated into the surgical tool 1600 (FIG. 16) and may be configured to interpose the instrument driver 1614 (FIG. 16) and the handle 1612 (FIG. 16). The decoupler 2802 may be operable to transfer torque from the drive outputs of the instrument driver 1614 to the drive inputs of the handle 1612. Moreover, the architecture of the decoupler 2802 further allows for the transfer of insertion motion (e.g., movement of the shaft 1602) to all the drive inputs of the handle 1612, thus allowing one robot motor from the instrument driver 1614 to control insertion of the surgical tool 1600, while allowing the other driver motors to drive the sliding rack gears independent of insertion. The decoupler 2802 defines a central aperture 2803 through which the shaft 1602 is able to extend and translate.

Unlike the decoupler 1616 of FIGS. 23A-23B, however, which incorporated a bevel gear differential design, the decoupler 2802 incorporates a planetary or epicyclic gearbox as the differential and primary axle driver. Those skilled in the art will appreciate that the specific design of the decoupler 2802 shown herein can allow for additional options to vary gear ratios and thereby augment load output for the cable drivers that may require higher loads. The decoupler 2802 may also prove beneficial in facilitating smaller packaging, which allows for a reduced overall height for the tool assembly and thereby improves internal reach for a common shaft.

As illustrated, the decoupler 2802 includes a housing 2804 and a plurality of differential assemblies 2806 are mounted to the housing 2804. While five differential assemblies 2806 are depicted in FIG. 28, more or less than five may be included in the decoupler 2802, without departing from the scope of the disclosure. On the bottom of the decoupler 2802, each differential assembly 2806 includes a differential input 2808 (see FIGS. 29, 31, and 32) matable with a corresponding one of the drive outputs of the instrument driver 1614 (FIG. 16); each motor in the instrument driver 1614 drives one of the differential assemblies 2806 via a corresponding one of the differential inputs 2808. Once properly mated, the differential input 2808 will share an axis of rotation with the corresponding drive output of the instrument driver 1614 to allow the transfer of rotational torque from the drive output to the corresponding differential input 2808.

Each differential assembly 2806 may also include a differential output 2810 (see FIGS. 29, 31, and 32), which is matable with a corresponding one of the drive inputs 1702 (FIGS. 17A-17B) of the actuation system 1700 (FIGS. 17A-17B). Once properly mated, the drive inputs 1702 will share axes of rotation with corresponding differential outputs 2810 to allow rotational torque from the differential output 2810 to be transferred to the corresponding drive input 1702. Accordingly, once the decoupler 2802 is properly installed between the handle 1612 (FIG. 16) and the instrument driver 1614 (FIG. 16), the drive inputs 1702 will share axes of rotation with the corresponding drive outputs of the instrument driver 1614 (FIG. 16) via the decoupler 2802, which allows the transfer of rotational torque from the drive outputs to the corresponding drive inputs 1720.

The decoupler 2802 further includes an insertion assembly 2812 also mounted to the housing 2804. The insertion assembly 2812 includes an insertion input 2814 (see FIGS. 33-34), which is matable with a corresponding one of the drive outputs of the instrument driver 1614 (FIG. 16); referred to herein as a "shaft drive output". Once properly mated, the insertion input 2814 will share an axis of rotation with the shaft drive output of the instrument driver 1614 to allow the transfer of rotational torque from the drive output to the insertion input 2814.

Figure 33:
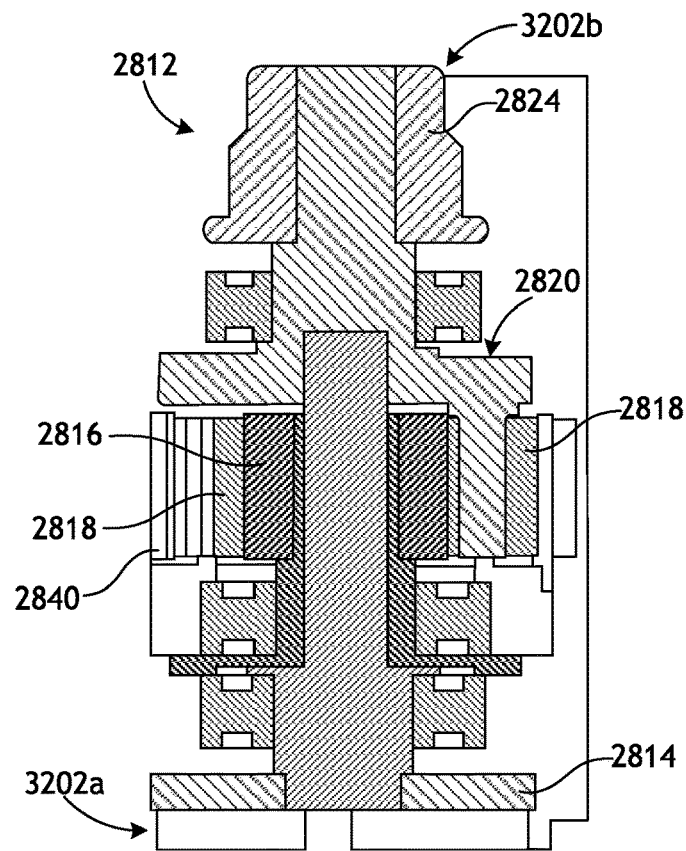
FIG. 33 is a cross-sectional side view of one example of the insertion assembly of FIG. 28, according to one or more embodiments.
Figure 34:
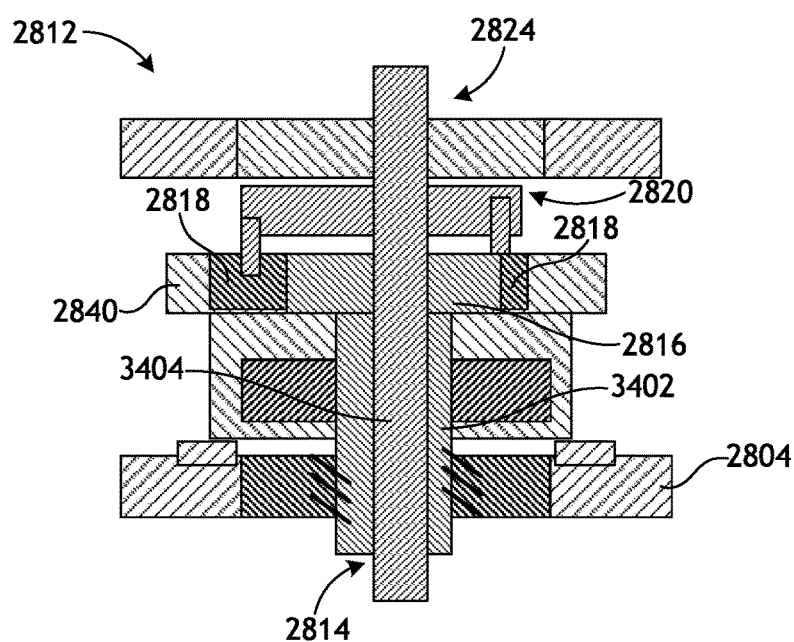
FIG. 34 is a schematic, cross-sectional side view of another example of the insertion assembly of FIG. 28, according to one or more additional embodiments.

In the illustrated embodiment, the insertion assembly 2812 is provided in the form of a planetary gear box, which includes a sun gear 2816 (see FIGS. 33-34), a plurality of planetary gears 2818 surrounding and intermeshed with the sun gear 2816, and a planet carrier 2820 (see FIGS. 33-34) coupled to each planetary gear 2818. As best seen in FIGS. 33-34, and in some embodiments, the planet carrier 2820 may form part of an insertion output 2824 matable with a corresponding one of the drive inputs 1702 (FIGS. 17A-17B) of the actuation system 1700 (FIGS. 17A-17B); referred to herein as the "shaft drive input". Once properly mated, the insertion output 2824 will share an axis of rotation with the corresponding shaft drive input 1702 to allow the transfer of rotational torque from the insertion output 2824 to the corresponding drive input 1702. Accordingly, once the decoupler 2802 is properly installed between the handle 1612 (FIG. 16) and the instrument driver 1614 (FIG. 16), the shaft drive input 1702 mated to the insertion output 2824 will share an axis of rotation with the shaft drive output of the instrument driver 1614 (FIG. 16) mated with the insertion input 2814 via the decoupler 2802. This allows the transfer of rotational torque from the shaft drive output of the instrument driver 1614 to the corresponding shaft drive input 1720.

Referring again to FIG. 28, each differential assembly 2806 may further include a differential 2826 that allows the differential output 2810 (FIGS. 29, 31, and 32) to be driven by the difference of two inputs; i.e., one from the differential input 2808 (FIGS. 29, 31, and 32) and another from the insertion assembly 2812. Similar to the insertion assembly 2812, each differential 2826 is provided in the form of a planetary gearbox, which includes a sun gear 2828, a plurality of planetary gears 2830 surrounding the sun gear 2828, and a planet carrier 2832 (see FIGS. 29-31) coupled to each planetary gear 2816. In some embodiments, as seen in FIGS. 31 and 32, the planet carrier 2832 may form part of the differential output 2810. Each differential 2826 may further include a differential ring gear 2834 surrounding and intermeshed with the planetary gears 2830. As described below, the differential ring gear 2834 may be driven by operation of the insertion assembly 2812, and thereby take into account insertion movement during operation.

Similar to the decoupler 1616 of FIGS. 23A-23B, the decoupler 2802 allows the surgical tool 1600 (FIG. 1) with coupled motions to be driven by uncoupled inputs. More specifically, the decoupler 2802 allows one motor from the instrument driver 1614 (FIG. 16) to control insertion of the surgical tool 1600 (i.e., axial movement of the shaft 1602 of FIG. 16) while simultaneously allowing the other motors of the instrument driver 1614 to drive the sliding rack gears 1706 (FIGS. 17A-17B and 18A-18D) independent of insertion. To accomplish this, the decoupler 2802 includes a differential gear train 2836, which can include a system of mechanically-linked differential sub-assemblies that allows the insertion input 2814 (see FIGS. 33-34) to simultaneously drive each differential output 2810 (see FIGS. 29, 31, and 32) of each differential assembly 2806, while also allowing each differential input 2808 (see FIGS. 29, 31, and 32) of each differential assembly 2806 to independently drive the corresponding differential output 2810.

In the illustrated embodiment, the differential gear train 2836 includes an insertion transmission gear 2838 and an insertion input gear 2840 arranged to drive the insertion transmission gear 2838. As illustrated, the insertion input gear 2840 surrounds and is intermeshed with the planetary gears 2818. As the insertion assembly 2812 is driven (rotated) to move the shaft 1602 (FIG. 16), the insertion input gear 2840 is simultaneously driven against and causes the insertion transmission gear 2838 to rotate. The insertion transmission gear 2838 is arranged to interface with (drive) the differential ring gear 2834 of each differential assembly 2806 such that each differential assembly 2806 correspondingly rotates.

Accordingly, the insertion assembly 2812 is coupled to the all the differential assemblies 2806 in the decoupler 2802 by a single gear; i.e., the insertion transmission gear 2838. Thus, when insertion is driven by operation (rotation) of the insertion assembly 2812, each of the differential assemblies 2806 is simultaneously rotated, which means that by driving the insertion input 2814 (FIGS. 33-34), all the differential outputs 2810 (FIGS. 29, 31, and 32) simultaneously rotate. Additionally, if a motor input to any of the differential assemblies 2806 is rotated, then the corresponding differential output 2810 is simultaneously rotated. As will be appreciated, the result of this is the separation of the insertion motion from the motions (articulation) of the wrist 1606 (FIG. 16).

In some embodiments, the differential gear train 2836 may further include a second insertion transmission gear 2842. In such embodiments, the first insertion transmission gear 2838 may be characterized as a central spur gear and the second insertion transmission gear 2842 may be characterized as an outer ring gear. The second insertion transmission gear 2842 may operate similar to the first differential gear 2838, in that the second insertion transmission gear 2842 may intermesh with and be driven via rotation of the insertion input gear 2840. Moreover, the second insertion transmission gear 2842 may be arranged to interface with the differential ring gear 2834 of each differential assembly 2806, and rotation of the second insertion transmission gear 2842 simultaneously drives against each differential ring gear 2834. In at least one embodiment, the first insertion transmission gear 2838 may be omitted and the differential gear train 2836 may only include the second insertion transmission gear 2842 to drive the differential ring gears 2834.

Figure 29:
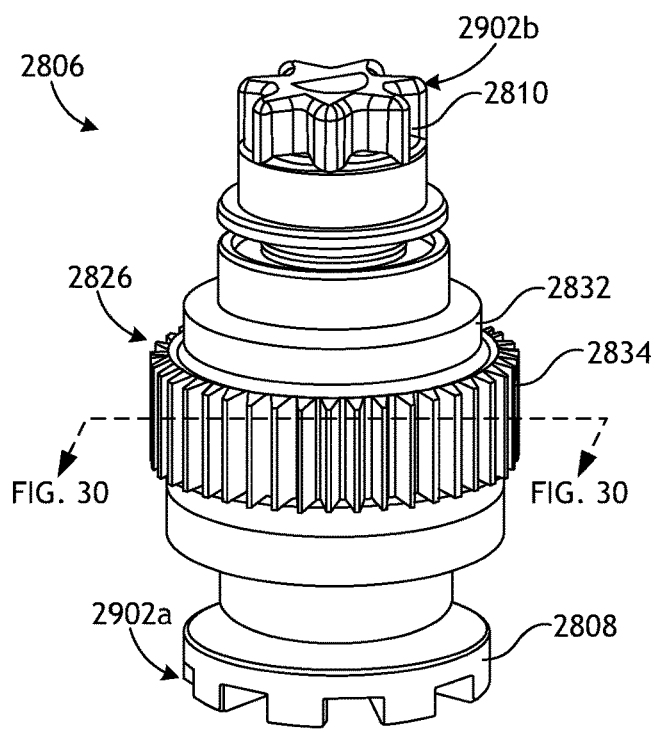
FIG. 29 is an isometric view of an example differential assembly.
Figure 30:
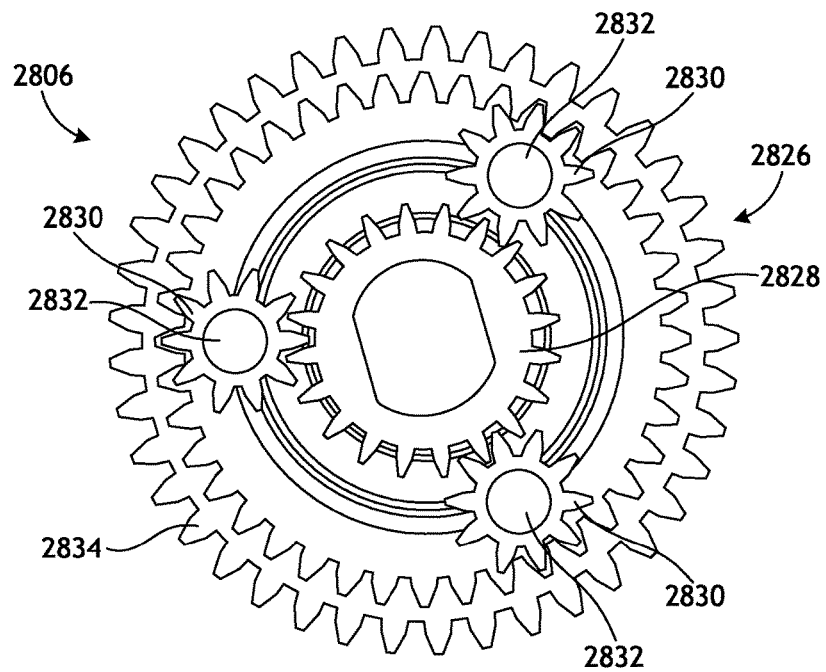
FIG. 30 is a cross-sectional top view of the differential assembly of FIG. 29 taken along the lines shown in FIG. 29.
Figure 31:
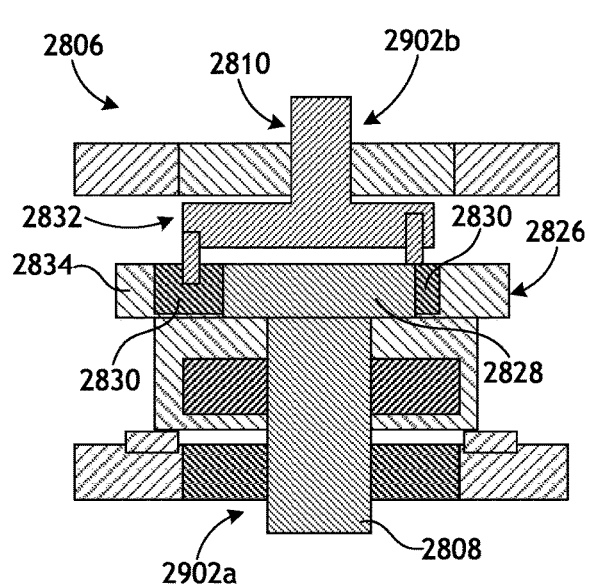
FIG. 31 is a schematic cross-sectional side view of the differential assembly of FIG. 29, according to one or more embodiments.
Figure 32:
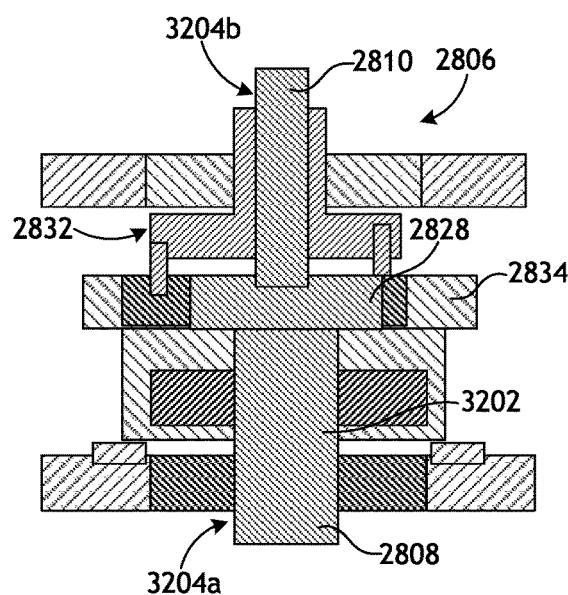
FIG. 32 is a schematic, cross-sectional side view of yet another example of the differential assembly of FIG. 28, according to one or more additional embodiments.

FIG. 29 is an isometric view of an example differential assembly 2806, FIG. 30 is a cross-sectional top view of the differential assembly 2806 taken along the lines shown in FIG. 29, and FIG. 31 is a schematic cross-sectional side view of the differential assembly 2806 of FIG. 29, according to one or more embodiments. As best seen in FIGS. 29 and 31, the differential assembly 2806 includes opposing first and second ends 2902a and 2902b. The differential input 2808 is located at the first end 2902a and is matable with a corresponding one of the drive outputs of the instrument driver 1614 (FIG. 16). As best seen in FIG. 29, the differential input 2808 may define a receptacle that defines splines, protrusions, or other structural features designed to mate with corresponding features of the drive outputs of the instrument driver 1614, or vice versa. The differential output 2810 is located at the second end 2902b and is matable with a corresponding one of the drive inputs 1702 (FIGS. 17A-17B) of the actuation system 1700 (FIGS. 17A-17B). As best seen in FIG. 29, the differential output 2810 may define splines, protrusions, or other structural features designed to mate with a corresponding receptacle of the drive input 1702, or vice versa.

The differential assembly 2806 also includes the differential 2826, which allows the differential output 2810 to be driven by both the differential input 2808 and the insertion assembly 2812 (FIG. 28). As best seen in FIGS. 30-31, the differential 2826 includes the sun gear 2828, the plurality of planetary gears 2830 surrounding the sun gear 2828, and the planet carrier 2832 coupled to each planetary gear 2830. In some embodiments, as shown in FIG. 31, at least a portion of the planet carrier 2832 may form part of the differential output 2810. The differential 2826 further includes the differential ring gear 2834, which surrounds and intermeshes with the planetary gears 2830 and is driven by the insertion transmission gear 2838 or 2842 (FIG. 28).

FIG. 32 is a schematic, cross-sectional side view of another example of the differential assembly 2806 of FIG. 28, according to one or more additional embodiments. In the illustrated embodiment, the differential assembly 2812 includes a drive shaft 3202 having opposing first and second ends 3204a and 3204b. The differential input 2808 is located at the first end 3404a and the differential output 2810 is located at the second end 3404b. The sun gear 2828 either forms part of the drive shaft 3202 or is fixed thereto such that rotation of the drive shaft 3202 correspondingly rotates the sun gear 2828. Moreover, the planet carrier 2832 may be coupled to the drive shaft 3202 such that rotation of the drive shaft 3202 correspondingly rotates the planet carrier 2832. Accordingly, the illustrated embodiment provides a non-coupled direct drive motion through the center of the differential assembly 2806. Those skilled in the art will readily appreciate that this may be done as an opportunity to drive a non-coupled actuator on a different instrument architecture.

FIG. 33 is a cross-sectional side view of one example of the insertion assembly 2812 of FIG. 28, according to one or more embodiments. As illustrated, the insertion assembly 2812 has opposing first and second ends 3202a and 3202b. The insertion input 2814 is provided at the first end 3202a, and the insertion output 2824 is provided at the second end 3202b. In some embodiments, as illustrated, the insertion input 2814 may define a receptacle that defines splines, protrusions, or other structural features designed to mate with corresponding features of a corresponding drive output of the instrument driver 1614 (FIG. 16), or vice versa. Similarly, in some embodiments, the insertion output 2824 define splines, protrusions, or other structural features designed to mate with a corresponding receptacle of a drive input 1702 (FIG. 17), or vice versa.

The insertion assembly 2812 further includes the sun gear 2816, the planetary gears 2818 surrounding and intermeshed with the sun gear 2816, and the planet carrier 2820 coupled to each planetary gear 2818. In at least one embodiment, the planet carrier 2820 may extend into and otherwise form part of the insertion output 2824. The insertion assembly 2812 also includes the insertion input gear 2840 operable to drive the insertion transmission gear 2838 (FIG. 28).

FIG. 34 is a schematic, cross-sectional side view of another example of the insertion assembly 2812 of FIG. 28, according to one or more additional embodiments. In the illustrated embodiment, the sun gear 2816 may include a distally extending extension 3402 that is keyed (fixed) to the housing 2804 of the decoupler 2802 (FIG. 28) at or near the insertion input 2814. Moreover, the insertion drive for the insertion assembly 2812 may be linked directly to the bottom of the planet carrier 2820. More specifically, the planet carrier 2820 may be mounted to a drive shaft 3404 that extends along the axial length of the insertion assembly 2812. The insertion input 2814 may be provided at one end of the drive shaft 3404, and the insertion output 2824 may be provided at the opposing end of the drive shaft 3404. Accordingly, instead of the insertion axis just having a gear on it, in the illustrated embodiment, the insertion axis directly drives the insertion output 2824 via rotation of the drive shaft 3404 and the planet carrier 2820; i.e., insertion directly drives the output.

Actuation of the insertion input 2814 simultaneously drives the planet carrier 2820, which drives the planetary gears 2818 against the insertion input gear 2840. This ensures that the rotation of the insertion axis is scaled to the correct output that occurs at each individual axis of the differential assemblies 2806 (FIGS. 28-31), without having to pair uneven gear ratios. Moreover, each rotation of the planet carrier 2820 drives the shaft rack gear 1710 (FIG. 17A) on the shaft 1602 (FIGS. 16 and 17A), while simultaneously rotating the insertion input gear 2840. As the insertion input gear 2840 rotates, it drives rotation of the insertion transmission gear 2838 (FIG. 28) and/or the second insertion transmission gear 2842 (FIG. 28). This motion then acts on the differential 2826 (FIG. 28) of each differential assembly 2806 (FIG. 28), which rotation is summed with the sun drive motion of each differential assembly 2806 to obtain a total output planet carrier motion at the individual differential assemblies 2806.

Figure 35A:
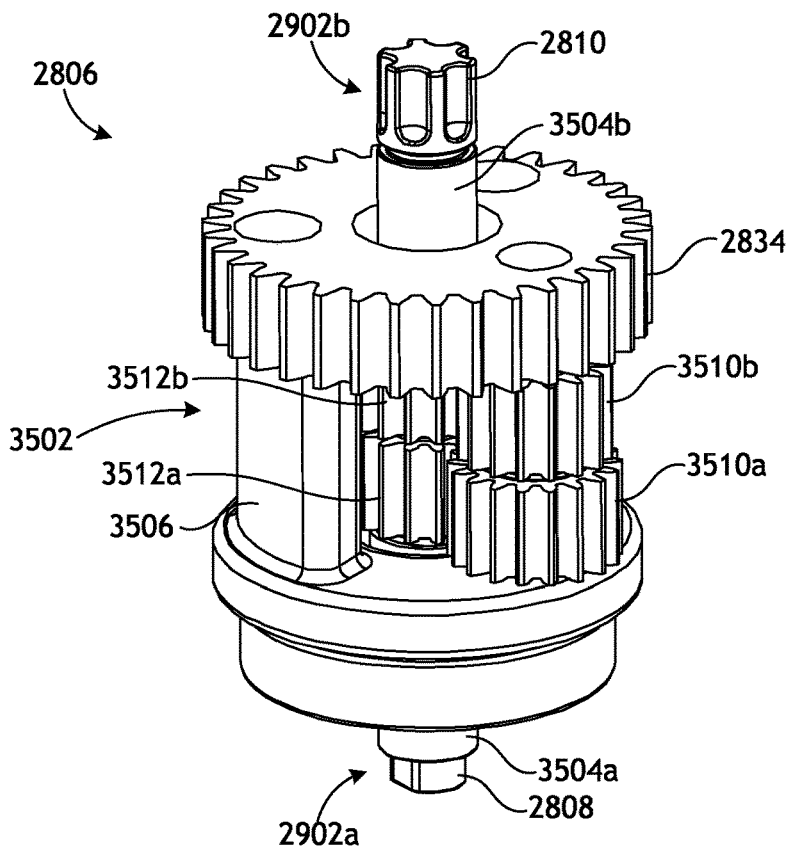
FIGS. 35A and 35B are isometric and cross-sectional side views of another example of the differential assembly of FIG. 28, according to one or more additional embodiments.
Figure 35B:
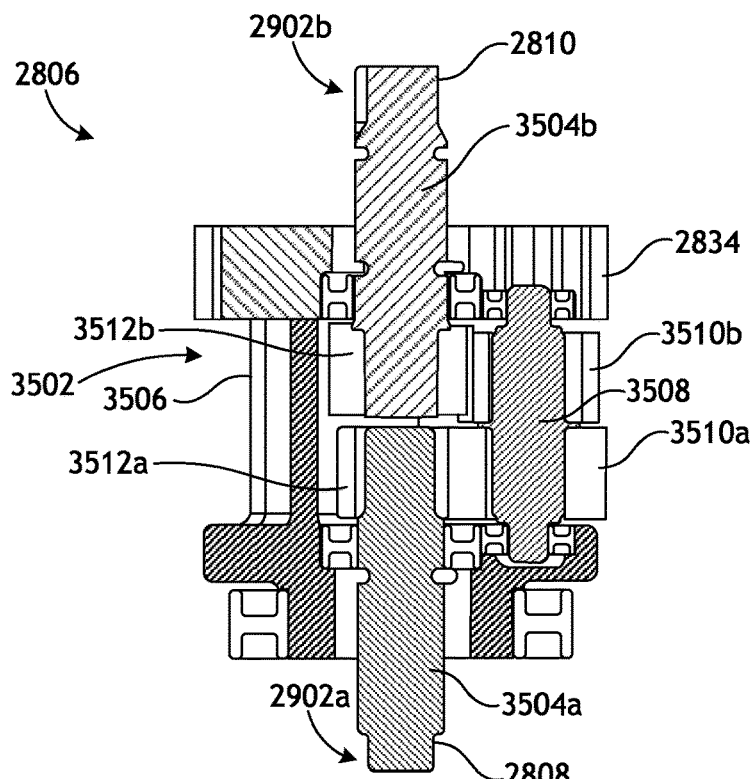

FIGS. 35A and 35B are isometric and cross-sectional side views of another example of the differential assembly 2806 of FIG. 28, according to one or more additional embodiments. Similar to the differential assembly 2806 shown in FIGS. 29-31, the differential assembly 2806 in FIGS. 35A-35B includes opposing first and second ends 2902a and 2902b, where the differential input 2808 is located at the first end 2902a and the differential output 2810 is located at the second end 2902b. Moreover, the differential assembly 2806 further includes the differential ring gear 2834, which is driven by the insertion transmission gear 2838 or 2842 (FIG. 28).

Unlike the differential assembly 2806 of FIGS. 29-31, however, where the differential 2826 was provided in the form of a planetary gearbox, the differential assembly 2806 of FIGS. 35A-35B includes a differential 3502 in the form of an offset axle gearbox. At least one advantage to the offset axle gearbox is that it can achieve a more ideal gear ratio (closer to 1:1) while limiting the height of the overall differential mechanism.

As illustrated, the differential 3502 includes an input shaft 3504a and an output shaft 3504b, where the input and output shafts 3504a,b are axially aligned and extend between the first and second ends 2902a,b. The differential input 2808 either forms part of or is coupled to the input shaft 3504a, and the differential output 2810 either forms part of or is coupled to the output shaft 3504b.

The differential 3502 further includes a housing 3506, and an offset axle 3508 (FIG. 35B) extends between the housing 3506 and the differential ring gear 2834. The offset axle 3508 extends parallel to but eccentric from the input and output shafts 3504a,b. A first offset gear 3510a is coupled to the offset axle 3508 and arranged to engage an input shaft gear 3512a mounted to the input shaft 3504a, and a second offset gear 3510b is coupled to the offset axle 3508 and arranged to engage an output shaft gear 3512b mounted to the output shaft 3504a.

The differential 3502 allows the differential output 2810 to be driven by both the differential input 2808 and the insertion assembly 2812 (FIG. 28). More specifically, rotating the differential input 2808 will cause the input shaft 3504a and the input shaft gear 3512a to rotate, which will drive against the first offset gear 3510a and thereby cause the offset axle 3508 and the second offset gear 3510b to drive against the output shaft gear 3512b, thus resulting in rotation of the output shaft 3504b and the differential output 2810. In contrast, rotating the differential ring gear 2834, as driven by the insertion transmission gear 2838 or 2842 (FIG. 28), will cause the offset axle 3508 and the housing 3506 to rotate about the input and output shafts 3504a,b, and thus driving the second offset gear 3510b against the output shaft gear 3512b and resulting in rotation of the output shaft 3504b and the differential output 2810. In such a scenario, the motor driving the differential input 2808 and the input shaft 3504a may be static or operating.

The differential 3502 shown in FIGS. 35A-35B is closer to 1.2:1 ratio. Utilizing a true 1:1 ratio through this gearbox would have the first and second offset gears 3510a,b of equal size, which for this configuration of differential 3502 would create a unique singularity wherein the motion of the differential 3502 would translate only to rotation of the offset axle 3508, and not the intended motion of the output shaft 3504b and the differential output 2810.

Figure 36A:
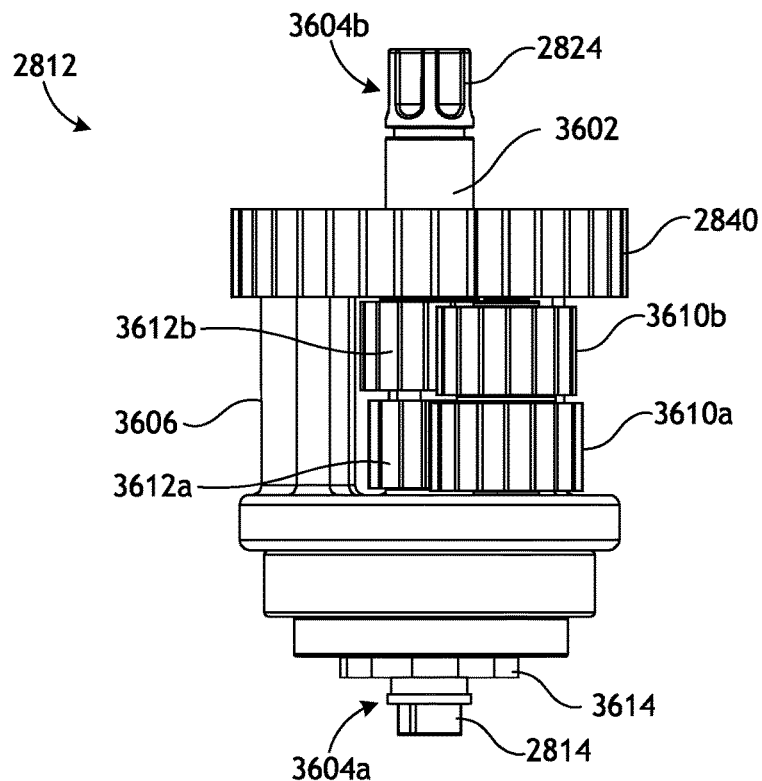
FIGS. 36A and 36B are isometric and cross-sectional side views, respectively, of another example of the insertion assembly of FIG. 28, according to one or more additional embodiments.
Figure 36B:
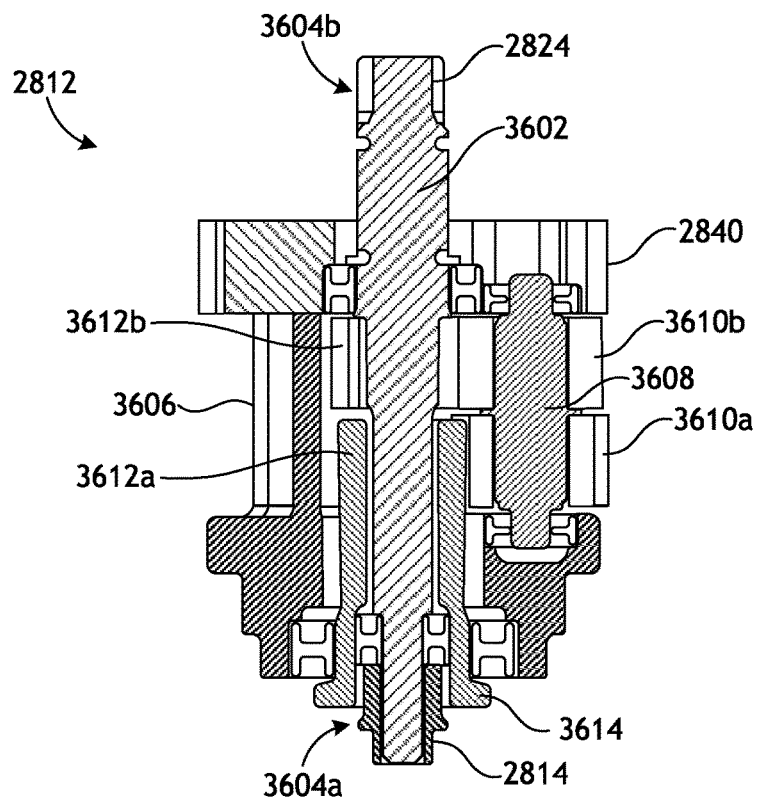

FIGS. 36A and 36B are isometric and cross-sectional side views, respectively, of another example of the insertion assembly 2812 of FIG. 28, according to one or more additional embodiments. The insertion assembly 2812 of FIGS. 36A-36B may be similar in some respects to the insertion assembly 2812 of FIGS. 33-34, and thus may be best understood with reference thereto, where like numerals will refer to similar components. As illustrated, the insertion assembly 2812 includes a drive shaft 3602 that has opposing first and second ends 3604a and 3604b. The insertion input 2814 is provided at the first end 3604a, and the insertion output 2824 is provided at the second end 3604b. Moreover, the insertion assembly also includes the insertion input gear 2840, which is arranged to drive the insertion transmission gear 2838 (FIG. 28) to enable simultaneous driving of each differential ring gear 2834 (FIG. 28) of each differential assembly 2806 (FIG. 28), as discussed above.

Unlike the insertion assembly 2812 of FIGS. 23-34, however, which included a planetary gearbox, the insertion assembly 2812 of FIGS. 36A-36B includes an offset axle gearbox. More specifically, the insertion assembly 2812 includes a housing 3606, and an offset axle 3608 (FIG. 36B) extends between the housing 3606 and the insertion input gear 2840. The offset axle 3608 extends parallel to but eccentric from the drive shaft 3602. A first offset gear 3610a is coupled to the offset axle 3608 and arranged to engage a stationary gear 3612a forming part of a stationary structure 3614 through which the drive shaft 3602 extends. The stationary structure 3614 may be keyed into the housing 3606, such as through a hex head mating engagement or the like. A second offset gear 3610b is coupled to the offset axle 3608 and arranged to engage a drive shaft gear 3612b mounted to the drive shaft 3602.

In example operation, rotating the insertion input 2814 will cause the drive shaft 3602 to rotate, which will cause insertion of the tool. Rotating the drive shaft 3602, however, will also cause the offset axle 3608 and the housing 3606 to rotate about the stationary structure 3614, which drives the insertion input gear 2840 in rotation. As discussed herein, rotating the insertion input gear 2840 drives the insertion transmission gear 2838 (FIG. 28) and thereby enables simultaneous driving of each differential ring gear 2834 (FIG. 28) of each differential assembly 2806 (FIG. 28). Accordingly, the insertion assembly 2812 of FIGS. 36A-36B ensures that all rotation of the insertion axis output (i.e., the drive shaft 3602) is simultaneously transferred to the differential assemblies 2806 at the inverted rate of the other gearboxes. Thus, when the motion is converted from a given differential assembly 2806 to its output 2810, the output rotation is equal to that of insertion. In some embodiments, to accomplish this, the same size offset gears 3510a,b (FIGS. 35A-35B) and 3610A,B may be used.

Figure 37:
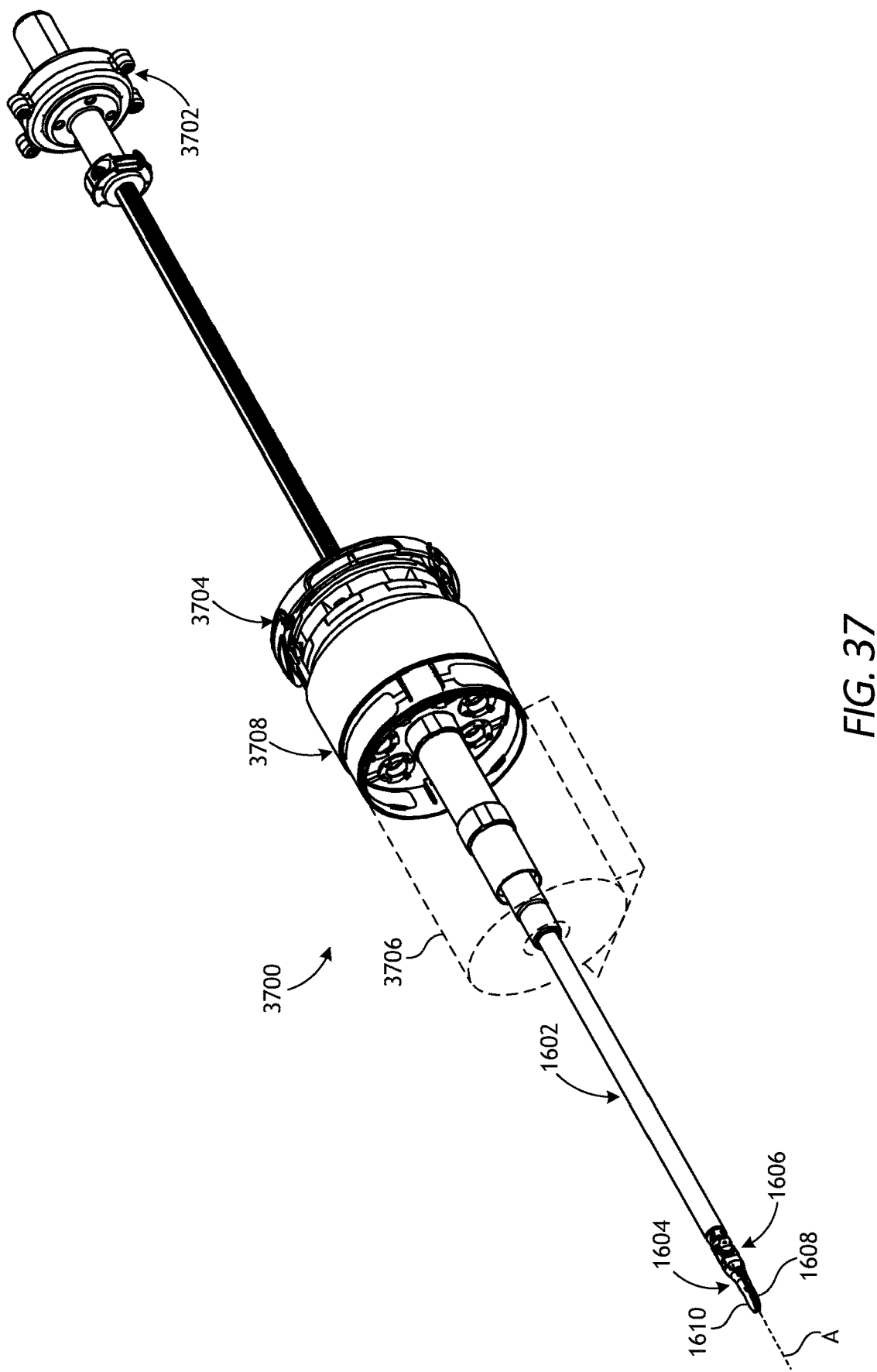
FIG. 37 is an isometric view of another example surgical tool that may incorporate some or all of the principles of the present disclosure.

FIG. 37 is an isometric view of another example surgical tool 3700 that may incorporate some or all of the principles of the present disclosure. The surgical tool 3700 may be similar in some respects to the surgical tool 1600 of FIG. 16 and therefore may be best understood with reference thereto, where like numerals correspond to similar components or structures not described again in detail. Similar to the surgical tool 1600, for example, the surgical tool 3700 includes the elongated shaft 1602, the end effector 1604 arranged at the distal end of the shaft 1602, and the articulable wrist 1606 that interposes and couples the end effector 1604 to the distal end of the shaft 1602. Moreover, a tailpiece 3702 may be arranged at a proximal end of the shaft 1602.

The surgical tool 3700 may include a drive housing or "handle" 3704 similar in some respects to the handle 1612 of FIG. 16. The shaft 1602 extends longitudinally through the handle 3704, and the handle 3704 houses an actuation system designed to facilitate articulation of the wrist 1606, actuation (operation) of the end effector 1604 (e.g., clamping, firing, rotation, articulation, energy delivery, etc.), and movement of the shaft 1602 relative to (through) the handle 3704 and along the longitudinal axis $A_1$. The actuation system may be the same as or similar to the actuation system 1700 of FIGS. 17A-17B, but could alternatively be another type of actuation system.

The handle 3704 may be operatively coupled to an instrument driver 3706 (shown in dashed lines) of a robotic surgical system. The instrument driver 3706 may be the same as or similar to the instrument driver 1614 of FIG. 16, and therefore may be best understood with reference thereto. Similar to the instrument driver 1614, for example, the instrument driver 3706 may be mounted to or otherwise positioned at the end of a robotic arm (not shown) and is designed to provide the motive forces required to operate the surgical tool 3700.

The handle 3704 includes a plurality of rotatable drive inputs (not visible) that can be driven by a corresponding plurality of drive outputs (not visible) of the instrument driver 3706. Each drive input is actuatable to independently drive (actuate) various portions of the actuation system housed within the handle 3704 and thereby operate the surgical tool 3700. Movement (rotation) of a given drive output correspondingly moves (rotates) the associated drive input and thereby operates the surgical tool 3700. Actuation of the drive inputs operates the actuation system, which can cause the end effector 1604 to articulate and/or actuate (operate) and the shaft 1602 to axially move (translate) relative to the handle 3704.

In the illustrated embodiment, a decoupler subassembly or "decoupler" 3708 is arranged between and otherwise interposes the handle 3704 and the instrument driver 3706. The decoupler 3708 may be the same as or similar in some respects to the decouplers 1616, 2802 of FIGS. 16 and 28, respectively. Similar to the decouplers 1616, 2802, for example, the decoupler 3708 transfers torque from the drive outputs of the instrument driver 3706 to the drive inputs of the handle 3704. Once the drive outputs are operatively and indirectly coupled to corresponding drive inputs via the decoupler 3708, the drive inputs will share axes of rotation with the corresponding drive outputs to allow the transfer of rotational torque from the drive outputs to the corresponding drive inputs, thus being able to operate the handle 3704. The decoupler 3708 may also be advantageous in transferring insertion motion (e.g., movement of the shaft 1602) to all the drive inputs, thus allowing one robot motor to control insertion of the surgical tool 3700, while allowing the other motors of the instrument driver 3706 to drive the sliding rack gears independent of insertion.

FIG. 38 depicts separated isometric end views of the instrument driver 3706 and the surgical tool 3700 of FIG. 37. With the jaws 1608, 1610 closed, the shaft 1602 and the end effector 1604 can penetrate the instrument driver 3706 by extending through a central aperture 3802 defined longitudinally through the instrument driver 3706 between first and second ends 3804a,b. A drive interface 3806 is provided at the first end 3804a of the instrument driver 3706 and is matable with a driven interface 3808 provided on the distal end of the handle 3704 and, more particularly, the distal end (bottom) of the decoupler 3708. The drive and driven interfaces 3806, 3808 may be configured to mechanically, magnetically, and/or electrically couple the handle 3704 (e.g., the decoupler 3708) to the instrument driver 3706.

The instrument driver 3706 includes a plurality of drive outputs 3810 that extend through the drive interface 3806. In embodiments where the surgical tool 3700 includes the decoupler 3708, the drive outputs 3810 are configured to mate with corresponding differential inputs 3812 provided at the distal end of the decoupler 3708. At least one of the differential inputs 3812 may be an insertion input 3814 operable to facilitate axial translation of the shaft 1602. The number of drive outputs 3810 will generally be the same as the number of differential and insertion inputs 3812, 3814, but it is contemplated herein that the instrument driver 3706 can have additional drive outputs, without departing from the scope of the disclosure.

The drive outputs 3810 may define splines, protrusions, or other mechanical features designed to mate with corresponding receptacles of the differential and insertion inputs 3812, 3814, or vice versa. One of the drive outputs 3810 may be configured to mate with the insertion input 3814, this drive output 3810 is referred to herein as a "shaft drive output." Once properly mated, the differential and insertion inputs 3812, 3814 will share axes of rotation with the corresponding drive outputs 3810 to allow the transfer of rotational torque from the drive outputs 3810 to the corresponding differential inputs 3812, 3814. In some embodiments, each drive output 3810 may be spring loaded and otherwise biased to spring outwards away from the drive interface 3806. Each drive output 3810 may be capable of partially or fully retracting into the drive interface 3806.

Figure 39A:
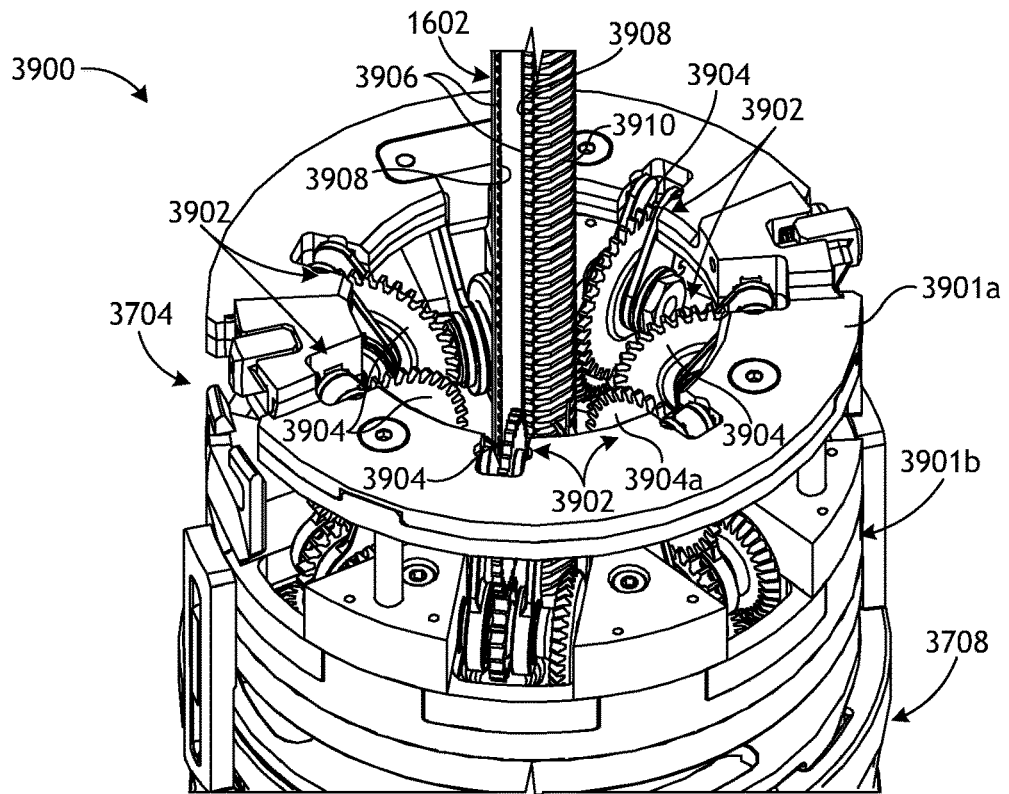
FIGS. 39A and 39B are isometric open (disengaged) and closed (engaged) views, respectively, of another example actuation system, according to one or more additional embodiments.
Figure 39B:
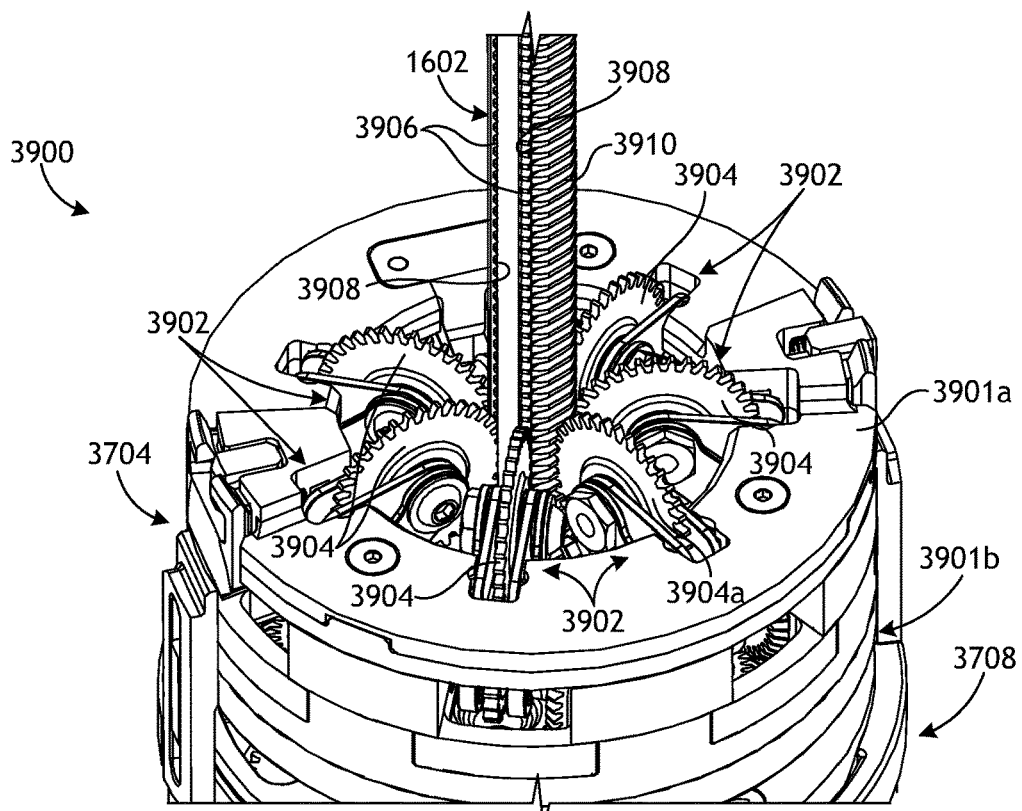

FIGS. 39A and 39B are isometric open (disengaged) and closed (engaged) views, respectively, of another example actuation system 3900, according to one or more embodiments. The actuation system 3900, also referred to as an axle redirect assembly, may be similar in some respects to the actuation system 1700 of FIGS. 17A-17B, and may thus be best understood with reference thereto. The actuation 3900 may be housed within the handle 3704 and operable to actuate (operate) the end effector 1604 (FIG. 16), articulate the wrist 1606 (FIG. 16), and axially move (translate) the shaft 1602 relative to (i.e., through) the handle 3704. Several parts and structural elements of the handle 3704, such as the outer housing, are omitted from FIGS. 39A-39B to enable ease of viewing of the actuation system 3900 for purposes of discussion.

As illustrated, the actuation system 3900 may include a first or "upper" mounting assembly 3901a and a second or "bottom" mounting assembly 3901b Briefly, the upper mounting assembly 3901a is a translating ring that moves to allow and enable the assembly of the instrument shaft 1602 to the actuation system 3900 and the decoupler 3708, and the bottom mounting assembly 3901b is the base of the axle redirect assembly or actuation system 3900. The mounting assemblies 3901a,b may be vertically offset from each other and concentrically arranged about the shaft 1602. A plurality of spur linkage subassemblies 3902 may be pivotably mounted to the mounting assemblies 3901a,b and configured to pivot between a first or "disengaged" position, as shown in FIG. 39A, and a second or "engaged" position, as shown in FIG. 39B.

Each spur linkage subassembly 3902 includes a corresponding drive gear 3904 arranged to drive against an adjacent sliding rack gear 3906 (two visible in FIGS. 39A-39B). Each sliding rack gear 3906 is movably nested within a corresponding longitudinal channel 3908 defined along all or a portion of the shaft 1602. In the illustrated embodiment, the drive gears 3904 are depicted as spur gears with teeth matable with corresponding teeth defined on the opposing sliding rack gear 3906. Accordingly, the drive gears 3904 may alternatively be referred to herein as "spur" gears, and operation of the spur gears 3904 and corresponding rack gears 3906 may conform to known rack-and-pinion operation. Driving a given sliding rack gear 3906 will urge the sliding rack gear 3906 to move (slide) within its corresponding longitudinal channel 3908, and moving the sliding rack gear 3906 within the channel 3908 may actuate (operate) the end effector 1604 (FIG. 16) and/or articulate the wrist 1606 (FIG. 16).

One of the drive gears is indicated in FIGS. 39A-39B as a shaft drive gear 3904a, which may be arranged to drive against an adjacent shaft rack gear 3910. The shaft rack gear 3910 may form part of and may otherwise be defined along all or a portion of the outer surface of the shaft 1602. Driving against the shaft rack gear 3910 will cause the shaft 1602 to move (translate) axially relative to (i.e., through) the handle 3704 (FIG. 16).

Figure 40:
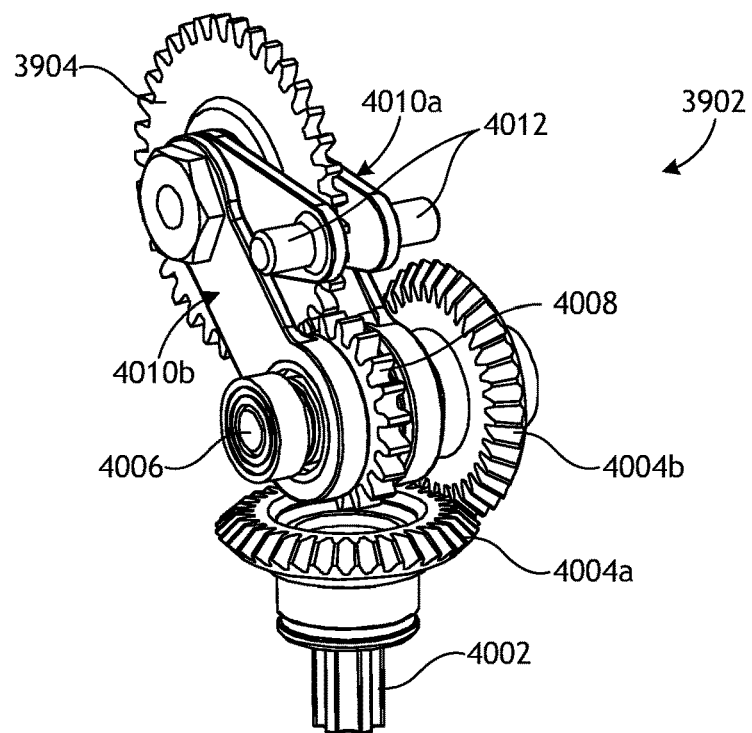
FIG. 40 is an isometric view of an example spur linkage subassembly, according to one or more embodiments.

Referring briefly to FIG. 40, illustrated is an isometric view of an example spur linkage subassembly 3902, according to one or more embodiments. As illustrated, the spur linkage subassembly 3902 includes a rotatable drive input 4002, which, in some embodiments, can be driven by one of the drive outputs 3810 (FIG. 38) of the instrument driver 3706 (FIGS. 37-38). In embodiments that include the decoupler 1616 (FIG. 37), however, a transmission differential or differential assembly provided by the decoupler 1616 will axially interpose the drive input 4002 and a corresponding drive output 3810, as generally described herein. In such embodiments, any rotational torque provided by a given drive output 3810 will be transferred to the corresponding drive input 4002 via a corresponding transmission differential of the decoupler 1616.

A gear train including one or more intermediate gears may interpose the drive input 4002 and the corresponding drive gear 3904, such that rotating the drive input 4002 will cause the corresponding drive gear 3904 to rotate. Those skilled in the art will readily appreciate that this gear train can assume a variety of configurations. In the illustrated embodiment, for example, the gear train includes mating bevel gears, shown as a bevel drive gear 4004*a* arranged to drive a bevel driven gear 4004*b*. The bevel drive gear 4004*a* may be coupled to or otherwise form part of the drive input 4002 such that rotation of the drive input 4002 correspondingly rotates the bevel drive gear 4004*a*. In some embodiments, the bevel driven gear 4004*b* may be mounted to an axle 4006 configured to be rotatably mounted to the lower mounting assembly 3901*b* (FIGS. 39A-39B). A spur gear 4008 may also be mounted to the axle 4006 and axially offset from the bevel driven gear 4004*b*. In at least one embodiment, however, the spur gear 4008 may be coupled to or otherwise form part of the bevel driven gear 4004*b*. In either scenario, rotation of the bevel driven gear 4004*b* will cause the spur gear 4008 to correspondingly rotate, and the spur gear 4008 may be arranged to drive the drive gear 3904.

The intermeshed bevel gears 4004*a,b* facilitate the directional change required in the handle 3704 (FIGS. 39A-39B). More specifically, the bevel gears 4004*a,b* redirect motor rotation of the drive input 4002 to be perpendicular to the shaft 1602 (FIGS. 39A-39B). Through the depicted gear train arrangement, rotation of the drive input 4002 will correspondingly move the rack gears 3906 (FIGS. 39A-39B). In other embodiments, other known gearing mechanisms may be utilized or combined in any number of configurations and dimensioned for optimal torque and/or speed outputs. In at least one embodiment, for example, the gear train may incorporate worm gears or a combination of bevel and spur gears. Moreover, in at least one embodiment, the gear train may be omitted and rotating the drive input 4002 may directly drive an adjacent rack gear 3906 without departing from the scope of the disclosure.

While the spur linkage assembly 3902 shown in FIG. 40 is described with reference to interfacing with a sliding rack gear 3906 (FIGS. 39A-39B), the foregoing description is equally applicable to a spur linkage assembly 3902 configured to interface with the shaft rack gear 3910. In such embodiments, the drive input 4002 may be referred to as a "shaft drive input," which may be configured to cause the shaft drive gear 3904*a* (FIGS. 39A-39B) to rotate (operate) and drive against the shaft rack gear 3910. Driving against the shaft rack gear 3910, as mentioned above, will cause the shaft 1602 (FIGS. 39A-39B) to move (translate) axially relative to (i.e., through) the handle 3704 (FIGS. 39A-39B).

Still referring to FIG. 40, the spur linkage subassembly 3902 may further include a first or "upper" linkage 4010*a* and a second or "lower" linkage 4010*b*. As illustrated, one end of the upper linkage 4010*a* may provide or otherwise define a pair of pins 4012 configured to help pivotably couple the upper linkage 4010*a* to the upper mounting assembly 3901*a* (FIGS. 39A-39B). The pins 4012, however, could be replaced with any other type of pivotable coupling engagement mechanism or structure, without departing from the scope of the disclosure. The opposing end of the upper linkage 4010*a* may be pivotably coupled to one end of the lower linkage 4010*b*, and the opposing end of the lower linkage 4010*b* may be rotatably mounted to the axle 4006, which, as mentioned above, can be rotatably mounted to the lower mounting assembly 3901*b* (FIGS. 39A-39B).

Referring again to FIGS. 39A-39B, with continued reference to FIG. 40, in some embodiments, the spur linkage subassemblies 3902 may be spring biased to the disengaged position, shown in FIG. 39A. In the disengaged position, the drive gears 3904 are disengaged from the sliding rack gears 3906 and the shaft drive gear 3904*a* is disengaged from the shaft rack gear 3910. The spur linkage subassemblies 3902 are transitioned to the engaged position by collapsing the axial distance between the upper and lower mounting assemblies 3901*a,b*. As the upper mounting assembly 3901*a* is lowered toward the lower mounting assembly 3901*b*, the spur linkage subassemblies 3902 will pivot in tandem at the pivotably coupled linkages 4010*a,b* toward the engaged (closed) position, as shown in FIG. 39B. In the engaged position, each drive gear 3904, 3904*a* engages and mates with the adjacent sliding rack gear 3906 or shaft rack gear 3910 simultaneously. Accordingly, the upper linkage 4010*a* may be configured to move linearly up and down to move the drive gears 3904, 3904*a* away from and toward the axis of the shaft 1602 as the actuation system 3900 transitions between the open and closed positions.

Figure 41:
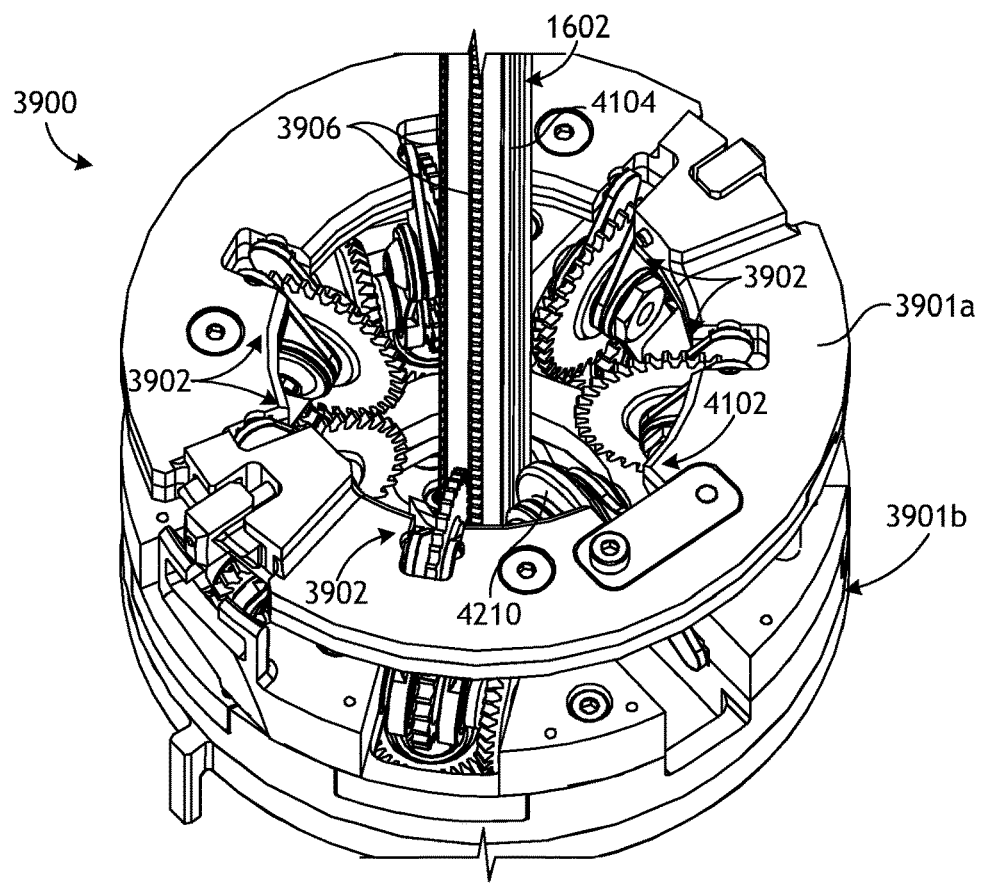
FIG. 41 is another isometric view of the actuation system of FIGS. 39A-39B, according to one or more additional embodiments.
Figure 42:
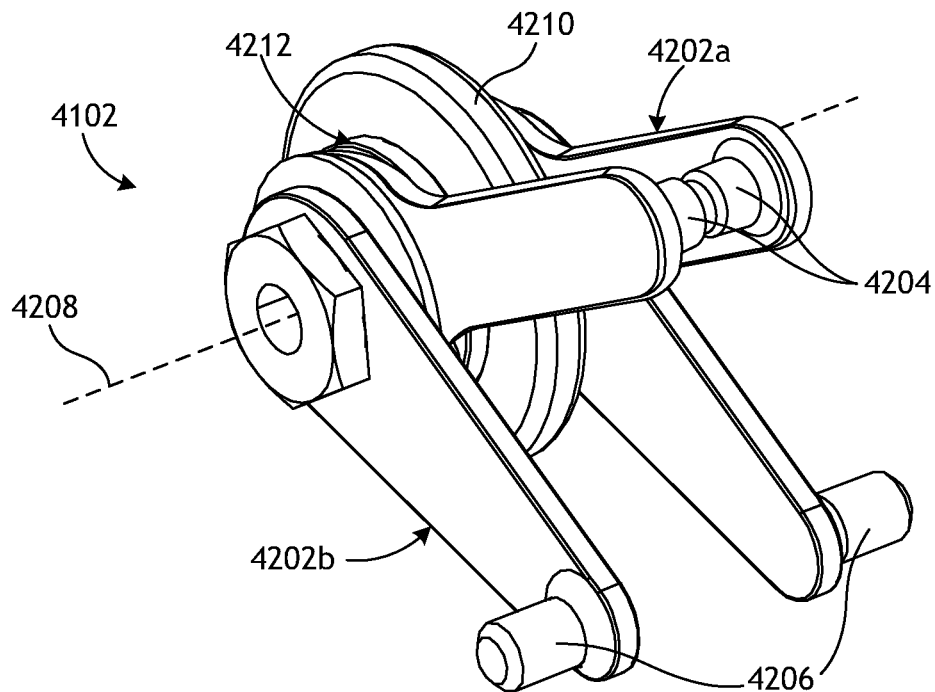
FIG. 42 is an enlarged, isometric view of one example of the clocking wheel linkage subassembly, according to one or more embodiments.

Referring now to FIG. 41, in some embodiments, the actuation system 3900 may further include a clocking wheel linkage subassembly 4102 configured to help properly align (e.g., angularly, rotationally, etc.) the actuation system 3900 with the shaft 1602. FIG. 42 is an enlarged, isometric view of one example of the clocking wheel linkage subassembly 4102, according to one or more embodiments. As illustrated, the clocking wheel linkage subassembly 4102 may include a first or "upper" linkage 4202*a* and a second or "lower" linkage 4202*b*. As illustrated, one end of the upper linkage 4202*a* may provide or otherwise define a pair of pins 4204 configured to help pivotably couple the upper linkage 4202*a* to the upper mounting assembly 3901*a* (FIG. 41). Similarly, one end of the lower linkage 4202*b* may also provide or otherwise define a pair of pins 4206 configured to help pivotably couple the lower linkage 4202*a* to the lower mounting assembly 3901*b*. The pins 4204, 4206, however, could be replaced with any other type of pivotable coupling engagement mechanism or structure, without departing from the scope of the disclosure. The opposing ends of the linkages 4202*a,b* may be pivotably attached to each other at a pivot axis 4208.

The clocking wheel linkage subassembly 4102 may also include a clocking wheel 4210 rotatably mounted at the pivot axis 4208. In some embodiments, one or more thrust bearings and/or washers 4212 (e.g., belleville washers) may help maintain the pivotably mounted linkages 4202*a,b* and clocking wheel 4210 axially tight and rotationally free at the pivot axis 4208.

Referring again to FIG. 41, with continued reference to FIG. 42, similar to the spur linkage subassemblies 3902, the clocking wheel linkage subassembly 4102 may be pivotably mounted to the mounting assemblies 3901*a,b* and configured to pivot between a first or "disengaged" position, as shown in FIG. 39A, and a second or "engaged" position, as shown in FIGS. 39B and 41. Upon transitioning to the engaged position, the clocking wheel 4210 may be configured to be received within and otherwise mate with a longitudinal groove 4104 defined along all or a portion of the shaft 1602. Receiving the clocking wheel 4210 within the groove 4104 will help properly align all the spur linkage subassemblies 3902 rotationally (angularly) with the proper sliding rack gears 3906 or shaft rack gear 3910 (FIGS. 39A-39B).

Figure 43:
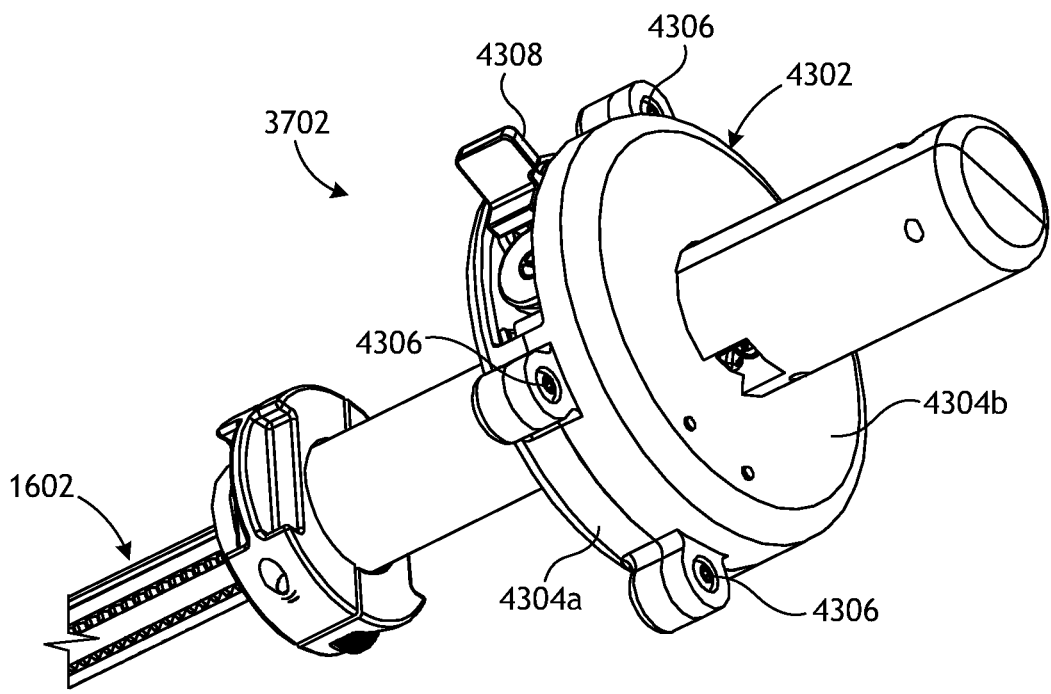
FIG. 43 is an enlarged isometric view of the tailpiece of FIG. 37, according to one or more embodiments.

FIG. 43 is an enlarged isometric view of the tailpiece 3702, according to one or more embodiments. The tailpiece 3702 may be similar in respects to the tailpiece 1620 of FIG. 16, and may thus be best understood with reference thereto. For example, similar to the tailpiece 1620, the tailpiece 3702 may be arranged at the proximal end of the shaft 1602. Moreover, the tailpiece 3702 may comprise a mechanical device that provides a means for manually controlling the end effector 1604 (FIG. 37) and/or the wrist 1606 (FIG. 37). The tailpiece 3702 may also be used to maintain tension in the surgical tool 3700 (FIG. 37) when disconnected from the instrument driver 3706 (FIG. 37). As described herein, however, the tailpiece 3702 can be provided in various forms and still perform essentially the same function, without departing from the scope of the present disclosure.

In the illustrated embodiment, the tailpiece 3702 includes a housing 4302 that may be attached to the proximal end of the shaft 1602. The housing 4302 may include first and second housing portions 4304a and 4304b that are matable and coupled together using one or more mechanical fasteners 4306 or the like. The tailpiece 3702 may further include a manual actuation device, which, in this embodiment, comprises a slider 4308 that extends out of the housing 4302 and provides a means for manually actuating the tailpiece 3702. More specifically, the slider 4308 extends past an outer circumferential periphery of the housing 4302, and as the slider 4308 is manually moved (rotated) about the outer circumference, the end effector 1604 (FIG. 37) may be actuated or the wrist 1606 (FIG. 37) may be articulated.

Figure 44:
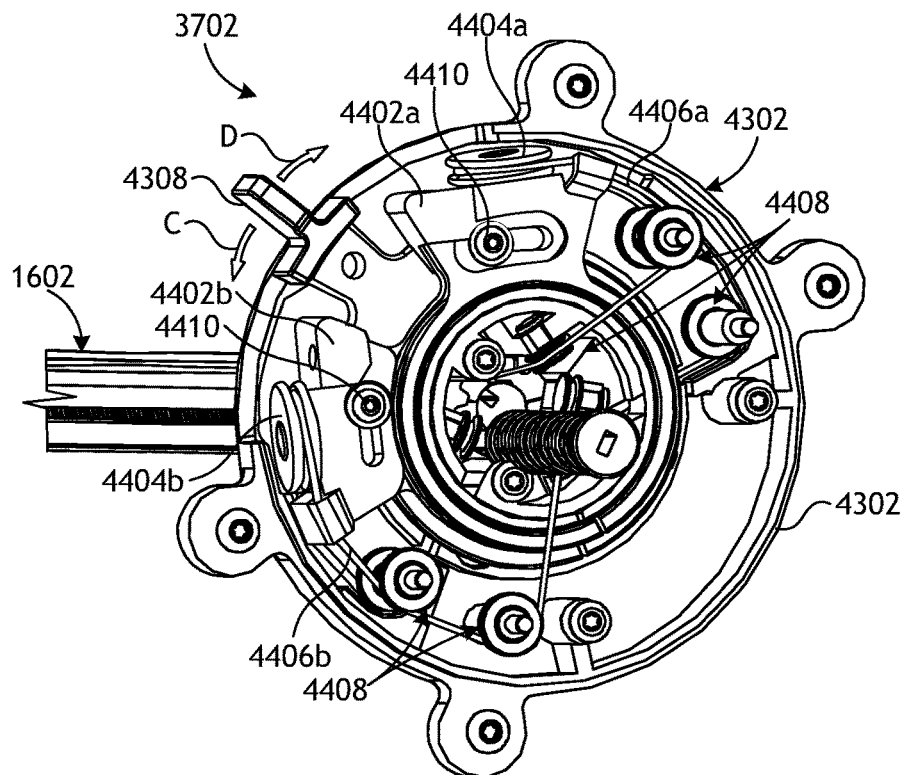
FIG. 44 is an isometric view of the interior of the tailpiece of FIG. 43, according to one or more embodiments.

FIG. 44 is an isometric view of the interior of the tailpiece 3702, according to one or more embodiments. The second or "upper" housing portion 4304b is omitted to enable viewing of the internal components and mechanics of the tailpiece 3702. As illustrated, the tailpiece 3702 includes first and second pulley arms 4402a and 4402b that can be secured to the slider 4308 such that manually rotating the slider 4308 about the axis of the shaft 1602 correspondingly rotates the pulley arms 4402a,b in the same angular direction. First and second proximal pulleys 4404a and 4404b may also be rotatably mounted to the first and second pulley arms 4402a,b and move with the pulley arms 4402a,b within the housing 4302 as the slider 4308 is manually moved. The proximal pulleys 4404a,b may be similar to the proximal pulley 1806b discussed above with reference to FIGS. 18A-18C, and thus have corresponding proximal cables 4406a and 4406b extending (wrapped) thereabout, where the proximal cables 4406a,b are similar to the proximal cable 1804b of FIGS. 18A-18C.

As illustrated, the proximal cables 4406a,b may be routed to and from the shaft 1602 using one or more rerouting pulleys 4408. Some of the rerouting pulleys 4408 may be located within the shaft 1602 and may exhibit horizontal axes (e.g., perpendicular to shaft 1602), while other rerouting pulleys 4408 may be located along the outer diameter of the housing 4302 and exhibit vertical axes (e.g., parallel to the shaft 1602). Each proximal cable 4406a,b is distributed through corresponding rerouting pulleys 4408 and wrapped around the corresponding proximal pulley 4404a,b, respectively.

When the slider 4308 is manually moved in either angular direction relative to the outer circumference of the housing 4302, the pulley arms 4402a,b move in the same angular direction, which causes one of the proximal pulleys 4404a,b to draw in its proximal cable 4406a,b from the shaft 1602 while simultaneously causing the other proximal pulley 4404a,b to pay out its proximal cable 4406a,b to the shaft 1602. More specifically, as the slider 4308 moves counter-clockwise, for example, as indicated by the arrow C, the first proximal pulley 4404a moves away from its corresponding rerouting pulleys 4408 and thereby draws a length of the first proximal cable 4406a into the tailpiece 3702 from the shaft 1602. At the same time, the second proximal pulley 4404b simultaneously moves toward its corresponding rerouting pulleys 4408 and thereby pays out a length of the second proximal cable 4406b into the shaft 1602. Consequently, the net cable length of the cables 4406a,b remains the same because the two pulleys 4404a,b have the same displacement, but the change in length of each pair changes, which causes movement (actuation) of the jaws 1608, 1610 (FIG. 37). Moving the slider 4308 clockwise, as indicated by arrow D, will act on the first and second proximal cables 4406a,b in the opposite manner, and actuate the jaws 1608, 1610 in the opposite direction. In alternative embodiments, this cable configuration may alternatively allow pitch and yaw articulations at the wrist 1606 (FIG. 37) to create motion where each cable loop rolls around its respective pulley system.

The tailpiece 3702 may also be useful in facilitating assembly pretension in the cable system. More specifically, during assembly of the tool, the pulley arms 4402a,b may be able to move relative to the slider 4308. When the full system is assembled with cable routing, the jaws 1608, 1610 (FIG. 37) are held still and the pulley arms 4402a,b are rotated (drawn) towards each other and the center of the slider 4308. This rotation may be done with a set torque load to create a desired pretension in the system, and once the predetermined tension is achieved, one or more mechanical fasteners 4410 may be used to rigidly secure the pulley arms 4402a,b to the slider 4308. Consequently, by setting the relative position of the two pulley arms 4402a,b to the slider 4308, the pretension of the cable system may be set and held.

Figure 45:
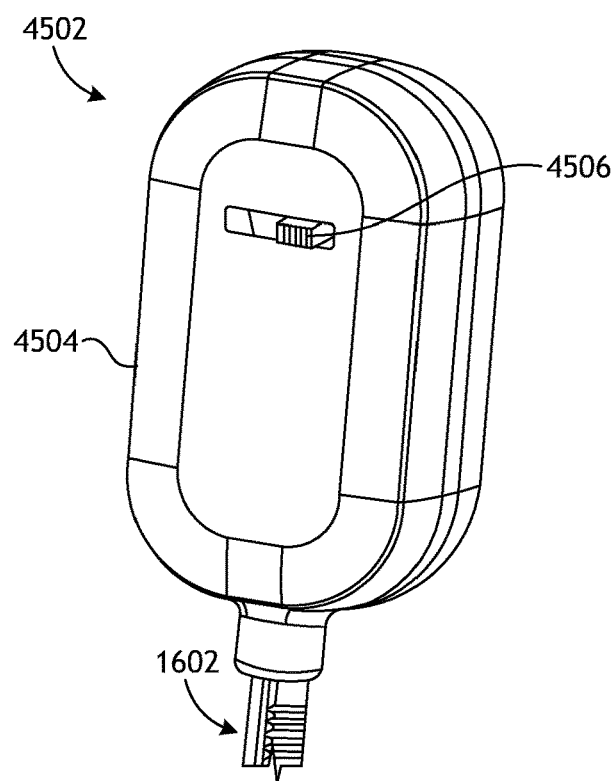
FIG. 45 is an isometric view of another embodiment of the tailpiece of FIG. 37, according to one or more additional embodiments.

FIG. 45 is an isometric view of another example tailpiece 4502, according to one or more additional embodiments. The tailpiece 4502 may be similar in some respects to the tailpiece 1620 of FIG. 16 or the tailpiece 3702 of FIG. 37, and thus may comprise a mechanical device that provides a means for manually controlling the end effector 1604 (FIG. 37) and/or the wrist 1606 (FIG. 37). The tailpiece 4502 may also be used to maintain tension in the surgical tool 3700 (FIG. 37) when disconnected from the instrument driver 3706 (FIG. 37).

As illustrated, the tailpiece 4502 includes a housing 4504 that may be attached to the proximal end of the shaft 1602. The tailpiece 4502 may further include a manual actuation device, which, in this embodiment, comprises a slider 4506 that extends out of the housing 4504 and provides a means for manually actuating the tailpiece 4502. In some embodiments, as illustrated, the slider 4506 may be manually moved side to side relative to the housing 4504 to actuate the tailpiece 4502. In other embodiments, however, the slider 4506 may be configured to slide (move) in other directions, without departing from the scope of the disclosure. As the slider 4506 is manually moved, the end effector 1604 (FIG. 37) may be actuated or the wrist 1606 (FIG. 37) may be articulated.

Figure 46A:
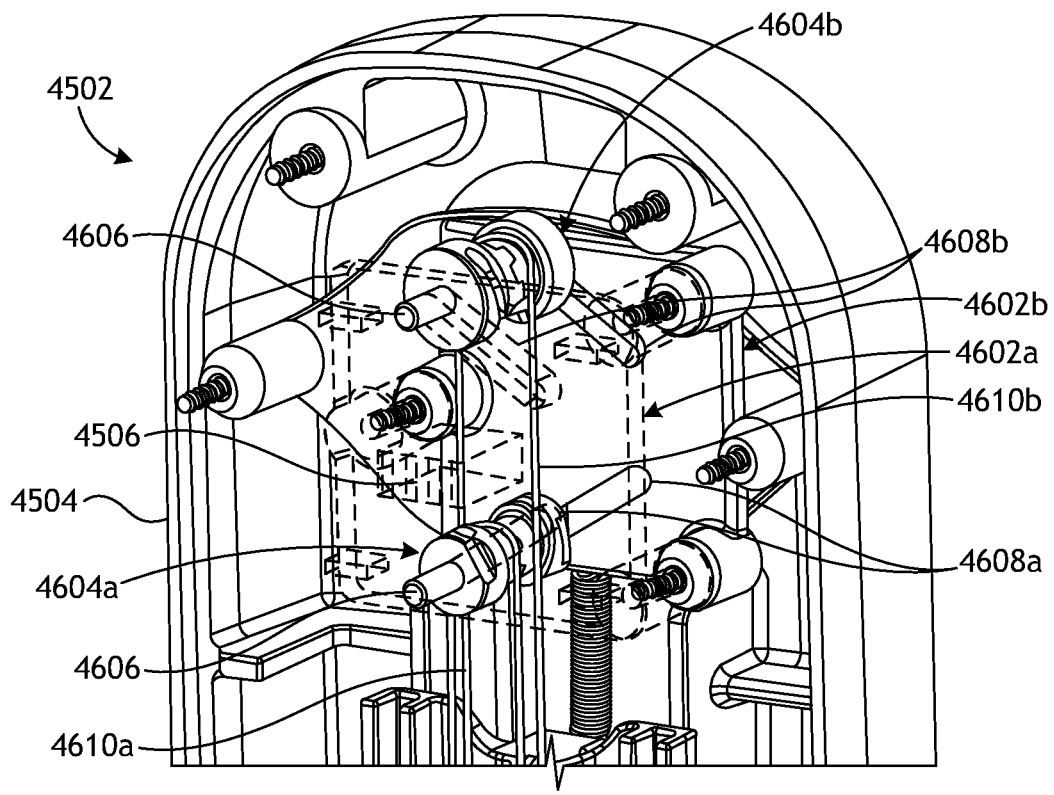
FIGS. 46A and 46B are isometric views of the interior of the tailpiece of FIG. 45, according to one or more embodiments.
Figure 46B:
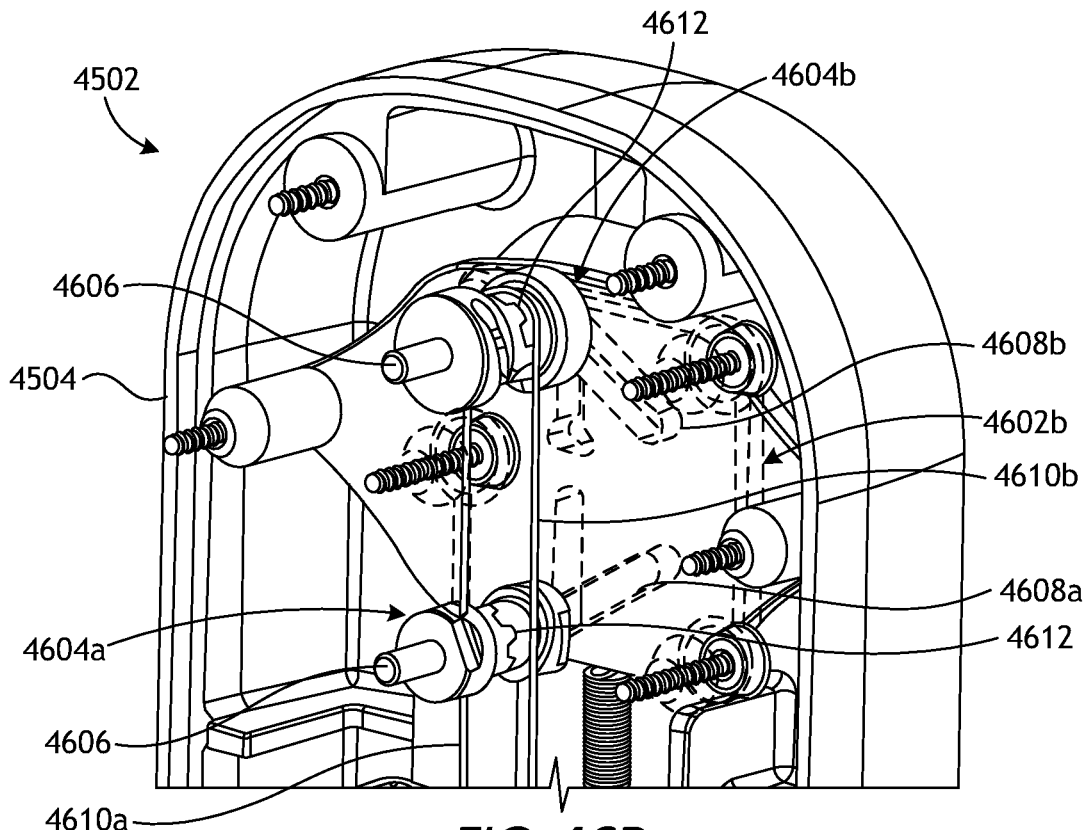

FIGS. 46A and 46B are isometric views of the interior of the tailpiece 4502, according to one or more embodiments. A top portion of the housing 4504 is omitted in FIGS. 46A-46B to enable viewing of the internal components and mechanisms of the tailpiece 4502. As illustrated, the tailpiece 4502 includes first and second camming plates 4602a and 4602b that are vertically offset from each other within the housing 4504. In FIG. 46B, only the second or "lower" camming plate 4602b is shown to facilitate better viewing of various component parts of the tailpiece 4502. The camming plates 4602a,b may be secured together and mounted within the housing 4504 such that they are able to move (slide) in tandem relative to housing 4504. As illustrated, the first camming plate 4602a may define or otherwise provide the slider 4506.

The tailpiece 4502 may further include first and second proximal pulleys 4604a and 4604b rotatably mounted between the first and second camming plates 4602a,b.

Each pulley 4604a,b may be rotatably mounted to a corresponding pin 4606 extending between the camming plates 4602a,b, and the pins 4606 may allow the pulleys 4604a,b to move laterally within the housing 4504 as the slider 4506 is manually moved. More specifically, each camming plate 4602a,b defines and otherwise provides distal and proximal slots 4608a and 4608b configured to receive opposing ends of each pin 4606. The pin 4606 of the first pulley 4604a may be arranged to extend between the camming plates 4602a,b and into the distal slots 4608a, and the pin 4606 of the second pulley 4604b may be arranged to extend between the camming plates 4602a,b and into the proximal slots 4608b. As illustrated, the distal and proximal slots 4608a,b of each camming plate 4602a,b are angled and extend in the same direction such that the distal slots 4608a align and the proximal slots 4608b align. Moreover, the slots 4608a,b converge toward or away from each other in a lateral direction, which allows the pulleys 4604a,b to progressively converge or diverge as the pins 4606 traverse the slots 4608a,b.

The proximal pulleys 4604a,b may be similar to the proximal pulley 1806b discussed above with reference to FIGS. 18A-18C, and may thus have a corresponding proximal cable 4610a and 4610b extending (wrapped) thereabout, where the proximal cables 4610a,b are similar to the proximal cable 1804b of FIGS. 18A-18C. As the slider 4506 is moved laterally, the camming plates 4602a,b correspondingly move laterally and force the pulleys 4604a,b (i.e., the pins 4606) to traverse the slots 4608a,b defined in the camming plates 4602a,b. As they traverse the slots 4608a,b, the pulleys 4604a,b converge toward each other or diverge away from each other, depending on the direction of the slider 4506, which correspondingly changes the length of the cables 4610a,b within the system. For example, moving the slider 4506 to the left in FIGS. 46A-46B will tend make the pulleys converge toward each other, and moving the slider 4506 to the right in FIGS. 46A-46B will tend make the pulleys diverge away from each other. The net cable length of the cables 4610a,b, however, remains the same because the two pulleys 4604a,b have the same displacement, but the change in length of each pair changes, which causes movement (actuation) of the jaws 1608, 1610 (FIG. 37). In alternative embodiments, this cable configuration may be configured to allow pitch and yaw articulations of the wrist 1606 (FIG. 37) to create motion where each cable loop rolls around its respective pulley system.

As best seen in FIG. 46B, the pulleys 4604a,b may be configured as spools rotatably mounted to their corresponding pins 4606, and each spool has two parts that are matable at a corresponding engagement feature 4612. When the two parts are properly mated, the engagement feature 4612 prevents the two parts of each pulley 4604a,b from rotating relative to the other. When separated, however, the two parts may be able to rotate relative to one another. In the illustrated embodiment, the engagement features 4612 comprise castellated features, but could alternatively comprise other types of structural features that prevent relative rotation of the opposing parts when engaged, but allow relative rotation when separated. Assembly pretension in the cable system can be achieved by rotating the two parts of each pulley 4604a,b in opposite directions in order to apply a set torque load on the associated cables 4610a,b, and thus creating the desired pretension in the system. Once the desired (predetermined) tension is reached, the two parts may be mated once again at the engagement feature 4612 to hold the pretension of the system.

Figure 47:
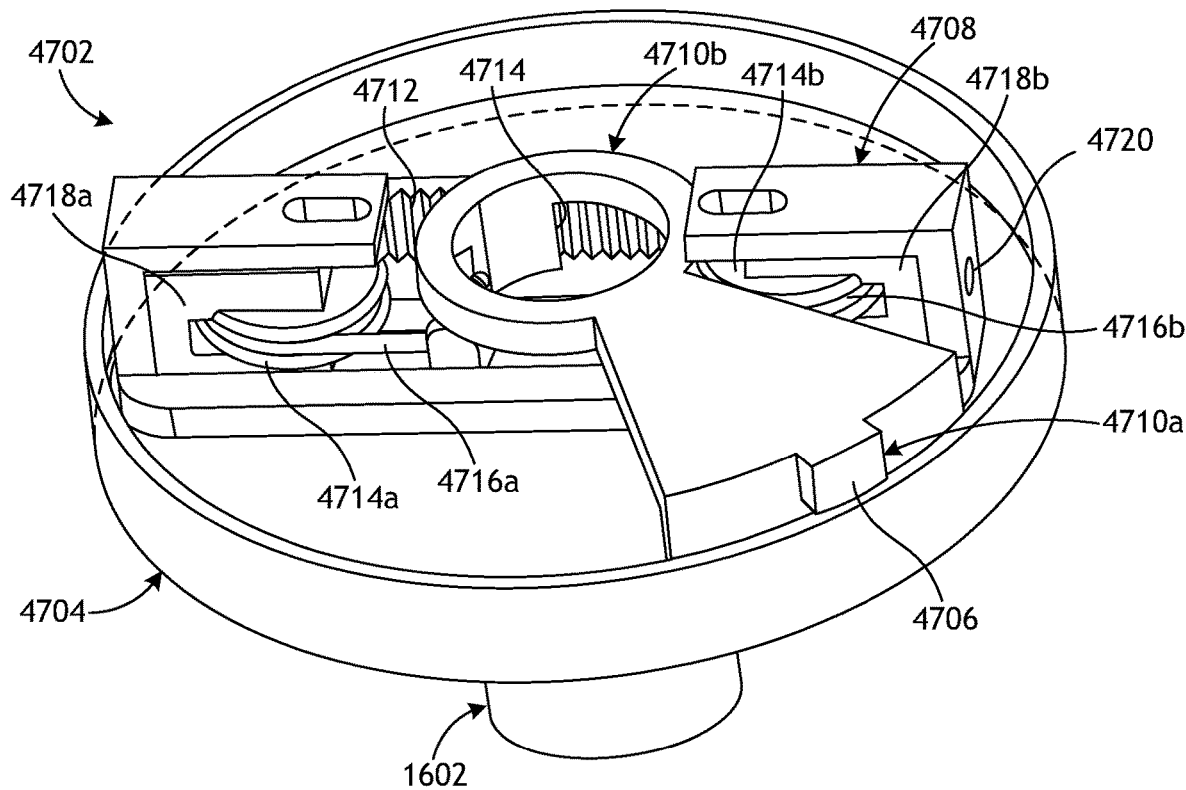
FIG. 47 is an enlarged isometric view of another example tailpiece, according to one or more additional embodiments.

FIG. 47 is an enlarged isometric view of another example tailpiece 4702, according to one or more additional embodiments. The tailpiece 4702 may be similar in respects to the tailpiece 3702 of FIGS. 43-44, and may thus be best understood with reference thereto. For example, similar to the tailpiece 3702, the tailpiece 4702 may be arranged at the proximal end of the shaft 1602 and may comprise a mechanical device that provides a means for manually controlling the end effector 1604 (FIG. 37) and/or the wrist 1606 (FIG. 37). The tailpiece 4702 may also be used to maintain tension in the surgical tool 3700 (FIG. 37) when disconnected from the instrument driver 3706 (FIG. 37).

The tailpiece 4702 may include a housing 4704 that may be attached to the proximal end of the shaft 1602. In FIG. 47, an upper portion of the housing 4704 is omitted to enable viewing of the internal components and mechanics of the tailpiece 4702. The tailpiece 4702 may further include a manual actuation device, which, in this embodiment, comprises a slider 4706 that extends out of the housing 4704 and provides a means for manually actuating the tailpiece 4702. Similar to the slider 4308 of FIGS. 43-44, the slider 4706 extends past an outer circumferential periphery of the housing 4704. As the slider 4706 is manually moved (rotated) about a portion of the outer circumference, the end effector 1604 (FIG. 37) may be actuated or the wrist 1606 (FIG. 37) may be articulated.

Unlike the tailpiece 3702 of FIGS. 43-44, however, the tailpiece 4702 includes an internal linear slider 4708 movably mounted within the housing 4704. A first end 4710a of the slider 4706 extends out of the housing 4704 to be manually manipulated by the user, but the opposing second end 4710b of the slider 4706 is configured to interact with the linear slider 4708 such that manually sliding (rotating) the slider 4706 causes the linear slider 4708 to move laterally within the housing 4704. In some embodiments, for example, the linear slider 4708 may define or otherwise provide a rack gear 4712, and the second end 4710b of the slider 4706 may define or otherwise provide a pinion gear 4714 (mostly occluded) arranged to engage and mate with the rack gear 4712. As the slider 4706 is moved (rotated), the pinion gear 4714 drives against the rack gear 4712 and thereby causes the linear slider 4708 to move laterally within the housing 4704, depending on the driving direction of the pinion gear 4714.

The tailpiece 4702 may further include first and second proximal pulleys 4714a and 4714b rotatably mounted to opposing ends of the linear slider 4708. The proximal pulleys 4714a,b may be similar to the proximal pulley 1806b discussed above with reference to FIGS. 18A-18C, and thus have corresponding proximal cables 4716a and 4716b extending (wrapped) thereabout, where the proximal cables 4716a,b are similar to the proximal cable 1804b of FIGS. 18A-18C. The proximal cables 4716a,b may be routed to and from the shaft 1602 using one or more rerouting pulleys (not shown).

When the slider 4706 is manually moved in either angular direction relative to the outer circumference of the housing 4704, the linear slider 4708 moves linearly within the housing 4704. As the linear slider 4708 moves, the axis of each proximal pulley 4714a,b is moved relative to the axis of the shaft 1602. As a result, and depending on the sliding direction of the linear slider 4708, one of the proximal pulleys 4714a,b will draw in its proximal cable 4716a,b from the shaft 1602, and the other proximal pulley 4714a,b will simultaneously pay out its proximal cable 4716a,b to the shaft 1602. Consequently, the net cable length of the cables 4716a,b remains the same because the two pulleys 4714a,b will have the same displacement, but the change in length of each pair changes, which causes movement (actuation) of the jaws 1608, 1610 (FIG. 37). In alternative embodiments, this cable configuration may alternatively allow pitch and yaw articulations at the wrist 1606 (FIG. 37) to create motion where each cable loop rolls around its respective pulley system.

The tailpiece 4702 may also be useful in facilitating assembly pretension in the cable system. More specifically, in some embodiments, the pulleys 4714a,b may be rotatably mounted to the linear slider 4708 using corresponding pulley brackets 4718a,b. During assembly of the tool, the pulley brackets 4718a,b can be adjusted relative to the linear slider 4708 so that a set torque load (tension) on the cables 4716a,b is created; e.g., the axis of the pulleys 4714a,b may be pulled outward from the device or shaft 1602 centerline. Once the predetermined tension is achieved, the pulley brackets 4718a,b may be secured to the linear slider 4708 in that position using one or more mechanical fasteners (not shown) accessible to the pulley brackets 4718a,b via one or more apertures 4720 (one shown) defined in the linear slider 4708.

Embodiments disclosed herein include:

A. A robotic surgical tool that includes a handle providing a plurality of drive inputs, an elongate shaft extendable through the handle and including a plurality of sliding rack gears movably nested within a corresponding plurality of longitudinal channels defined along the shaft, an end effector arranged at a distal end of the shaft and an articulable wrist interposing the end effector and the distal end, an actuation system housed within the handle and operatively coupling the plurality of drive inputs to the plurality of sliding rack gears such that actuation of the plurality of the drive inputs moves the plurality of sliding rack gears and causes operation of at least one of the end effector and the wrist, and a tailpiece arranged at a proximal end of the shaft and operably coupled to the plurality of sliding rack gears, the tailpiece including a housing and a manual actuation device mounted to the housing and manually actuatable to act on the plurality of sliding rack gears and thereby operate at least one of the end effector and the wrist.

B. A method of operating a robotic surgical tool including arranging a robotic surgical tool adjacent a patient, the robotic surgical tool including a handle providing a plurality of drive inputs, an elongate shaft extendable through the handle and including a plurality of sliding rack gears movably nested within a corresponding plurality of longitudinal channels defined along the shaft, an end effector arranged at a distal end of the shaft and an articulable wrist interposing the end effector and the distal end, an actuation system housed within the handle and operatively coupling the plurality of drive inputs to the plurality of sliding rack gears such that actuation of the plurality of the drive inputs moves the plurality of sliding rack gears and causes operation of at least one of the end effector and the wrist, and a tailpiece arranged at a proximal end of the shaft and operably coupled to the plurality of sliding rack gears, the tailpiece including a housing and a manual actuation device mounted to the housing. The method further including manually actuating the manual actuation device and thereby acting on the plurality of sliding rack gears to operate at least one of the end effector and the wrist.

Each of embodiments A and B may have one or more of the following additional elements in any combination: Element 1: wherein the manual actuation device comprises first and second buttons pivotably coupled to the housing, a first pulley rotatably mounted to the first button, a second pulley rotatably mounted to the second button, a first cable wrapped around the first pulley and operatively coupled to a first pair of sliding rack gears of the plurality of sliding rack gears, and a second cable wrapped around the second pulley and operatively coupled to a second pair of sliding rack gears of the plurality of sliding rack gears, wherein manually depressing one of the first and second buttons simultaneously causes the other of the first and second buttons to pivot in an opposite direction and thereby move the first and second pairs of sliding rack gears to operate at least one of the end effector and the wrist. Element 2: further comprising a tensioning nut threadably attached to the shaft at the proximal end and adjacent the housing, wherein rotating the tensioning nut applies an axial load on the housing and thereby places the first and second cables in tension. Element 3: further comprising a manual accessory attachable to the tailpiece and including opposing handles, wherein at least one of the opposing handles is manually manipulatable to act on at least one of the first and second buttons. Element 4: wherein the manual actuation device comprises a slider that extends out of the housing and past an outer circumference of the housing, a first pulley arm mounted to the slider within the housing and having a first pulley rotatably mounted thereto, a second pulley arm mounted to the slider within the housing and having a second pulley rotatably mounted thereto, a first cable wrapped around the first pulley and operatively coupled to a first pair of sliding rack gears of the plurality of sliding rack gears, and a second cable wrapped around the second pulley and operatively coupled to a second pair of sliding rack gears of the plurality of sliding rack gears, wherein manually moving the slider about the outer circumference of the housing correspondingly moves the first and second pulley arms within the housing and thereby draws a length of the first cable into the tailpiece from the shaft while simultaneously paying out a length of the second cable into the shaft to move the first and second pairs of sliding rack gears and operate at least one of the end effector and the wrist. Element 5: wherein the manual actuation device comprises first and second camming plates movably mounted within the housing and vertically offset from each other, each camming plate defining distal and proximal slots that are angled to converge or diverge from one another, a slider defined on the first camming plate and extending out of the housing, a first pulley rotatably mounted to a first pin that extends between the first and second camming plates and into the distal slot of each camming plate, a second pulley rotatably mounted to a second pin that extends between the first and second camming plates and into the proximal slot of each camming plate, a first cable wrapped around the first pulley and operatively coupled to a first pair of sliding rack gears of the plurality of sliding rack gears, and a second cable wrapped around the second pulley and operatively coupled to a second pair of sliding rack gears of the plurality of sliding rack gears, wherein manually moving the slider correspondingly moves the first and second camming plates laterally within the housing and thereby urges the first and second pins to traverse the distal and proximal slots, respectively, which moves the first and second pulleys toward or away from each other, and wherein moving the first and second pulleys toward or away from each other acts on the first and second cables to move the first and second pairs of sliding rack gears and operate at least one of the end effector and the wrist. Element 6: wherein each pulley comprises a spool having two parts matable at an engagement feature. Element 7: wherein the manual actuation device comprises a linear slider movably mounted within the housing and defining a rack gear, a slider having a first end that extends out of the housing and past an outer circumference of the housing and a second end that defines a pinion gear engageable with the rack gear, first and second pulleys rotatably mounted to opposing ends of the linear slider, a first cable wrapped around the first pulley and operatively coupled to a first pair of sliding rack gears of the plurality of sliding rack gears, and a second cable wrapped around the second pulley and operatively coupled to a second pair of sliding rack gears of the plurality of sliding rack gears, wherein manually moving the slider about the outer circumference of the housing correspondingly shifts the linear slider within the housing and thereby draws a length of the first cable into the tailpiece from the shaft while simultaneously paying out a length of the second cable into the shaft to move the first and second pairs of sliding rack gears and operate at least one of the end effector and the wrist. Element 8: wherein the actuation system further includes a plurality of drive gears, each drive gear being engageable with a corresponding one of the plurality of sliding rack gears, and a gear train extending between each drive input and each drive gear such that actuation of a given drive input drives the corresponding one of the plurality of sliding rack gears within a corresponding one of the plurality of longitudinal channels. Element 9: wherein the gear train includes one or more intermediate gears that transition a rotational axis of the given drive input by 90° to enable the plurality of drive gears to engage the plurality of sliding rack gears. Element 10: wherein the actuation system further includes first and second mounting assemblies vertically offset from each other and concentrically arranged about the shaft; a plurality of spur linkage subassemblies pivotally mounted to the first and second mounting assemblies, each spur linkage subassembly including a drive gear engageable with a corresponding one of the plurality of sliding rack gears, wherein moving the first mounting assembly toward the second mounting assembly pivots the plurality of spur linkage assemblies between a disengaged position, where the drive gear of each spur linkage subassembly is disengaged from the corresponding one of the plurality of sliding rack gears, and an engaged position, where the drive gear of each spur linkage subassembly is engaged with the corresponding one of the plurality of sliding rack gears. Element 11: wherein each spur linkage subassembly includes a drive gear engageable with a corresponding one of the plurality of sliding rack gears, and a gear train extending between a corresponding one of the plurality of drive inputs and the drive gear such that actuation of the corresponding one of the plurality of drive inputs drives the corresponding one of the plurality of sliding rack gears within a corresponding one of the plurality of longitudinal channels. Element 12: wherein the gear train includes one or more intermediate gears that transition a rotational axis of the corresponding one of the plurality of drive inputs by 90° to enable the drive gear to engage the corresponding one of the plurality of sliding rack gears. Element 13: wherein each spur linkage subassembly further includes a first linkage pivotally coupled to the first mounting assembly, and a second linkage having a first end pivotally coupled to the first linkage and a second end pivotally coupled to the second mounting assembly. Element 14: wherein the actuation system further includes a clocking wheel linkage subassembly comprising a first linkage pivotally coupled to the first mounting assembly, a second linkage having a first end pivotally coupled to the first linkage at a pivot axis and a second end pivotally coupled to the second mounting assembly, and a clocking wheel rotatably mounted to the first and second linkages at the pivot axis, wherein moving the first mounting assembly toward the second mounting assembly pivots the clocking wheel linkage subassembly between the disengaged position, where the clocking wheel is disengaged from a longitudinal groove defined in the shaft, and the engaged position, where the clocking wheel is engaged with the longitudinal groove and thereby angularly aligns each spur linkage subassembly with the corresponding one of the plurality of sliding rack gears.

Element 15: wherein the manual actuation device comprises first and second buttons pivotally coupled to the housing, a first pulley rotatably mounted to the first button, a second pulley rotatably mounted to the second button, a first cable wrapped around the first pulley and operatively coupled to a first pair of sliding rack gears of the plurality of sliding rack gears, and a second cable wrapped around the second pulley and operatively coupled to a second pair of sliding rack gears of the plurality of sliding rack gears, the method further comprising manually depressing one of the first and second buttons and thereby simultaneously causing the other of the first and second buttons to pivot in an opposite direction to move the first and second pairs of sliding rack gears and operate at least one of the end effector and the wrist. Element 16: wherein the tailpiece further includes a tensioning nut threadably attached to the shaft at the proximal end and adjacent the housing, the method further comprising rotating the tensioning nut and thereby applying an axial load on the housing and placing the first and second cables in tension. Element 17: wherein the manual actuation device comprises a slider that extends out of the housing and past an outer circumference of the housing, a first pulley arm mounted to the slider within the housing and having a first pulley rotatably mounted thereto, a second pulley arm mounted to the slider within the housing and having a second pulley rotatably mounted thereto, a first cable wrapped around the first pulley and operatively coupled to a first pair of sliding rack gears of the plurality of sliding rack gears, and a second cable wrapped around the second pulley and operatively coupled to a second pair of sliding rack gears of the plurality of sliding rack gears, the method further comprising manually moving the slider about the outer circumference of the housing and thereby correspondingly moving the first and second pulley arms within the housing, and as the first and second pulley arms move within the housing, drawing a length of the first cable into the tailpiece from the shaft while simultaneously paying out a length of the second cable into the shaft to move the first and second pairs of sliding rack gears and operate at least one of the end effector and the wrist. Element 18: wherein the manual actuation device comprises first and second camming plates movably mounted within the housing and vertically offset from each other, each camming plate defining distal and proximal slots that are angled to converge or diverge from one another, a slider defined on the first camming plate and extending out of the housing, a first pulley rotatably mounted to a first pin that extends between the first and second camming plates and into the distal slot of each camming plate, a second pulley rotatably mounted to a second pin that extends between the first and second camming plates and into the proximal slot of each camming plate, a first cable wrapped around the first pulley and operatively coupled to a first pair of sliding rack gears of the plurality of sliding rack gears, and a second cable wrapped around the second pulley and operatively coupled to a second pair of sliding rack gears of the plurality of sliding rack gears, the method further comprising manually moving the slider and thereby correspondingly moving the first and second camming plates laterally within the housing, as the first and second camming plates laterally within the housing, urging the first and second pins to traverse the distal and proximal slots, respectively, which moves the first and second pulleys toward or away from each other, and moving the first and second pulleys toward or away from each and thereby acting on the first and second cables to move the first and second pairs of sliding rack gears and operate at least one of the end effector and the wrist.

By way of non-limiting example, exemplary combinations applicable to A and B include: Element 1 with Element 2; Element 1 with Element 3; Element 8 with Element 9; Element 10 with Element 11; Element 11 with Element 12; Element 11 with Element 13; Element 11 with Element 14; and Element 15 with Element 16.

3. Implementing Systems and Terminology.

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification, which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
a handle providing a plurality of drive inputs including first and second drive inputs, wherein the handle is couplable to an instrument driver of a robotic surgical system, the instrument driver comprising first and second drive outputs for driving the first and second drive input, respectively;
an elongate shaft extendable through the handle and including a plurality of sliding rack gears movably nested within a corresponding plurality of longitudinal channels defined along the shaft, the plurality of sliding rack gears including first and second sliding rack gears independently moveable relative to one another;
an end effector arranged at a distal end of the shaft and an articulable wrist interposing the end effector and the distal end;
an actuation system housed within the handle and operatively coupling the plurality of drive inputs to the plurality of sliding rack gears, wherein:
actuation of the first drive output drives the first drive input, thereby moving the first sliding rack gear to perform a first function; and
actuation of the second drive output drives the second drive input, thereby moving the second sliding rack gear to perform a second function different than the first function; and
a tailpiece arranged at a proximal end of the shaft, the tailpiece including a housing and a manual actuation device mounted to the housing and manually and physically engageable by a user, wherein manual engagement of the manual actuation device by the user causes movement of the first sliding rack gear to perform the first function.

2. The robotic surgical tool of claim 1, wherein the manual actuation device comprises:
first and second buttons pivotably coupled to the housing;
a first pulley rotatably mounted to the first button;
a second pulley rotatably mounted to the second button;
a first cable wrapped around the first pulley and operatively coupled to a first pair of sliding rack gears of the plurality of sliding rack gears; and a second cable wrapped around the second pulley and operatively coupled to a second pair of sliding rack gears of the plurality of sliding rack gears, wherein manually depressing one of the first and second buttons simultaneously causes the other of the first and second buttons to pivot in an opposite direction and thereby move the first and second pairs of sliding rack gears to operate at least one of the end effector and the wrist.

3. The robotic surgical tool of claim 2, further comprising a tensioning nut threadably attached to the shaft at the proximal end and adjacent the housing, wherein rotating the tensioning nut applies an axial load on the housing and thereby places the first and second cables in tension.

4. The robotic surgical tool of claim 2, further comprising a manual accessory attachable to the tailpiece and including opposing handles, wherein at least one of the opposing handles is manually manipulatable to act on at least one of the first and second buttons.

5. The robotic surgical tool of claim 1, wherein the manual actuation device comprises:
   a slider that extends out of the housing and past an outer circumference of the housing;
   a first pulley arm mounted to the slider within the housing and having a first pulley rotatably mounted thereto;
   a second pulley arm mounted to the slider within the housing and having a second pulley rotatably mounted thereto;
   a first cable wrapped around the first pulley and operatively coupled to a first pair of sliding rack gears of the plurality of sliding rack gears; and
   a second cable wrapped around the second pulley and operatively coupled to a second pair of sliding rack gears of the plurality of sliding rack gears,
   wherein manually moving the slider about the outer circumference of the housing correspondingly moves the first and second pulley arms within the housing and thereby draws a length of the first cable into the tailpiece from the shaft while simultaneously paying out a length of the second cable into the shaft to move the first and second pairs of sliding rack gears and operate at least one of the end effector and the wrist.

6. The robotic surgical tool of claim 1, wherein the manual actuation device comprises:
   first and second camming plates movably mounted within the housing and vertically offset from each other, each camming plate defining distal and proximal slots that are angled to converge or diverge from one another;
   a slider defined on the first camming plate and extending out of the housing;
   a first pulley rotatably mounted to a first pin that extends between the first and second camming plates and into the distal slot of each camming plate;
   a second pulley rotatably mounted to a second pin that extends between the first and second camming plates and into the proximal slot of each camming plate;
   a first cable wrapped around the first pulley and operatively coupled to a first pair of sliding rack gears of the plurality of sliding rack gears; and
   a second cable wrapped around the second pulley and operatively coupled to a second pair of sliding rack gears of the plurality of sliding rack gears,
   wherein manually moving the slider correspondingly moves the first and second camming plates laterally within the housing and thereby urges the first and second pins to traverse the distal and proximal slots, respectively, which moves the first and second pulleys toward or away from each other, and
   wherein moving the first and second pulleys toward or away from each other acts on the first and second cables to move the first and second pairs of sliding rack gears and operate at least one of the end effector and the wrist.

7. The robotic surgical tool of claim 6, wherein each pulley comprises a spool having two parts matable at an engagement feature.

8. The robotic surgical tool of claim 1, wherein the manual actuation device comprises:
   a linear slider movably mounted within the housing and defining a rack gear;
   a slider having a first end that extends out of the housing and past an outer circumference of the housing and a second end that defines a pinion gear engageable with the rack gear;
   first and second pulleys rotatably mounted to opposing ends of the linear slider;
   a first cable wrapped around the first pulley and operatively coupled to a first pair of sliding rack gears of the plurality of sliding rack gears; and
   a second cable wrapped around the second pulley and operatively coupled to a second pair of sliding rack gears of the plurality of sliding rack gears,
   wherein manually moving the slider about the outer circumference of the housing correspondingly shifts the linear slider within the housing and thereby draws a length of the first cable into the tailpiece from the shaft while simultaneously paying out a length of the second cable into the shaft to move the first and second pairs of sliding rack gears and operate at least one of the end effector and the wrist.

9. The robotic surgical tool of claim 1, wherein the actuation system further includes:
   a plurality of drive gears, each drive gear being engageable with a corresponding one of the plurality of sliding rack gears; and
   a gear train extending between each drive input and each drive gear such that actuation of a given drive input drives the corresponding one of the plurality of sliding rack gears within a corresponding one of the plurality of longitudinal channels.

10. The robotic surgical tool of claim 9, wherein the gear train includes one or more intermediate gears that transition a rotational axis of the given drive input by 90° to enable the plurality of drive gears to engage the plurality of sliding rack gears.

11. The robotic surgical tool of claim 1, wherein the actuation system further includes:
   first and second mounting assemblies vertically offset from each other and concentrically arranged about the shaft; and
   a plurality of spur linkage subassemblies pivotably mounted to the first and second mounting assemblies, each spur linkage subassembly including a drive gear engageable with a corresponding one of the plurality of sliding rack gears,
   wherein moving the first mounting assembly toward the second mounting assembly pivots the plurality of spur linkage assemblies between a disengaged position, where the drive gear of each spur linkage subassembly is disengaged from the corresponding one of the plurality of sliding rack gears, and an engaged position, where the drive gear of each spur linkage subassembly is engaged with the corresponding one of the plurality of sliding rack gears.

12. The robotic surgical tool of claim 11, wherein each spur linkage subassembly includes:
a drive gear engageable with a corresponding one of the plurality of sliding rack gears; and
a gear train extending between a corresponding one of the plurality of drive inputs and the drive gear such that actuation of the corresponding one of the plurality of drive inputs drives the corresponding one of the plurality of sliding rack gears within a corresponding one of the plurality of longitudinal channels.

13. The robotic surgical tool of claim 12, wherein each spur linkage subassembly further includes:
a first linkage pivotably coupled to the first mounting assembly; and
a second linkage having a first end pivotably coupled to the first linkage and a second end pivotably coupled to the second mounting assembly.

14. The robotic surgical tool of claim 12, wherein the actuation system further includes a clocking wheel linkage subassembly comprising:
a first linkage pivotably coupled to the first mounting assembly;
a second linkage having a first end pivotably coupled to the first linkage at a pivot axis and a second end pivotably coupled to the second mounting assembly; and
a clocking wheel rotatably mounted to the first and second linkages at the pivot axis,
wherein moving the first mounting assembly toward the second mounting assembly pivots the clocking wheel linkage subassembly between the disengaged position, where the clocking wheel is disengaged from a longitudinal groove defined in the shaft, and the engaged position, where the clocking wheel is engaged with the longitudinal groove and thereby angularly aligns each spur linkage subassembly with the corresponding one of the plurality of sliding rack gears.

15. The robotic surgical tool of claim 1, wherein the first function comprises rotating at least a portion of the end effector relative to the elongate shaft about the articulable wrist and the second function comprises translating the elongate shaft and the end effector relative to the handle.

16. A method, comprising:
arranging a robotic surgical tool adjacent a patient, the robotic surgical tool including:
a handle providing a plurality of drive inputs including first and second drive inputs, the handle being couplable to an instrument driver of a robotic surgical system, and the instrument driver comprising a first and second drive outputs for driving the first and second drive input, respectively;
an elongate shaft extendable through the handle and including a plurality of sliding rack gears movably nested within a corresponding plurality of longitudinal channels defined along the shaft, the plurality of sliding rack gears including first and second sliding rack gears independently moveable relative to one another;
an end effector arranged at a distal end of the shaft and an articulable wrist interposing the end effector and the distal end;
an actuation system housed within the handle and operatively coupling the plurality of drive inputs to the plurality of sliding rack gears, wherein:
actuation of the first drive output drives the first drive input, thereby moving the first sliding rack gear to perform a first function;
actuation of the second drive output drives the second drive input, thereby moving the second sliding rack gear to perform a second function different than the first function; and
a tailpiece arranged at a proximal end of the shaft, the tailpiece including a housing and a manual actuation device mounted to the housing and manually and physically engageable by a user;
manually actuating the manual actuation device by the user and thereby causing movement of the first sliding rack gear to perform the first function; and
robotically actuating the actuation system via the plurality of drive outputs and thereby causing movement of the plurality of sliding rack gears to perform at least one of the first and second functions.

17. The method of claim 16, wherein the manual actuation device comprises first and second buttons pivotably coupled to the housing, a first pulley rotatably mounted to the first button, a second pulley rotatably mounted to the second button, a first cable wrapped around the first pulley and operatively coupled to a first pair of sliding rack gears of the plurality of sliding rack gears, and a second cable wrapped around the second pulley and operatively coupled to a second pair of sliding rack gears of the plurality of sliding rack gears, the method further comprising:
manually depressing one of the first and second buttons and thereby simultaneously causing the other of the first and second buttons to pivot in an opposite direction to move the first and second pairs of sliding rack gears and operate at least one of the end effector and the wrist.

18. The method of claim 17, wherein the tailpiece further includes a tensioning nut threadably attached to the shaft at the proximal end and adjacent the housing, the method further comprising rotating the tensioning nut and thereby applying an axial load on the housing and placing the first and second cables in tension.

19. The method of claim 16, wherein the manual actuation device comprises a slider that extends out of the housing and past an outer circumference of the housing, a first pulley arm mounted to the slider within the housing and having a first pulley rotatably mounted thereto, a second pulley arm mounted to the slider within the housing and having a second pulley rotatably mounted thereto, a first cable wrapped around the first pulley and operatively coupled to a first pair of sliding rack gears of the plurality of sliding rack gears, and a second cable wrapped around the second pulley and operatively coupled to a second pair of sliding rack gears of the plurality of sliding rack gears, the method further comprising:
manually moving the slider about the outer circumference of the housing and thereby correspondingly moving the first and second pulley arms within the housing; and
as the first and second pulley arms move within the housing, drawing a length of the first cable into the tailpiece from the shaft while simultaneously paying out a length of the second cable into the shaft to move the first and second pairs of sliding rack gears and operate at least one of the end effector and the wrist.

20. The method of claim 16, wherein the manual actuation device comprises first and second camming plates movably mounted within the housing and vertically offset from each other, each camming plate defining distal and proximal slots that are angled to converge or diverge from one another, a slider defined on the first camming plate and extending out of the housing, a first pulley rotatably mounted to a first pin that extends between the first and second camming plates and into the distal slot of each camming plate, a second pulley rotatably mounted to a second pin that extends between the first and second camming plates and into the proximal slot of each camming plate, a first cable wrapped around the first pulley and operatively coupled to a first pair of sliding rack gears of the plurality of sliding rack gears, and a second cable wrapped around the second pulley and operatively coupled to a second pair of sliding rack gears of the plurality of sliding rack gears, the method further comprising:

manually moving the slider and thereby correspondingly moving the first and second camming plates laterally within the housing;

as the first and second camming plates laterally within the housing, urging the first and second pins to traverse the distal and proximal slots, respectively, which moves the first and second pulleys toward or away from each other; and moving the first and second pulleys toward or away from each and thereby acting on the first and second cables to move the first and second pairs of sliding rack gears and operate at least one of the end effector and the wrist.

* * * * *